US009663557B2

(12) United States Patent
Lauer et al.

(10) Patent No.: US 9,663,557 B2
(45) Date of Patent: May 30, 2017

(54) SIGNAL PEPTIDE FUSION PARTNERS FACILITATING LISTERIAL EXPRESSION OF ANTIGENIC SEQUENCES AND METHODS OF PREPARATION AND USE THEREOF

(71) Applicant: Aduro BioTech, Inc., Berkeley, CA (US)

(72) Inventors: Peter M. Lauer, Albany, CA (US); William G. Hanson, Walnut Creek, CA (US); Justin Skoble, Berkeley, CA (US); Meredith Lai Ling Leong, Oakland, CA (US); Marcella Fasso, Richmond, CA (US); Dirk Brockstedt, Richmond, CA (US); Thomas W. Dubensky, Jr., Piedmont, CA (US)

(73) Assignee: ADURO BIOTECH, INC., Berkeley, CA (US)

( * ) Notice: Subject to any disclaimer, the term of this patent is extended or adjusted under 35 U.S.C. 154(b) by 98 days.

(21) Appl. No.: 14/142,614

(22) Filed: Dec. 27, 2013

(65) Prior Publication Data
US 2014/0186387 A1 Jul. 3, 2014

Related U.S. Application Data

(60) Provisional application No. 61/746,237, filed on Dec. 27, 2012, provisional application No. 61/780,744, filed on Mar. 13, 2013.

(51) Int. Cl.
C07K 19/00 (2006.01)
C07K 14/195 (2006.01)

(52) U.S. Cl.
CPC ........ C07K 14/195 (2013.01); C07K 2319/02 (2013.01); C07K 2319/036 (2013.01); C07K 2319/35 (2013.01); C07K 2319/40 (2013.01)

(58) Field of Classification Search
None
See application file for complete search history.

(56) References Cited

U.S. PATENT DOCUMENTS

| | | | |
|---|---|---|---|
| 5,767,063 A | 6/1998 | Lee et al. | |
| 5,830,702 A | 11/1998 | Portnoy et al. | |
| 5,888,530 A | 3/1999 | Netti et al. | |
| 6,051,237 A | 4/2000 | Paterson | |
| 6,090,611 A | 7/2000 | Covacci et al. | |
| 6,099,848 A | 8/2000 | Frankel et al. | |
| 6,379,943 B1 | 4/2002 | Graham et al. | |
| 6,855,320 B2 | 2/2005 | Paterson | |
| 7,935,804 B2 | 5/2011 | Dubensky et al. | |
| 2002/0150588 A1 | 10/2002 | Allison et al. | |
| 2004/0013690 A1 | 1/2004 | Portnoy et al. | |
| 2005/0048081 A1 | 3/2005 | Frankel et al. | |
| 2005/0249748 A1 | 11/2005 | Dubensky, Jr. et al. | |
| 2005/0281783 A1 | 12/2005 | Kinch et al. | |
| 2010/0291140 A1 | 11/2010 | Paterson et al. | |

FOREIGN PATENT DOCUMENTS

| | | |
|---|---|---|
| WO | 9614087 A1 | 5/1996 |
| WO | 9925376 A1 | 5/1999 |
| WO | 2004006837 A2 | 1/2004 |
| WO | 2007103225 A2 | 9/2007 |
| WO | 2007117371 A2 | 10/2007 |
| WO | 2008008311 A1 | 1/2008 |
| WO | 2008109155 A2 | 9/2008 |
| WO | 2009143085 A1 | 11/2009 |
| WO | 2011160859 A1 | 12/2011 |
| WO | 2012068360 A1 | 5/2012 |
| WO | 2012125551 A1 | 9/2012 |
| WO | 2013138337 A1 | 9/2013 |

OTHER PUBLICATIONS

Sewell et al. (Cancer Res. 64:8821-8825, 2004).*
Search Report issued by the Eurasian Patent Office in Eurasian Patent Application No. 201590397 dated Feb. 12, 2016—incl Engl lang transl.
Search Report and Written Opinion issued by IPOS in Singapore Application No. 11201502792T dated Mar. 4, 2015—incl Engl lang transl.
Lety et al., Identification of a PEST-like motif in listeriolysin O required for phagosomal escape and for virulence in Listeria monocytogenes. Mol Microbiol. Mar. 2001;39(5):1124-1139.
International Search Report and Written Opinion issued in PCT/US2013/078119 dated Apr. 25, 2014.
Disis et al., Humoral Epitope-Spreading Following Immunization with a HER-2/neu Peptide Based Vaccine in Cancer Patients. J Clin Immunol. Sep. 2004;24(5):571-578.
Dosaka-Akita et al., Expression of N-Acetylglucosaminyltransferase V Is Associated with Prognosis and Histology in Non-Small Cell Lung Cancers. Clin Cancer Res. Mar. 1, 2004;10(5):1773-1779.
Duxbury et al., CEACAM6 as a novel target for indirect type 1 immunotoxin-based therapy in pancreatic adenocarcinoma. Biochem Biophys Res Commun. May 7, 2004;317(3):837-843.
Elgh et al., Serological Diagnosis of Hantavirus Infections by an Enzyme-Linked Immunosorbent Assay Based on Detection of Immunoglobulin G and M Responses to Recombinant Nucleocapsid Proteins of Five Viral Serotypes. J Clin Microbiol. May 1997,35(5):1122-1130.

(Continued)

Primary Examiner — Brian J Gangle
(74) Attorney, Agent, or Firm — Acuity Law Group, P.C.; Michael Whittaker

(57) ABSTRACT

The present invention provides nucleic acids, expression systems, and vaccine strains which provide efficient expression and secretion of antigens of interest into the cytosol of host cells, and elicit effective CD4 and CD8 T cell responses by functionally linking Listerial or other bacterial signal peptides/secretion chaperones as N-terminal fusion partners in translational reading frame with selected recombinant encoded protein antigens. These N-terminal fusion partners are deleted (either by actual deletion, by mutation, or by a combination of these approaches) for any PEST sequences native to the sequence, and/or for certain hydrophobic residues.

21 Claims, 13 Drawing Sheets

(56) References Cited

OTHER PUBLICATIONS

Engels et al., Serologic Evidence for Exposure to Simian Virus 40 in North American Zoo Workers. J Infect Dis. Dec. 15, 2004;190(12)2065-2069.

Enjoji et al., RCAS1, a Useful Serum Marker to Predict the Recurrence of Cancer: Two Cases of Cholangiocarcinoma and Pancreatic Cancer. Dig Dis Sci. Oct. 2004;49(10):1654-1656.

Ericson et al., Expression of Cyclin-Dependent Kinase 6, but not Cyclin-Dependent Kinase 4, Alters Morphology of Cultured Mouse Astrocytes. Mol Cancer Res. Jul. 2003;1(9):654-664.

Estrada-Franco et al., Venezuelan Equine Encephalitis Virus, Southern Mexico. Emerg Infect Dis. Dec. 2004; 10(12):2113-2121.

Fang et al., Expression of Dnmt1, demethylase, MeCP2 and methylation of tumor-related genes in human gastric cancer World J Gastroenterol. Dec. 1, 2004;10(23):3394-3398.

Faure et al., Inducible Hsp70 as Target of Anticancer Immunotherapy: Identification of HLA-A*0201-Restricted Epitopes. Int J Cancer Mar. 1, 2004;108(6):863-870.

Fleishhauer et al., The DAM Gene Family Encodes a New Group of Tumor-specific Antigens Recognized by Human Leukocyte Antigen Al-restricted Cytotoxic T Lymphocytes. Cancer Res. Jul. 15, 1998;58(14):2969-2972.

Fong et al., Altered peptide ligand vaccination with Flt3 ligand expanded dendritic cells for tumor immunotherapy. Proc Natl Acad Sci U S A. Jul. 17, 2001;98(15):8809-8814.

Fuessel et al., Multiple tumor marker analyses (PSA, hK2, PSCA, trp-p8) in primary prostate cancers using quantitative RT-PCR. Int J Oncol. Jul. 2003;23(1):221-228.

Gaillard et al., Entry of L. monocytogenes into Cells Is Mediated by Internalin, a Repeat Protein Reminiscent of Surface Antigens from Gram-Positive Cocci. Cell. Jun. 28, 1991;65(7):1127-1141.

Gambus et al., Epitope mapping of a mouse monoclonal anti-MUC2 antibody suggests the existence of an immunodominant region in the COOH terminus of the MUC2 tandem-repeat sequence. Int J Cancer. Jan. 3, 1995;60 (1):146-148.

Geisbert and Jahrling, Differentiation of filoviruses by electron microscopy. Virus Res. Dec. 1995;39(2-3):129-150.

Ghazizadeh et al., Role of cdk4, p16INK4, and Rb Expression in the Prognosis of Bronchioloalveolar Carcinomas. Respiration. Jan.-Feb. 2005;72(1):68-73.

Gherardi et al., Towards a new generation of vaccines: the cytokine IL-12 as an adjuvant to enhance cellular immune responses to pathogens during prime-booster vaccination regimens. Histol Histopathol. Apr. 2001;16 (2):655-667.

Gilliam et al., A phase II study of G17DT in gastric carcinoma. Eur J Surg Oncol. Jun. 2004;30(5):536-543.

Gonzalez et al., A comparative sequence analysis to revise the current taxonomy of the family Coronaviridae. Arch Virol. Nov. 2003;148(11):2207-2235.

Good et al., Development and regulation of cell-mediated immune responses to the blood stages of malaria: implications for vaccine research. Annu Rev Immunol. 2005;23:69-99.

Good et al., The immunological challenge to developing a vaccine to the blood stages of malaria parasites. Immunol Rev. Oct. 2004:201:254-267.

Greiner et al., Vaccine-Based Therapy Directed against Carcinoembryonic Antigen Demonstrates Antitumor Activity on Spontaneous Intestinal Tumors in the Absence of Autoimmunity. Cancer Res. Dec. 1, 2002;62(23):6944-6951.

Grimm et al., Mouse alpha-fetoprotein-specific DNA-based immunotherapy of hepatocellular carcinoma leads to tumor regression in mice. Gastroenterology. Oct. 2000;119(4):1 104-1112.

Groh et al., Efficient cross-priming of tumor antigen-specific T cells by dendritic cells sensitized with diverse anti-MICA opsonized tumor cells. Proc Natl Acad Sci USA. May 3, 2005;102(18):6461-6466.

Groth and Calos, Phage Integrases: Biology and Applications. J Mol Biol. Jan. 16, 2004;335(3):667-678.

Gueguen et al., An Antigen Recognized by Autologous CTLs on a Human Bladder Carcinoma. J Immunol. Jun. 15, 1998;160(12):6188-6194.

Gulmann et al., Adenomatous Polyposis Coli Gene, beta-Catenin, and E-Cadherin Expression in Proximal and Distal Gastric Cancers and Precursor Lesions. Appl Immunohistochem Mol Morphol. Sep. 2003;11(3):230-237.

Gunn et al., Two Listeria Monocytogenes Vaccine Vectors That Express Different Molecular Forms of Human Papilloma Virus-16 (HPV-16) E7 Induce Qualitatively Different T Cell Immunity That Correlates With Their Ability to Induce Regression of Established Tumors Immortalized by HPV-16. J Immunol. Dec. 11, 2001;167(11):6471-6479.

Gupta et al., Refolding, purification, and crystallization of apical membrane antigen 1 from Plasmodium falciparum. Protein Expr Purif. May 2005;41(1):186-198.

Haddad et al., Novel antigen identification method for discovery of protective malaria antigens by rapid testing of DNA vaccines encoding exons from the parasite genome. Infect Immun. Mar. 2004;72(3):1594-1602.

Hakansson et al., Establishment and phenotypic characterization of human U937 cells with inducible P210 BCR/ABL expression reveals upregulation of CEACAM1 (CD66a). (2004) Leukemia 18:538-547.

Harris et al., The Biological and Therapeutic Importance of Gastrin Gene Expression in Pancreatic Adenocarcinomas. Cancer Res. Aug. 15, 2004;64(16):5624-5631.

Hashido et al., Evaluation of an Enzyme-Linked Immunosorbent Assay Based on Binding Inhibition for Type-Specific Quantification of Poliovirus Neutralization-Relevant Antibodies. Microbiol Immunol. 1999;43(1):73-77.

Hassan et al., Mesothelin: A New Target for Immunotherapy. Clin Cancer Res. Jun 15, 2004;10(12 Pt 1):3937-3942.

Havlasova et al., Mapping of immunoreactive antigens of Francisella tularensis live vaccine strain. Proteomics. Jul. 2002;2(7):857-867.

Havlasova et al., Proteomic analysis of anti-Francisella tularensis LVS antibody response in murine model of tularemia. Proteomics. May 2005;5(8):2090-2103.

He et al., Complexes of Poliovirus Serotypes with Their Common Cellular Receptor, CD155. J Virol. Apr. 2003;77 (8):4827-4835.

Hirose et al., Incidence of Diffuse Large B-Cell Lymphoma of Germinal Center B-Cell Origin in Whole Diffuse Large B-Cell Lymphoma: Tissue Fluorescence In Situ Hybridization Using t(14;18) Compared with Immunohistochemistry. Int J Hematol. Jan. 2005;81(1):48-57.

Hoffman et al., Strategy for development of a pre-erythrocytic Plasmodium falciparum DNA vaccine for human use Vaccine. Jun. 1997;15(8):842-845.

Hoke, History of U.S. Military Contributions to the Study of Viral Encephalitis. Mil Med. Apr. 2005;170(4 Suppl):92-105.

Howard et al., Differentiation of Listeria monocytogenes, Listeria innocua, Listeria ivanovii, and Listeria seeligeri by pulsed-field gel electrophoresis. Appl Environ Microbiol. Feb. 1992;58(2):709-712.

Hussain and Paterson, What is needed for effective antitumor immunotherapy? Lessons learned using Listeria monocytogenes as a live vector for HPV-associated tumors. Cancer Immunol Immunother. Jun. 2005;54(6):577-586.

Hutchinson et al., Multiplex Analysis of Cytokines in the Blood of Cynomolgus Macaques Naturally Infected With Ebola Virus (Reston Serotype). J Med Virol. Nov. 2001;65(3):561-566.

Iacobuzio-Donahue et al., Highly Expressed Genes in Pancreatic Ductal Adenocarcinomas: A Comprehensive characterization and Comparison of the Transcription Profiles Obtained from Three Major Technologies. Cancer Res. Dec. 15, 2003;63(24):8614-8622.

Iqbal et al., BCL2 Translocation Defines a Unique Tumor Subset within the Germinal Center B-Cell-Like Diffuse Large B-Cell Lymphoma. Am J Pathol. Jul. 2004;165(1):159-166.

Isherwood et al., Vaccination strategies for Francisella tularensis. Adv Drug Deliv Rev. Jun. 17, 2005;57 (9)1403-1414.

(56) References Cited

OTHER PUBLICATIONS

Ito et al., Prostate Carcinoma Detection and Increased Prostate-Specific Antigen Levels after 4 Years in Dutch and Japanese Males Who Had No Evidence of Disease at Initial Screening. Cancer Jan. 15, 2005;103(2):242-250.
Jainkittivong and Langlais, Herpes B virus infection. Oral Surg Oral Med Oral Pathol Oral Radiol Endod. Apr. 1998;85(4):399-403.
Jamieson et al., Human Torovirus: A New Nosocomial Gastrointestinal Pathogen. J Infect Dis. Nov. 1998;178 (5):1263-1269.
Abutaily et al., Cadherins, catenins and APC in pleural malignant mesothelioma. J Pathol. Nov. 2003;201(3):355-36.
Aguilar et al., Endemic Venezuelan equine encephalitis in northern Peru. Emerg Infect Dis. May 2004;10(5):880-888.
Ahn et al. All CVB Serotypes and Clinical Isolates Induce Irreversible Cytopathic Effects in Primary Cardiomyocytes. J Med Virol. Feb. 2005;75(2):290-294.
Altwein and Luboldt, Prognostic Factors for Carcinoma of the Prostate. Urol Int. 1999;63(1):62-71.
Alvarez-Lafuente et al., Human parvovirus B19, varicella zoster virus, and human herpes virus 6 in temporal artery biopsy specimens of patients with giant cell arteritis: analysis with quantitative real time polymerase chain reaction. Ann Rheum Dis. May 2005;64(5):780-782.
Andersen and thor Straten, Survivin—a universal tumor antigen. Histol Histopathol. Apr. 2002;17(2):669-675.
Argani et al., Discovery of New Markers of Cancer through Serial Analysis of Gene Expression Prostate Stem Cell Antigen Is Overexpressed in Pancreatic Adenocarcinoma. Cancer Res. Jun. 1, 2001;61(11):4320-4324.
Arora et al., Identification of Differentially Expressed Genes in Oral Squamous Cell Carcinoma. Mol Carcinog. Feb. 2005;42(2):97-108.
Arslan et al., A new approach to sequence comparison: normalized sequence alignment. Bioinformatics. Apr. 2001;17(4):327-337.
Attoui et al., Comparative sequence analysis of American, European and Asian isolates of viruses in the genus *Coltivirus*. J Gen Virol. Oct. 1998;79 ( Pt 10)2481-2489.
Auerbuch et al., Development of a Competitive Index Assay to Evaluate the Virulence of Listeria monocytogenes actA Mutants during Primary and Secondary Infection of Mice. Infect Immun. Sep. 2001;69(9):5953-5957.
Barbanti-Brodano et al., Simian virus 40 infection in humans and association with human diseases: results and hypotheses. Virology. Jan. 5, 2004;318(1):1-9.
Barthold et al., Infectivity, Disease Patterns, and Serologic Profiles of Reovirus Serotypes 1, 2, and 3 in Infant and Weanling Mice. Lab Anim Sci. Oct. 1993;43(5):425-430.
Baurain et al., High Frequency of Autologous Anti-Melanoma CTL Directed Against an Antigen Generated by a Point Mutation in a New Helicase Gene. J Immunol. Jun. 1, 2000;164(11):6057-6066.
Bevanger et al., Competitive Enzyme Immunoassay for Antibodies to a 43,000-Molecular-Weight Francisella tularensis Outer Membrane Protein for the Diagnosis of Tularemia. J Clin Microbiol. May 1989;27(5):922-926.
Bhigjee et al., Sequence of the env gene of some KwaZulu-Natal, South African strains of HTLV type I. AIDS Res Hum Retroviruses. Sep. 1, 1999;15(13):1229-1233.
Biagini et al., Simultaneous measurement of specific serum IgG responses to five select agents. Anal Bioanal Chem. Jun. 2005;382(4):1027-1034.
Bishop and Hinrichs, Adoptive transfer of immunity to Listeria monocytogenes. The influence of in vitro stimulation on lymphocyte subset requirements. J Immunol. Sep. 15, 1987;139(6)2005-2009.
Bondurant et al., Definition of an Immunogenic Region Within the Ovarian Tumor Antigen Stratum Comeum ahymotryptic Enzyme. Clin Cancer Res. May 1, 2005;11(9):3446-3454.
Brezniceanu et al., HMGB1 inhibits cell death in yeast and mammalian cells and is abundantly expressed in human breast carcinoma. FASEB J. Jul. 2003;17(10):1295-1297.

Brian and Baric, Coronavirus Genome Structure and Replication. Curr Top Microbiol Immunol. 2005;287:1-30.
Brinkmann et al., Novel Genes in the PAGE and GAGE Family of Tumor Antigens Found by Homology Walking in the dbEST Database. Cancer Res. Apr. 1, 1999;59(7):1445-1448.
Brockstedt et al., Killed but metabolically active microbes: a new vaccine paradigm for eliciting effector T-cell responses and protective immunity. Nat Med. Aug. 2005;11(8):853-860.
Brockstedt et al., Listeria-based cancer vaccines that segregate immunogenicity from toxicity. Proc Natl Acad Sci U S A. Sep. 21, 2004;101(38):13832-13837 plus supporting information (12 pages total).
Bronte et al., Genetic Vaccination with "Self" Tyrosinase-related Protein 2 Causes Melanoma Eradication but not Vitiligo. Cancer Res. Jan. 15, 2000;60(2):253-258.
Brown et al., Complete Genomic Sequencing Shows that Polioviruses and Members of Human Enterovirus Species C Are Closely Related in the Noncapsid Coding Region. J Virol. Aug. 2003;77(16):8973-8984.
Brown, Variants of B19. Dev Biol (Basel). 2004;118:71-77.
Capdepont et al., New Insights in HTLV-I Phylogeny by Sequencing and Analyzing the Entire Envelope Gene. AIDS Res Hum Retroviruses. Jan. 2005;21(1):28-42.
Capurro et al., Glypican-3: A Novel Serum and Histochemical Marker for Hepatocellular Carcinoma. Gastroenterology. Jul. 2003;125(1):89-97.
Carbone et al., New developments about the association of SV40 with human mesothelioma. Oncogene. Aug. 11, 2003;22(33):5173-5180.
Chan et al., In Situ Hybridization Study of PSP94 (Prostatic Secretory Protein of 94 Amino Acids) Expression in Human Prostates. Prostate. Oct. 1, 1999;41(2):99-109.
Chang et al., A Phase I Trial of Tumor Lysate-Pulsed Dendritic Cells in the Treatment of Advanced Cancer. Clin cancer Res. Apr. 2002;8(4):1021-1032.
Chen et al., Immunodominant CD41 responses identified in a patient vaccinated with full-length NY-ESO-1 formulated with ISCOMATRIX adjuvant. Proc Natl Acad Sci USA. Jun. 22, 2004;101(25):9363-9368.
Chern et al., Glycoprotein B Subtyping of Cytomegalovirus (CMV) in the Vitreous of Patients with AIDS and CMV Retinitis. J Infect Dis. Oct. 1998;178(4):1149-1153.
Chiari et al., Two Antigens Recognized by Autologous Cytolytic T Lymphocytes on a Melanoma Result from a Single Point Mutation in an Essential Housekeeping Gene. Cancer Res. Nov. 15, 1999;59(22):5785-5792.
Christiansen et al., Polarity of Prostate Specific Membrane Antigen, Prostate Stem Cell Antigen, and Prostate Specific Antigen in Prostate Tissue and in a Cultured Epithelial Cell Line. Prostate. Apr. 1, 2003;55(1):9-19.
Clements et al., Adenomatous Polyposis Coli/β-Catenin Interaction and Downstream Targets: Altered Gene Expression in Gastrointestinal Tumors. Clin Colorectal Cancer. Aug. 2003;3(2):113-120.
Clifton et al., A chlamydial type III translocated protein is tyrosine-phosphorylated at the site of entry and associated with recruitment of actin. Proc Natl Acad Sci USA. Jul. 6, 2004;101(27):10166-10171.
Clinton et al., A Comparative Study of Four Serological Tumor Markers for the Detection of Breast Cancer. Biomed Sci Instrum. 2003;39:408-414.
Cobaleda et al., A primitive hematopoietic cell is the target for the leukemic transformation in human Philadelphia-positive acute lymphoblastic leukemia. Blood. Feb. 1, 2000;95(3):1007-1013.
Cordington et al., Analysis of ETV6/AML1 abnormalities in acute lymphoblastic leukaemia: incidence, alternative spliced forms and minimal residual disease value. Br J Haematol. Dec. 2000;111(4):1071-1079.
Creighton et al., Mechanisms and catalysts of disulfide bond formation in proteins. Trends Biotechnol. Jan. 1995;13 (1):18-23.
Dalerba et al., MAGE, BAGE and GAGE gene expression in human rhabdomyosarcomas. Int J Cancer. Jul. 1, 2001;93(1):85-90.

(56) References Cited

OTHER PUBLICATIONS

Damasus-Awatai and Freeman-Wang, Human papilloma virus and cervical screening. Curr Opin Obstet Gynecol. Dec. 2003;15(6):473-477.

Das et al., Evaluation of a Western Equine Encephalitis recombinant E1 protein for protective immunity and diagnostics. Antiviral Res. Nov. 2004;64(2):85-92.

Davies et al., Characterisation of a recombinant Fv fragment of anti-MUC1 antibody HMFG1. Cancer Lett. Jul. 29, 1997;82(2):179-184.

De Backer et al., Characterization of the GAGE Genes That Are Expressed in Various Human Cancers and in Normal Testis. Cancer Res. Jul. 1, 1999;59(13):3157-3165.

de Villiers et al., Classification of papillomaviruses. Virology. Jun. 20, 2004;324(1):17-24.

Demidenko and Blagosklonny, Flavopiridol Induces p53 via Initial Inhibition of Mdm2 and P21 and, Independently of p53, Sensitizes Apoptosis-Reluctant Cells to Tumor Necrosis Factor. Cancer Res. May 15, 2004;64 (10):3653-3660.

Disis and Cheever, Her-2/Neu Protein: A Target for Antigen-Specific Immunotherapy of Human Cancer. Adv Cancer Res. 1997;71:343-371.

Slager et al., Induction of CAMEL/NY-ESO-ORF2-specific CD8+ T cells upon stimulation with dendritic cells infected with a modified Ad5 vector expressing a chimeric Ad5/35 fiber. Cancer Gene Ther. Mar. 2004;11(3):227-236.

Small et al., Immunotherapy of Hormone-Refractory Prostate Cancer With Antigen-Loaded Dendritic Cells. J Clin Oncol. Dec. 1, 2000;18(23):3894-3903.

Smith and Thorpe, Diversity in the serine recombinases. Mol Microbiol. Apr. 2002;44(2):299-307.

Smith et al., Measurement of Cell-Mediated Immunity With a Varicella-Zoster Virus-specific Interferon-gamma ELISPOT Assay: Responses in an Elderly Population Receiving a Booster Immunization. J Med Virol. 2003;70 Suppl 1:S38-S41.

Smith et al., Neutralization of HIV-1 Subtypes: Implications for Vaccine Formulations. J Med Virol. Nov. 1998;56 (3):264-268.

Smits et al., Phylogenetic and Evolutionary Relationships among Torovirus Field Variants: Evidence for Multiple Intertypic Recombination Events. J Virol. Sep. 2003;77(17):9567-9577.

Stams et al., Expression Levels of TEL, AML1, and the Fusion ProductsTEL-AML1 and AML1-TEL versus Drug Sensitivity and Clinical Outcome in t(12;21)-Positive Pediatric Acute Lymphoblastic Leukemia. Clin Cancer Res. Apr. 15, 2005;11(8):2974-2980.

Steffens et al., Immunohistochemical Analysis of Tumor Antigen Saturation Following Injection of Monoclonal Antibody G250. Anticancer Res. Mar.-Apr. 1999;19(2A):1197-1200.

Stirnadel et al., Assessment of different sources of variation in the antibody responses to specific malaria antigens in children in Papua New Guinea. Int J Epidemiol. Jun. 2000;29(3):579-586.

Stolier et al., Initial Experience with Surgical Treatment Planning in the Newly Diagnosed Breast Cancer Patient at High Risk for BRCA-1 or BRCA-2 Mutation. Breast J. Nov.-Dec. 2004;10(6):475-480.

Studahl et al., Herpesvirus DNA Detection in Cerebral Spinal Fluid: Differences in Clinical Presentation between Alpha-, Beta-, and Gamma-Herpesviruses. Scand J Infect Dis. 2000;32(3):237-248.

Suzuki et al., Identification of Natural Antigenic Peptides of a Human Gastric Signet Ring Cell Carcinoma Recognized by HLA-A31-Restricted Cytotoxic T Lymphocytes. J Immunol. Sep. 1, 1999;163(5):2783-2791.

Takahashi et al., 707-AP Peptide Recognized by Human Antibody Induces Human Leukocyte Antigen A2-Restricted Cytotoxic T Lymphocyte Killing of Melanoma. Clin Cancer Res. Aug. 1997;3(8):1363-1370.

Tamura et al., Identification of Cyclophilin B-derived Peptides Capable of Inducing Histocompatibility Leukocyte Antigen-A2-restricted and Tumor-specific Cytotoxic T Lymphocytes. Jpn J Cancer Res. Jul. 2001;92(7):762-767.

Tanaka et al., Expression of Tumor-rejection Antigens in Gynecologic Cancers. Jpn J Cancer Res. Nov. 2000;91 (11)1177-1184.

Tannapfel et al., BRAF Gene Mutations Are Rare Events in Gastroenteropancreatic Neuroendocrine Tumors. Am J Clin Pathol. Feb. 2005;123(2):256-260.

Treurnicht et al., HHV-8 Subtypes in South Africa: Identification of a Case Suggesting a Novel B Variant. J Med Virol. Feb. 2002;66(2):235-240.

Trimble et al., Comparison of the CD8+ T cell responses and antitumor effects generated by DNA vaccine administered through gene gun, biojector, and syringe. Vaccine. Sep. 8, 2003;21(25-26):4036-4042.

Trincado et al., Human Cytomegalovirus Strains Associated With Congenital and Perinatal Infections. J Med Virol. Aug. 2000;61(4):481-487.

Tsang et al., Phenotypic Stability of a Cytotoxic T-Cell Line Directed against an Immunodominant Epitope of Human Carcinoembryonic Antigen. Clin Cancer Res. Dec. 1997;3(12 Pt 1):2439-2449.

Tsao and Sober, Melanoma Treatment Update. Dermatol Clin. Apr. 2005;23(2):323-333.

Tsuruma et al., Phase I clinical study of anti-apoptosis protein, survivin-derived peptide vaccine therapy for patients with advanced or recurrent colorectal cancer J Transl Med. Jun. 13, 2004;2(1):19 (11 pages).

Vallejo et al., Nucleotide Sequence and Restriction Fragment-Length Polymorphism Analysis of Human T-Cell Lymphotropic Virus Type II (HTLV-II) in Southern Europe: Evidence for the HTLV-IIa and Htlv-IIb Subtypes. J Acquir Immune Defic Syndr Hum Retrovirol. Dec. 1, 1996;13(4)384-391.

Van Den Eynde et al., A New Antigen Recognized by Cytolytic T Lymphocytes on a Human Kidney Tumor Results from Reverse Strand Transcription. J Exp Med. Dec. 20, 1999;190(12):1793-1800.

Vandamme et al., African Origin of Human T-Lymphotropic Virus Type 2 (HTLV-2) Supported by a Potential New HTLV-2d Subtype in Congolese Bambuti Efe Pygmies. J Virol. May 1998;72(5):4327-4340.

Vazquez-Boland et al., Nucleotide Sequence of the Lecithinase Operon of Listeria monocytogenes and Possible Role of Lecithinase in Cell-to-Cell Spread. Infect Immun. Jan. 1992;60(1):219-230.

Vilas Boas et al., Cytomegalovirus Glycoprotein B Genotypes and Central Nervous System Disease in AIDS Patients. J Med Virol. Nov. 2003;71(3):404-407.

Vilchez and Butel, Emergent Human Pathogen Simian Virus 40 and Its Role in Cancer. Clin Microbiol Rev. Jul. 2004;17(3):495-508.

Virok et al., Chlamydial Infection Induces Pathobiotype-Specific Protein Tyrosine Phosphorylation in Epithelial Cells. Infect Immun. Apr. 2005;73(4):1939-1946.

Von Lindern et al., The Translocation (6;9), Associated with a Specific Subtype of Acute Myeloid Leukemia, Results in the Fusion of Two Genes, dek and can, and the Expression of a Chimeric, Leukemia-Specific dek-can mRNA. Mol Cell Biol. Apr. 1992;12(4):1687-1697.

Waltregny et al., Screening of histone deacetylases (HDAC) expression in human prostate cancer reveals distinct class I HDAC profiles between epithelial and stromal cells. Eur J Histochem. Jul.-Sep. 2004;48(3):273-290.

Wang et al., Alterations of APC, c-met, and p53 Genes in Tumor Tissue and Serum of Patients with Gastric Cancers. J Surg Res. Aug. 2004;120(2):242-248.

Wang et al., Cloning Genes Encoding MHC Class II—Restricted Antigens: Mutated CDC27 as a Tumor Antigen. Science. May 21, 1999;284(5418):1351-1354.

Wang et al., Identification of a Novel Major Histocompatibility Complex Class II-restricted Tumor Antigen Resulting from a Chromosomal Rearrangement Recognized by CD4+ T Cells. J Exp Med. May 17, 1999;189(10):1659-1667.

Weaver et al., Genetic determinants of Venezuelan equine encephalitis emergence. Arch Virol Suppl. 2004; (18):43-64.

Weaver et al., Venezuelan Equine Encephalitis. Annu Rev Entomol. 2004;49:141-174.

(56) References Cited

OTHER PUBLICATIONS

Weiskirch et al., Listeria monocytogenes: a potent vaccine vector for neoplastic and infectious disease. Immunol Rev. Aug. 1997;158:159-169.
Wells et al., Swine Influenza Virus Infections. Transmission From III Pigs to Humans at a Wisconsin Agricultural Fair and Subsequent Probable Person-To-Person Transmission. JAMA. Jan. 23-30, 1991;265(4):478-481.
Wentworth et al., An Influenza A (HINI) Virus, Closely Related to Swine Influenza Virus, Responsible for a Fatal Case of Human Influenza. J Virol. Apr. 1994;68(4):2051-2058.
Wong and Freitag, A Novel Mutation within the Central Listeria monocytogenes Regulator PrfA That Results in Constitutive Expression of Virulence Gene Products. J Bacteriol. Sep. 2004;186(18):6265-6276.
Woycechowsky and Raines, Native Disulfide Bond Formation in Proteins. Curr Opin Chem Biol. Oct. 2000;4 (5):533-539.
Zaremba, Identification of an Enhancer Agonist Cytotoxic T Lymphocyte Peptide from Human Carcinoembryonic Antigen. Cancer Res. Oct. 15, 1997;57(20):4570-4577.
Zeier et al., New Ecological Aspects of Hantavirus Infection: A Change of A Paradigm and a Challenge of Prevention—A Review. Virus Genes. Mar. 2005;30(2):157-180.
Zimmerman et al., Expression of annexin II in conventional renal cell carcinoma is correlated with Fuhrman grade and clinical outcome. Virchows Arch. Oct. 2004;445(4):368-374.
Ziyaeyan et al., The Seroprevalence of Parvovirus Bl9 Infection among To-Be-Married Girls, Pregnant Women, and Their Neonates in Shi raz, Iran. Jpn J Infect Dis. Apr. 2005;58(2):95-97.
Jansen and Shaw, Human Papillomavirus Vaccines and Prevention of Cervical Cancer. Annu Rev Med. 2004;55:319-331.
Johnson et al., Natural Atypical Listeria innocua Strains with Listeria monocytogenes Pathogenicity Island 1 Genes. Appl Environ Microbiol. Jul. 2004;70(7):4256-4266.
Jones and Portnoy, Characterization of Listeria monocytogenes Pathogenesis in a Strain Expressing Perfringolysin O in Place of Listeriolysin O. Infect Immun. Dec. 1994;62(12):5608-5613.
Jung et al., Strategies Against Human Papillomavirus Infection and Cervical Cancer. J Microbiol. Dec. 2004;42 (4):255-266.
Jungck et al., E-cadherin expression is homogeneously reduced in adenoma from patients with familial adenomatous polyposis: an immunohistochemical study of E-cadherin, beta-catenin and cyclooxygenase-2 expression. Int J Colorectal Dis. Sep. 2004;19(5):438-445.
Kann and Goldstein, Performance Evaluation of a New Algorithm for the Detection of Remote Homologs With Sequence Comparison. Proteins. Aug. 1, 2002;48(2):367-376.
Kaufman et al., Parvovirus B19 does not bind to membrane-associated globoside in vitro. Virology. Feb. 5, 2005;332 (1)189-198.
Kedl et al., Comparative Sequence Analysis of the Reovirus S4 Genes from 13 Serotype 1 and Serotype 3 Field Isolates. (1995) J. Virol. 69:552-559.
Kim et al., Comparison of HPV DNA vaccines employing intracellular targeting strategies. Gene Ther. Jun. 2004;11 (12)1011-1018.
Krzych et al., T Lymphocytes from Volunteers Immunized with Irradiated Plasmodium Falciparum Sporozoites Recognize Liver and Blood Stage Malaria Antigens. J Immunol. Oct. 15, 1995;155(8):4072-4077.
Kubuschok et al., Expression of Cancer Testis Antigens in Pancreatic Carcinoma Cell Lines, Pancreatic Adenocarcinoma and Chronic Pancreatitis. Int J Cancer. Apr. 20, 2004;109(4):568-575.
Kumamuru et al., T-Cell Receptor Vbeta Gene Usage by T Cells Reactive with the Tumor-Rejection Antigen SART-1 in Oral Squamous Cell Carcinoma. Int J Cancer. Feb. 20, 2004;108(5):686-695.
Kyte and Doolittle, A Simple Method for Displaying the Hydropathic Character of a Protein. J Mol Biol. May 5, 1982;157(1)105-132.
Laheru and Jaffee, Immunotherapy for Pancreatic Cancer—Science Driving Clinical Progress. Nat Rev Cancer. Jun. 2005;5(6):459-467.
Lalic-Multhaler et al., In vitro transcription of PrfA-dependent and -independent genes of Listeria monocytogenes. Mol Microbiol. Oct. 2001;42(1):111-120.
Lauer et al., Constitutive Activation of the PrfA Regulon Enhances the Potency of Vaccines Based on Live-Attenuated and Killed but Metabolically Active Listeria monocytogenes Strains. Infect Immun. Aug. 2008;76 (8):3742-3753.
Lauer et al., Construction, Characterization, and Use of Two Listeria monocytogenes Site-Specific Phage Integration Vectors. J Bacteriol. Aug. 2002;184(15):4177-4186.
Lee et al., Immunomic analysis of human sarcoma. Proc Natl Acad Sci USA. Mar. 4, 2003;100(5)2651-2656.
Leroux-Roels et al., Prevention of Hepatitis B Infections: Vaccination and its Limitations. Acta Clin Belg. Jul.-Aug. 2001;56(4):209-219.
Li et al., Glycation End Products Induce Tubular Epithelial-Myofibroblast Transition through the RAGE-ERK1/2 MAP Kinase Signaling Pathway. Am J Pathol. Apr. 2004;164(4):1389-1397.
Li et al., Expression Profile of Cancer-Testis Genes in 121 Human Colorectal Cancer Tissue and Adjacent Normal Tissue. Clin Cancer Res. Mar. 1, 2005;11(5):1809-1814.
Liang et al., Microvessel density, cyclo-oxygenase 2 expression, K-ras mutation and p53 overexpression in colonic cancer. Br J Surg. Mar. 2004;91(3):355-361.
Liau et al., Tumor Immunity within the Central Nervous System Stimulated by Recombinant Listeria Monocytogenes Vaccination. Cancer Res. Apr. 15, 2002;62(8):2287-2293.
Lim et al., Molecular and phenotypic spectrum of de novo Philadelphia positive acute leukemia. Int J Mol Med. Dec. 1999;4(6):665-667.
Lin et al., Melanoma-Associated Antigens in Esophageal Adenocarcinoma: Identification of Novel MAGE-A10 Splice Variants. Clin Cancer Res. Sep. 1, 2004;10(17):5708-5716.
Lingnau et al., Expression of the Listeria monocytogenes EGD inlA and inlB Genes, Whose Products Mediate Bacterial Entry into Tissue Culture Cell Lines, by PrfA-Dependent and -Independent Mechanisms. Infect Immun. Oct. 1995;63(10):3896-3903.
Lucas et al., MAGE-B5, MAGE-B6, MAGE-C2, and MAGE-C3: Four New Members of the MAGE Family with Tumor-Expression. Int J Cancer. Jul. 1, 2000;87(1):55-60.
Luo et al., In vitro transcription of the Listeria monocytogenes virulence genes inlC and mpl reveals overlapping PrfA-dependent and -independent promoters that are differentially activated by GTP. Mol Microbiol. Apr. 2004;52(1):39-52.
Machlenkin et al., Human CTL Epitopes Prostatic Acid Phosphatase-3 and Six-Transmembrane Epithelial Antigen of Prostate-3 as Candidates for Prostate Cancer Immunotherapy. Cancer Res. Jul. 15, 2005;65(14):6435-6442.
Mandruzzato et al., A CASP-8 Mutation Recognized by Cytolytic T Lymphocytes on a Human Head and Neck Carcinoma. J Exp Med. Aug. 29, 1997;186(5):785-793.
Marth, Booster Policy for Adults. Biologicals. Jun. 1997;25(2):199-203.
Matsumoto et al., Expression of the SART-1 Antigens in Uterine Cancers. Jpn J Cancer Res. Dec. 1998;89 (12):1292-1295.
Matsushita et alPreferentially Expressed Antigen of Melanoma (PRAME) in the Development of Diagnostic and Therapeutic Methods for Hematological Malignancies. Leuk Lymphoma. Mar. 2003;44(3):439-444.
Mayo et al., Mdm-2 Phosphorylation by DNA-dependent Protein Kinase Prevents Interaction with p531. Cancer Res. Nov. 15, 1997;57(22):5013-5016.
McCool et al., Roles of calreticulin and calnexin during mucin synthesis in LS180 and HT29/A1 human colonic adenocarcinoma cells. Biochem J. Aug. 1, 1999;341 ( Pt 3):593-600.
McCune et al., Active specific immunotherapy with tumor cells and Corynebacterium parvum: A Phase I Study. Cancer. May 1979;43(5):1619-1623.

(56) References Cited

OTHER PUBLICATIONS

Millon et al., Detection of Prostate-Specific Antigen- or Prostate-Specific Membrane Antigen-Positive Circulating Cells in Prostatic Cancer Patients: Clinical Implications. Eur Urol. Oct. 1999;36(4):278-285.
Molijn et al., Molecular diagnosis of human papillomavirus (HPV) infections. J Clin Virol. Mar. 2005;32 Suppl 1: S43-51-S51.
Moreau-Aubry et al., A Processed Pseudogene Codes for a New Antigen Recognized by a CD8+ T Cell Clone on Melanoma. J Exp Med. May 1, 2000;191(9):1617-1624.
Morse et al., A Phase I Study of Active Immunotherapy with Carcinoembryonic Antigen Peptide (CAP-1)-Pulsed, Autologous Human Cultured Dendritic Cells in Patients with Metastatic Malignancies Expressing Carcinoembryonic Antigen. Clin Cancer Res. Jun. 1999;5(6):1331-1338.
Mueller and Freitag, Pleiotropic Enhancement of Bacterial Pathogenesis Resulting from the Constitutive Activation of the Listeria monocytogenes Regulatory Factor PrfA. Infect Immun. Apr. 2005;73(4):1917-1926.
Mukhopadhyay et al., A Structural Perspective of the Flavivirus Life Cycle. Nat Rev Microbiol. Jan. 2005;3(1):13-22.
Mulders et al., Tumor antigens and markers in renal cell carcinoma. Urol Clin North Am. Aug. 2003;30(3):455-465.
Muller et al., MeCP2 and MBD2 expression in human neoplastic and non-neoplastic breast tissue and its association with oestrogen receptor status. Br J Cancer Nov. 17, 2003;89(10):1934-1939.
Muminova et al., Characterization of human mesothelin transcripts in ovarian and pancreatic cancer. BMC Cancer. May 12, 2004;4:19.
Munson and Rodbard, Ligand: A Versatile Computerized Approach for Characterization of Ligand-Binding Systems. Anal Biochem. Sep. 1, 1980;107(1):220-239.
Nair et al., Induction of cytotoxic T cell responses and tumor immunity against unrelated tumors using telomerase reverse transcriptase RNA transfected dendritic cells. Nat Med. Sep. 2000;6(9):1011-1017.
Nakatsura et al., Cellular and humoral immune responses to a human pancreatic cancer antigen, coactosin-like protein, originally defined by the SEREX method. Eur J Immunol. Mar. 2002;32(3):826-836.
Nakatsura et al., Glypican-3, overexpressed specifically in human hepatocellular carcinoma, is a novel tumor marker. Biochem Biophys Res Commun. Jun. 20, 2003;306(1):16-25.
Nakatsura et al., Identification of Glypican-3 as a Novel Tumor Marker for Melanoma. Clin Cancer Res. Oct. 1, 2004;10(19):6612-6621.
Second Written Opinion issued by IPOS in Singapore application No. 11201502792T dated May 23, 2016—Engl lang transl only.
The Partial Supplementary European Search Report issued in EP 13869448 dated Aug. 16, 2016.
Singh and Wallecha, Cancer immunotherapy using recombinant Listeria monocytogenes: Transition from bench to clinic. Hum Vaccin. May 2011;7(5):497-505.
Sun and Liu, Listeriolysin O as a strong immunogenic molecule for the development of new anti-tumor vaccines. Hum Vaccin Immunother May 2013;9(5):1058-1068.
Wood et al., Cancer immunotherapy using Listeria monocytogenes and listerial virulence factors. Immunol Res. 2008;42(1-3):233-245.
Neumann et al., Identification of an HLA-DR-Restricted Peptide Epitope with a Promiscuous Binding Pattern Derived from the Cancer Testis Antigen HOM-MEL-40/SSX2. Int J Cancer Nov. 20, 2004;112(4):661-668.
Nicoletto et al., BRCA-1 and BRCA-2 mutations as prognostic factors in clinical practice and genetic counselling. Cancer Treat Rev. Oct. 2001;27(5):295-304.
Nunes-Duby et al., Similarities and differences among 105 members of the Int family of site-specific recombinases. Nucleic Acids Res. Jan. 15, 1998;26(2):391-406.
Oberste et al., Evidence for Frequent Recombination within Species Human Enterovirus B Based on Complete Genomic Sequences of All Thirty-Seven Serotypes. J Virol. Jan. 2004;78(2):855-867.

Oberthuer et al., The Tumor-Associated Antigen PRAME Is Universally Expressed in High-Stage Neuroblastoma and Associated with Poor Outcome. Clin Cancer Res. Jul. 1, 2004;10(13):4307-4313.
Oliveira-Perreira and Daniel-Ribeiro, Protective CD8+ T Cell Responses against the Pre-erythrocytic Stages of Malaria Parasites: an Overview. Mem Inst Oswaldo Cruz. Feb. 2001;96(2):221-227.
O'Riordan et al., Listeria Intracellular Growth and Virulence Require Host-Derived Lipoic Acid. Science. Oct. 17, 2003;302(5644):462-464.
Orvell et al., Antigenic relationships between six genotypes of the small hydrophobic protein gene of mumps virus. J Gen Virol. Oct. 2002;83(Pt 10):2489-2496.
Otte et al., MAGE-A Gene Expression Pattern in Primary Breast Cancer. Cancer Res. Sep. 15, 2001;61 (18):6682-6687.
Oyston and Quarry, Tularemia vaccine: past, present and future. Antonie Van Leeuwenhoek. May 2005;87 (4):277-281.
Padilla et al., Imaging of the Varicella Zoster Virion in the Viral Highways: Comparison With Herpes Simplex Viruses 1 and 2, Cytomegalovirus, Pseudorabies Virus, and Human Herpes Viruses 6 and 7. J Med Virol. 2003;70 Suppl 1: S103-S110.
Patel et al., Development of a simple restriction fragment length polymorphism assay for subtyping of coxsackie B viruses. J Virol Methods. Sep. 15, 2004;120(2)167-172.
Peh et al., Frequent presence of subtype A virus in Epstein-Barr virus-associated malignancies. Pathology. Oct. 2002;34(5):446-450.
Pisarev et al., Full-Length Dominant-Negative Survivin for Cancer Immunotherapy. Clin Cancer Res. Dec. 15, 2003;9 (17):6523-6533.
Porsch-Ozcurumez et al., Comparison of Enzyme-Linked Immunosorbent Assay, Western Blotting, Microagglutination, Indirect Immunofluorescence Assay, and Flow Cytometry for Serological Diagnosis of Tularemia. Clin Diagn Lab Immunol. Nov. 2004;11(6):1008-1015.
Ramsay et al., DNA vaccination against virus infection and enhancement of antiviral immunity following consecutive immunization with DNA and viral vectors. Immunol Cell Biol. Aug. 1997;75(4):382-388.
Renkvist et al., A listing of human tumor antigens recognized by T cells. Cancer Immunol Immunother. Mar. 2001;50 (1)3-15.
Reynolds et al., HLA-Independent Heterogeneity of CD8+ T Cell Responses to MAGE-3, Melan-A/MART-1, gp100, Tyrosinase, MC1R, and TRP-2 in Vaccine-Treated Melanoma Patients. J Immunol. Dec. 15, 1998;161(12):6970-6976.
Rezig et al., Molecular Characterization of Coxsackievirus B5 Isolates. J Med Virol. Feb. 2004;72(2):268-274.
Ries et al., Investigation of the expression of melanoma antigen-encoding genes (MAGE-A1 to -A6) in oral squamous cell carcinomas to determine potential targets for gene-based cancer immunotherapy. Int J Oncol. Mar. 2005;26 (3):817-824.
Ripio et al., A Gly145Ser Substitution in the Transcriptional Activator PrfA Causes Constitutive Overexpression of Virulence Factors in Listeria monocytogenes. J Bacteriol. Mar. 1997;179(5):1533-1540.
Roden and Wu, Preventative and therapeutic vaccines for cervical cancer. Expert Rev Vaccines. Aug. 2003;2 (4)495-516.
Roner et al., Identification of signals required for the insertion of heterologous genome segments into the reovirus genome. Proc Natl Acad Sci USA. Dec. 9, 1995;92(26):12362-12366.
Rozinov and Nolan, Evolution of peptides that modulate the spectral qualities of bound, small-molecule fluorophores. Chem Biol. Dec. 1998;5(12):713-728.
Salazar-Onfray et al., Synthetic Peptides Derived from the Melanocyte-Stimulating Hormone Receptor MC1R Can Stimulate HLA-A2-Restricted Cytotoxic T Lymphocytes That Recognize Naturally Processed Peptides on Human Melanoma Cells. Cancer Res. Oct. 1, 1997;57(19):4348-4355.
Santin et al., The serine protease stratum corneum chymotryptic enzyme (kallikrein 7) is highly overexpressed in squamous cervical cancer cells. Gynecol Oncol. Aug. 2004;94(2):283-288.
Sarcevic et al., Expression of Cancer/Testis Tumor Associated Antigens in Cervical Squamous Cell Carcinoma. Oncology. 2003;64(4):443-449.

(56) References Cited

OTHER PUBLICATIONS

Sarobe et al., Carcinoembryonic Antigen as a Target to Induce Anti-Tumor Immune Responses. Curr Cancer Drug Targets. Aug. 2004;4(5):443-454.

Sasaki et al., SAGE mRNA expression in advanced-stage lung cancers. Eur J Surg Oncol. Dec. 2003;29(10):900-903.

Sasatomi et al., Expression of Tumor Rejection Antigens in Colorectal Carcinomas. Cancer. Mar. 15, 2002;94 (6):1636-1641.

Scanlan et al., Cancer-related Serological Recognition of Human Colon Cancer: Identification of Potential Diagnostic and Immunotherapeutic Targets. Cancer Res. Jul. 15, 2002;62(14):4041-4047.

Scanlan et al., Expression of cancer-testis antigens in lung cancer: definition of bromodomain testis-specific gene (BRDT) as a new CT gene, CT9. Cancer Lett. Mar. 31, 2000;150(2):155-164.

Scanlan et al., Humoral immunity to human breast cancer: antigen definition and quantitative analysis of mRNA expression. Cancer Immun. Mar. 30, 2001;1:4 (17 pp).

Scanlan et al., The cancer/testis genes: Review, standardization, and commentary. Cancer Immun. Jan. 23, 2004;4:1 (15 pp).

Scarcella et al., Expression of MAGE and GAGE in High-Grade Brain Tumors: A Potential Target for Specific Immunotherapy and Diagnostic Markers. Clin Cancer Res. Feb. 1999;5(2):335-341.

Schmittgen et al., Expression of Prostate Specific Membrane Antigen and Three Alternatively Spliced Variants of PSMA in Prostate Cancer Patients. Int J Cancer Nov. 1, 2003;107(2):323-329.

Schwartz et al., Novel Targeted and Immunotherapeutic Strategies in Chronic Myeloid Leukemia. Semin Hematol. Jan. 2003;40(1):87-96.

Sepehr et al., Distinct pattern of TP53 mutations in squamous cell carcinoma of the esophagus in Iran. Oncogene. Nov. 1, 2001;20(50):7368-7374.

Sepulveda-Amor et al., A randomized trial demonstrating successful boosting responses following simultaneous aerosols of measles and rubella (MR) vaccines in school age children. Vaccine. Jun. 21, 2002;20(21-22):2790-2795.

Shen et al., Cloned Dendritic Cells Can Present Exogenous Antigens on Both MHC Class I and Class II Molecules. J Immunol. Mar. 15, 1997;158(6):2723-2730.

Shetron-Rama et al., Isolation of Listeria monocytogenes mutants with high-level in vitro expression of host cytosol-induced gene products. Mol Microbiol. Jun. 2003;48(6):1537-1551.

Shigemasa et al., Expression of the protease inhibitor antileukoprotease and the serine protease stratum corneum ahymotryptic enzyme (SCCE) is coordinated in ovarian tumors. Int J Gynecol Cancer. Nov.-Dec. 2001;11(6):454-461.

Shirakawa et al., A Cox-2 Promoter-Based Replication-Selective Adenoviral Vector to Target the Cox-2-Expressing Human Bladder Cancer Cells. Clin Cancer Res. Jul. 1, 2004;10(13):4342-4348.

Shirasawa et al., Receptor for advanced glycation end-products is a marker of type I lung alveolar cells. Genes Cells. Feb. 2004;9(2):165-174.

Shivapurkar et al., Presence of Simian Virus 40 DNA Sequences in Human Lymphoid and Hematopoietic Malignancies and Their Relationship to Aberrant Promoter Methylation of Multiple Genes. Cancer Res. Jun. 1, 2004;64 (11):3757-3760.

Siegel et al., Induction of antitumour immunity using survivin peptide-pulsed dendritic cells in a murine lymphoma model. Br J Haematol. Sep. 2003;122(6):911-914.

Simon et al., Cervical response to vaccination against HPV16 E7 in case of severe dysplasia. Eur J Obstet Gynecol Reprod Biol. Aug. 15, 2003;109(2):219-223.

Sjolander et al., Serological divergence of Dobrava and Saaremaa hantaviruses: evidence for two distinct serotypes. Epidemiol Infect. Feb. 2002;128(1):99-103.

Skoble et al., Three Regions within ActA Promote Arp2/3 Complex-Mediated Actin Nucleation and Listeria monocytogenes Motility. J Cell Biol. Aug. 7, 2000;150(3):527-538.

Slager et al., Identification of Multiple HLA-DR-Restricted Epitopes of the Tumor-Associated Antigen CAMEL by CD4+ Th1/Th2 Lymphocytes. J Immunol. Apr. 15, 2004;172(8):5095-5102.

\* cited by examiner

ActANterm variants:

| | 1 | 10 | 20 | 30 | 40 | 50 | 60 | 70 | 80 | 90 | 102 |
|---|---|---|---|---|---|---|---|---|---|---|---|
| WT | (1) | VGLNRFMRAMMVVFITANCITINPDIIFAATDSEDSSLNTDEWEEEKTEEQPSEVNTGPRYETAREVSSRDIEELEKSNKVKNTNKADLIAMLKAKAEKGGS |
| dIPEST | (1) | VGLNRFMRAMMVVFITANCITINPDIIFAATDSEDSSLNTDEWEEE----------------RYETAREVSSRDIEELEKSNKVKNTNKADLIAMLKAKAEKGGS |
| dIPESTqdnkr | (1) | VGLNRFMRAMMVVFITANCITINPDIIFAATDSEDSSLNTDEWEEE----------------RYETAREVSSRDIEELEKSNKVKNTNKADQNRKAKAEKGGS |
| qdnkr | (1) | VGLNRFMRAMMVVFITANCITINPDIIFAATDSEDSSLNTDEWEEEKTEEQPSEVNTGPRYETAREVSSRDIEELEKSNKVKNTNKADQNRKAKAEKGGS |
| BH1193 | (1) | VGLNRFMRAMMVVFITANCITINPDIIFAATDSEDSSLNTDEWEEE----------------RYETAREVSSRDIEELEKSNKVKNTNKADLIAMLKAKAEKGGS |
| PL910 | (1) | VGLNRFMRAMMVVFITANCITINPDIIFAATDSEDSSLNTDEWEEE----------------RYETAREVSSRDIEELEKSNKVKNTNKADLIAMLKAKAEKGGS |
| PL995 | (1) | VGLNRFMRAMMVVFITANCITINPDIIFAATDSEDSSLNTDEWEEEKTEEQPSEVNTGPRYETAREVSSRDIEELEKSNKVKNTNKADQNRKAKAEKGGS |
| PL997 | (1) | VGLNRFMRAMMVVFITANCITINPDIIFAATDSEDSSLNTDEWEEEKTEEQPSEVNTGPRYETAREVSSRDIEELEKSNKVKNTNKADQNRKAKAEKGGS |

LLO Nterm variants:

| | 1 | 10 | 20 | 30 | 40 | 50 | 60 | 70 | 80 | 90 | 100 |
|---|---|---|---|---|---|---|---|---|---|---|---|
| LLO WT | (1) | MKKIMLVFITLILVSLPIAQQTEAKDASAFNKENSISSMAPPASPPASPKTPIEKKHADEIDKYIQGLDYNKNNVLVYHGDAVTNVPPRKGYKDGNEYIV |
| LLO dI26 | (1) | MKKIMLVFITLILVSLPIAQQTEAKDASAFNKE--------------------------EIDKYIQGLDYNKNNVLVYHGDAVTNVPPRKGYKDGNEYIV |
| LLO dIPEST | (1) | MKKIMLVFITLILVSLPIAQQTEAKDASAFN---------------------TPIEKKHADEIDKYIQGLDYNKNNVLVYHGDAVTNVPPRKGYKDGNEYIV |
| LLOopt | (1) | MKKIMLVFITLILVSLPIAQQTEAKDASAFNKENSISSMAPPASPPASPKTPIEKKHADEIDKYIQGLDYNKNNVLVYHGDAVTNVPPRKGYKDGNEYIV |
| PL1007 | (1) | MKKIMLVFITLILVSLPIAQQTEAKDASAFNKENSISSMAPPASPPASPKTPIEKKHADEIDKYIQGLDYNKNNVLVYHGDAVTNVPPRKGYKDGNEYIV |
| PL1009 | (1) | MKKIMLVFITLILVSLPIAQQTEAKDASAFNKE--------------------------EIDKYIQGLDYNKNNVLVYHGDAVTNVPPRKGYKDGNEYIV |
| PL1011 | (1) | MKKIMLVFITLILVSLPIAQQTEAKDASAFN---------------------TPIEKKHADEIDKYIQGLDYNKNNVLVYHGDAVTNVPPRKGYKDGNEYIV |
| PL1013 | (1) | MKKIMLVFITLILVSLPIAQQTEAKDASAFN---------------------TPIEKKHADEIDKYIQGLDYNKNNVLVYHGDAVTNVPPRKGYKDGNEYIV |

FIG. 2

| Strain | Construct |
|---|---|
| BH137 | ActAN100-OVA positive control |
| Lm11 | negative control |
| BH1193 | ActAN100-HIVgagB-SL8 |
| PL910 | ActAN100ΔP-HIVgagB-SL8 |
| PL995 | ActAN100ΔP-QDNKR-HIVgagB-SL8 |
| PL997 | ActAN100-QDNKR-HIVgagB-SL8 |
| PL1007 | hlyp-LLO$_{441}$WT-A18K-HIVgagB-SL8 |
| PL1009 | hlyp-LLO$_{441}$Δ26-A18K-HIVgagB-SL8 |
| PL1011 | hlyp-LLO$_{441}$ΔPEST-A18K-HIVgagB-SL8 |

```
WT ActA:      LNTDEWEEEKTEEQPSEVNTGPRYETAREVSSR
Mutant 40:    LNTDEWAAAATAAQPSAVNTGPRYETAREVSSR
ΔP:           LNTDEWEEE------A-------YETAREVSSR
"RKR":        LNTDEWEEEKRKRQRKRVNRGKRYETAREVSSR
"KRK":
     LNTDEWEEEKRKRQRKRVNRGKRYETAREVSSRLNTDEWEEEKKRKQKR
KVNKGRRYETAREVSSR
```

FIG. 7

- △ — 1x10⁵ cfu Lm ΔactA ΔinlB
- ● — 1x10⁵ cfu ActAN100–mesothelin
- ○ — 1x10⁴ cfu ActAN100–mesothelin
- ■ — 1x10⁵ cfu ActAN100*–mesothelin
- □ — 1x10⁴ cfu ActAN100*–mesothelin

FIG.9

SIGNAL PEPTIDE FUSION PARTNERS FACILITATING LISTERIAL EXPRESSION OF ANTIGENIC SEQUENCES AND METHODS OF PREPARATION AND USE THEREOF

The present invention claims priority to U.S. Provisional Patent Application 61/746,237, filed Dec. 27, 2012, and to U.S. Provisional Patent Application 61/780,744, filed Mar. 13, 2013, each of which is hereby incorporated by reference in its entirety including all tables, figures and claims.

SEQUENCE LISTING

The instant application contains a Sequence Listing which has been submitted electronically in ASCII format and is hereby incorporated by reference in its entirety. Said ASCII copy, created on Feb. 14, 2014, is named ANZ9000UT_SL.txt and is 40,635 bytes in size.

BACKGROUND OF THE INVENTION

The following discussion of the background of the invention is merely provided to aid the reader in understanding the invention and is not admitted to describe or constitute prior art to the present invention.

*Listeria monocytogenes* (Lm) is a facultative intracellular bacterium characterized by its ability to induce a profound innate immune response that leads to robust and highly functional CD4 and CD8 T cell immunity specific for vaccine-encoded Ags. Lm is a food-borne bacterium with increased pathogenicity among immune compromised individuals, including patients with cancer or other viral-induced immune deficiencies, pregnant women, the elderly and infants.

Recombinantly modified Lm vaccine platforms engineered to encode a designated antigen(s) relevant to a selected targeted pathogenic agent or malignancy have formed the basis for several human clinical trials. As *Listeria* can be a pathogenic organism, and particularly in the immunocompromised, it is preferred that the administration step comprises administering an attenuated *Listeria* that encodes an expressible, immunologically active portion of an antigen of interest. "Attenuation" refers to a process by which a bacterium is modified to lessen or eliminate its pathogenicity, but retains its ability to act as a prophylactic or therapeutic for the disease of interest. By way of example, genetically defined live-attenuated Lm ΔactAΔinlB, which is deleted of two virulence genes and is attenuated >3 logs in the mouse listeriosis model, retains its immunologic potency and has been shown to induce robust CD4 and CD8 T cell immunity in both mouse models of human disease as well as in humans, and has been shown to be safe and well-tolerated in clinical settings among patients with various solid tumor malignancies.

*Listeria* strains have been most commonly engineered to secrete a tumor antigen as a fusion with all or a portion of a secreted Listerial protein, such as listeriolysin O (LLO) or ActA. It has been suggested that a possible reason for the efficacy of such vaccine constructs may be the presence of amino acid sequences within LLO and ActA called "PEST" motifs. PEST regions (P, proline; E, glutamic acid; S, serine; T, threonine) are hydrophilic amino acid sequences that reside near the NH2 or COOH termini of certain proteins. They are thought to target proteins for rapid degradation by the cellular proteasome. To be recognized by T lymphocytes, protein antigens must be converted into short peptides bound to MHC molecules, which are displayed on the surface of antigen presenting cells. And, indeed, the PEST region of LLO has been suggested to be crucial to the success of Listerial vaccines, as the supply of peptides available for presentation by MHC class I molecules can be increased by shortening the cellular half-life of a protein.

BRIEF SUMMARY OF THE INVENTION

The present invention provides nucleic acids, expression systems, and vaccine strains which provide efficient expression and secretion of antigens of interest into the cytosol of host cells, and elicit effective CD4 and CD8 T cell responses by functionally linking Listerial or other bacterial signal peptides/secretion chaperones as N-terminal fusion partners in translational reading frame with selected recombinant encoded protein antigens. These bacterial N-terminal signal peptide/secretion chaperone fusion partners direct the secretion of the synthesized fusion protein from the recombinant bacterium in the infected host mammalian cells. As described hereinafter, these N-terminal fusion partners are deleted (either by actual deletion, by mutation, or by a combination of these approaches) for any PEST sequences native to the sequence.

The bacterial N-terminal signal peptide/secretion chaperone fusion partners are modified, relative to a native polypeptide sequence, in terms of the modification of PEST sequences, and also optionally in terms of length and/or the existence of hydrophobic motifs outside the signal sequence. By way of example, ActA may be truncated to delete the C-terminal membrane-binding domain, and in certain embodiments even further to decrease the number of non-antigenic residues in the fusion protein. In addition, one or more hydrophobic residues in these N-terminal fusion partners which are not part of the signal sequence and which form a hydrophobic motif in the polypeptide sequence are also deleted (again, either by actual deletion, by mutation, or by a combination of these approaches). The resulting fusion proteins are expressed at high levels and generate a robust immunologic response to the antigen(s) of interest which are contained in the fusion protein.

In a first aspect, the present invention relates to polynucleotides comprising:
(a) a promoter; and
(b) a nucleic acid operably linked to the promoter, wherein the nucleic acid encodes a fusion protein comprising:
 a polypeptide derived by recombinant modification of a secreted Listerial protein sequence, the secreted Listerial protein sequence in its unmodified form comprising a signal sequence and one or more PEST motifs, the modification comprising removal of each of the PEST motifs by deletion or substitution by one or more residues such that the polypeptide lacks any PEST motif; and
 a non-Listerial antigen.

In certain embodiments, the N-terminal signal peptide/secretion chaperone fusion partner is derived from ActA or LLO. One or more P, E, S, and T residues, and preferably each P, E, S, and T residue, in the PEST motif of an ActA or LLO polypeptide sequence may be substituted with a residue other than P, E, S, and T. As described hereinafter, even removal of a single residue can render this motif less "PEST-like." Alternatively, one or more P, E, S, and T residues, and preferably each P, E, S, and T residue, in the PEST motif of an ActA or LLO polypeptide sequence may simply be deleted. By way of example, each P, E, S, and T residue in the PEST motif may be substituted with K or R.

The derived polypeptide most preferably retains the signal sequence of the secreted Listerial protein sequence (e.g., ActA or LLO) in unmodified form.

In the case where the secreted Listerial protein sequence is an ActA sequence, at least 75% of the PEST motif KTEEQPSEVNTGP (SEQ ID NO: 1) is preferably deleted. In certain preferred embodiments, the sequence KTEEQPSEVNTGP (SEQ ID NO: 1) or KTEEQPSEVNTGPR (SEQ ID NO: 2) is deleted. In the case where the secreted Listerial protein sequence is an LLO sequence, at least 75% of the the PEST motif KENSISSMAPPASPPASPK (SEQ ID NO: 6) is preferably deleted. In certain preferred embodiments, the sequence KENSISSMAPPASPPASPK (SEQ ID NO: 6) or NSISSMAPPASPPASPKTPIEKKHAD (SEQ ID NO: 7) is preferably deleted.

Optionally, a sequence which forms a hydrophobic motif may be substituted with one or more amino acids which are not hydrophobic. Thus, modification of the N-terminal signal peptide/secretion chaperone fusion partner may further comprise removal of one or more hydrophobic domains which are not part of the signal sequence of the secreted Listerial protein sequence; and/or substitution of one or more residues within one or more hydrophobic domains which are not part of the signal sequence of the secreted Listerial protein sequence with amino acids which are not hydrophobic. By way of example described below, the sequence LIAML (SEQ ID NO: 8) in ActA may be replaced with the sequence QDNKR (SEQ ID NO: 9).

As described herein, the N-terminal signal peptide/secretion chaperone fusion partner is optionally truncated relative to the native length of the parent protein (e.g., ActA or LLO). By way of example, ActA may be truncated to delete the C-terminal membrane-binding domain, and in certain embodiments even further, to decrease the number of non-antigenic residues in the fusion protein. Similarly, LLO may be truncated prior to about residue 484 in order to abrogate cholesterol binding, and in certain embodiments even further, to again decrease the number of non-antigenic residues in the fusion protein.

In preferred embodiments, the secreted Listerial protein sequence is drived from an ActA sequence and the polypeptide comprises at least the first 95 residues of one of the sequences referred to as dlPEST and dlPEST qdnkr (SEQ ID NO: 9) in FIG. 2.

In preferred embodiments, the secreted Listerial protein sequence is drived from an LLO sequence and the polypeptide comprises at least the first 95 residues of one of the sequences referred to as LLO dlPEST and LLO dl26 in FIG. 2.

In certain embodiments, the promoter provides regulatory sequences which induce expression of the fusion protein in a host cell upon introduction of the bacterium into a host organism. By way of example only, the promoter is a *Listeria monocytogenes* promoter which is PrfA-dependent. PrfA-dependent promoters may be selected from the group consisting of the inlA promoter, the inlB promoter, the inlC promoter, the hpt promoter, the hly promoter, the plcA promoter, the mpl promoter, and the actA promoter.

The non-Listerial antigen portion of the fusion protein of the present invention comprises one or more sequences selected to induce a desired immune response specific for encoded heterologous antigen(s), i.e., to cause a decrease, prevention, or amelioration of the symptoms of the condition being treated. In certain embodiments, the non-Listerial antigen comprises one or more sequences encoding a cancer cell, tumor, or infectious agent antigen.

In a related aspect, the polynucleotide of the invention is provided as a component of a plasmid, vector, or the like.

In another related aspect, the invention provides a recombinant *Listeria* bacterium modified to comprise the polynucleotide of the invention. In various embodiments, the polynucleotide may be provided episomally, or may be integrated into the bacterial genome. The recombinant *Listeria* bacterium may be further modified so as to be attenuated, for example by a functional deletion of the bacterium's genomic actA and/or inlB genes. In certain embodiments, the polynucleotide of the invention is inserted into the bacterium's genomic actA or inlB gene. The bacterium of the present invention may be utilized as an expression platform for expressing one or more genes which are heterologous to the bacterium, for example for purposes of generating an immune response to the heterologous proteins expressed from those genes. Thus, this aspect can provide a vaccine comprising the recombinant *Listeria* bacterium and a pharmacologically acceptable excipient.

In still another related aspect, the invention provides a method for stimulating an immune response to a non-Listerial antigen in a mammal comprising administering an effective amount of the *Listeria* bacterium described herein to the mammal, wherein the non-Listerial antigen is expressed in one or more cells of the mammal.

BRIEF DESCRIPTION OF THE FIGURES

FIG. 2 depicts various modifications to the sequences of ActA (SEQ ID NOS 29-36, respectively, in order of appearance) and LLO (SEQ ID NOS 37-44, respectively, in order of appearance). "QDNKR" is disclosed as SEQ ID NO: 9.

FIG. 7 depicts several substitutions and deletions for use in deleting the PEST motif, using ActA as a model system (SEQ ID NOS 47-51, respectively, in order of appearance).

FIG. 9 depicts percent survival of animals immunized with *Listeria monocytogenes* expressing fusion constructs having a modified ActAN100 sequence fused to human mesothelin residues 35-621 following a challenge with CT-26 tumor cells.

Figure 12:
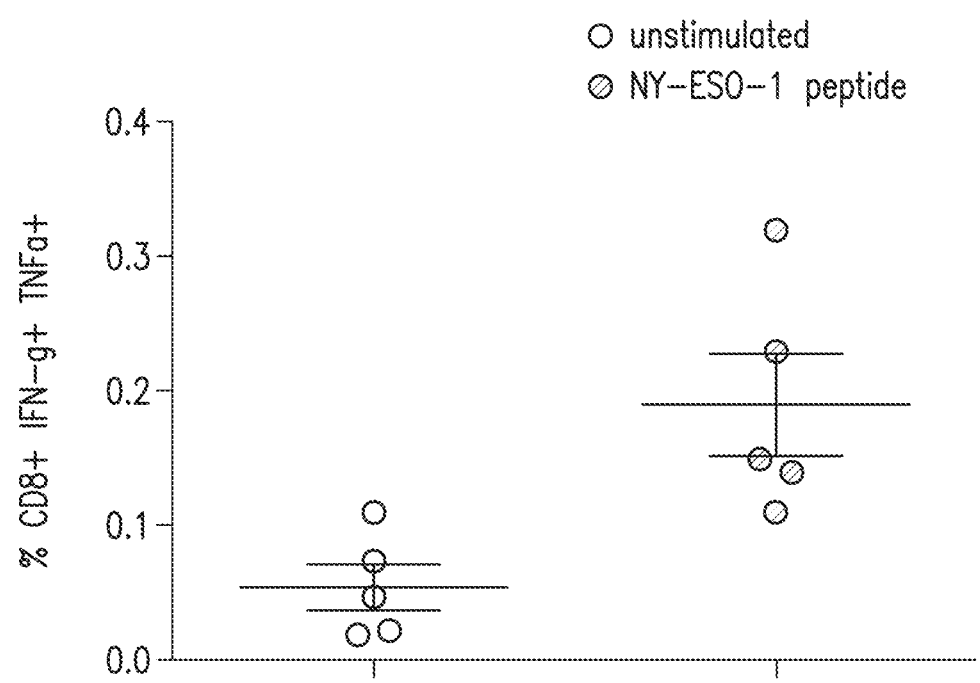

FIG. 12 depicts NY-ESO-1-specific CD8+ T cell responses following immunization with *Listeria monocytogenes* expressing fusion constructs having a modified ActAN100 sequence fused to EGFRvIII$_{20\text{-}40}$/NY-ESO-1$_{1\text{-}165}$.

DETAILED DESCRIPTION OF THE INVENTION

The present invention relates to compositions and methods for preparing antigenic fusion proteins for expression in Listerial bacteria. The present invention can provide attenuated bacterial vaccine strains with advantageous safety profiles for use treatment or prevention of diseases having a risk-benefit profile not appropriate for live attenuated vaccines. While described hereinafter in detail with regard to *Listeria monocytogenes*, the skilled artisan will understand that the methods and compositions described herein are generally applicable to Listerial species.

*Listeria monocytogenes* (Lm) is a facultative intracellular bacterium characterized by its ability to induce a profound innate immune response that leads to robust and highly functional CD4 and CD8 T cell immunity specific for vaccine-encoded Ags. Lm is a food-borne bacterium with increased pathogenicity among immune compromised individuals, including patients with cancer or other viral-induced immune deficiencies, pregnant women, the elderly and infants. To prime a desired CD8 T cell response, Lm-based vaccines must retain the ability to escape from the vacuole of infected dendritic cells (DCs) in a process mediated by expression of a pore-forming cytolysin known as listeriolysin O (LLO), and desired antigens are engineered to be expressed and secreted from bacteria in the cytoplasm, where they are subsequently processed and presented on MHC class I molecules.

There is a certain dichotomy apparent in the development of Lm vaccine strains between antigen expression levels and the requirement for antigen processing. While the immunologic potency of Lm-based vaccines is related directly to the level of antigen expression and secretion in the host cell, efficient MHC class I and class II priming and induction of antigen-specific immune responses has been suggested to depend upon rapid turnover of the antigen by proteolytic machinery of the cell.

Antigen expression cassettes are provided herein which result in efficient expression and secretion of encoded antigens into the cytosol of host cells, and elicit effective CD4 and CD8 T cell responses by functionally linking Listerial or other bacterial signal peptides/secretion chaperones as N-terminal fusion partners in translational reading frame with selected recombinant encoded protein antigens. These bacterial N-terminal signal peptide/secretion chaperone fusion partners direct the secretion of the synthesized fusion protein from the recombinant bacterium in the infected host mammalian cells. As described hereinafter, these N-terminal fusion partners are deleted (either by actual deletion, by mutation, or by a combination of these approaches) for any PEST sequences native to the sequence. Optionally, hydrophobic residues in these N-terminal fusion partners which are not part of the signal sequence are also deleted (again, either by actual deletion, by mutation, or by a combination of these approaches). The resulting fusion proteins are expressed at high levels and generate a robust immunologic response to the antigen(s) of interest which are contained in the fusion protein.

In a preferred embodiment, the said fusion protein is functionally linked to an Lm PrfA-inducible promoter. Preferred non-limiting examples are the hly promoter, which drives the expression of the listeriolysin O (LLO) protein, and the actA promoter, which drives the expression of the ActA protein, respectively, in wild-type *Listeria monocytogenes*. PrfA-dependent promoters are induced within infected mammalian host cells and functionally linked proteins are synthesized at high levels. The temporally regulated high-level expression of encoded fusion proteins comprising selected antigens functionally linked to PrfA-dependent promoters in the host cells facilitates antigen processing and presentation, resulting in an optimal Lm vaccine-induced immune response.

As described hereinafter, preferred non-limiting examples of N-terminal signal peptide/secretion chaperone fusion partners are modified LLO or ActA proteins, derived from *Listeria monocytogenes*. The LLO and ActA N-terminal signal peptide/secretion chaperone fusion partners can be functionally linked to a Listerial PrfA-dependent promoter (e.g., the hly promoter or the actA promoter). In a preferred embodiment, ActA and LLO N-terminal signal peptide/secretion chaperone fusion partners which lack any PEST-like sequence motifs for fusion in frame with any selected antigen sequences are provided. Such PEST-minus N-terminal fusion partners are referred to herein as PEST minus (PEST) ActA and PEST LLO.

Figure 1:
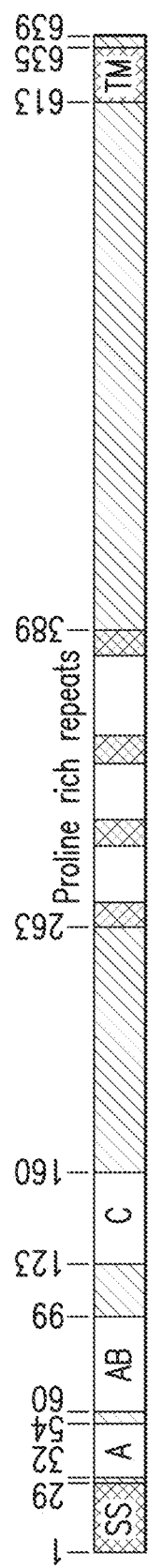
FIG. 1 depicts certain functional attributes of ActA in schematic form.

FIG. 1 depicts in schematic form certain functional attributes of ActA. Underlined regions depict the location of PEST sequences in the native ActA sequence. In certain embodiments, the N-terminal signal peptide/secretion chaperone is derived from ActA in that it comprises the signal sequence of ActA and is truncated at about residue 389 amino acids of ActA in order to delete the C-terminal domain which comprises a transmembrane region. The term "about" as used herein in this context refers to +/−25 amino acid residues.

The term "derived" as used herein with regard to modification of secreted Listerial proteins to provide signal peptides/secretion chaperones for use of N-terminal fusion partners, refers to removal of PEST sequences native to the Listerial protein, and also optionally truncation relative to the native length and/or modification of one or more hydrophobic motifs outside the signal sequence. By way of example, ActA may be truncated to delete the C-terminal membrane-binding domain, and in certain embodiments even further, to decrease the number of non-antigenic residues in the fusion protein. In addition, one or more hydrophobic residues in these N-terminal fusion partners which are not part of the signal sequence and which form a hydrophobic motif in the polypeptide sequence are also deleted (again, either by actual deletion, by mutation, or by a combination of these approaches). As described hereinafter, the resulting fusion proteins are expressed at high levels and generate a robust immunologic response to the antigen(s) of interest which are contained in the fusion protein.

Similarly, native LLO contains 529 residues and comprises a 25 residue signal sequence followed by four structural domains. Domain 4 is roughly from residues 415-529 and contains a cholesterol binding region. Domain 1 contains a single PEST sequence. In certain embodiments, the N-terminal signal peptide/secretion chaperone is derived from LLO in that it comprises the signal sequence of LLO and is truncated prior to about residue 484 in order to abrogate cholesterol binding. The term "derived" as used herein in this context refers to being modified, relative to the native LLO sequence, in terms of length, the existence of PEST sequences, and the existence of hydrophobic motifs outside the signal sequence. Preferably, the modified ActA is truncated at about residue 441.

As demonstrated hereinafter, the PEST sequences and hydrophobic domains may be functionally deleted, either by their removal, or by noon-conservative substitution of residues, or by a combination of these approaches. By way of example only, the following examples demonstrate the replacement of a LIAML (SEQ ID NO: 8) hydrophobic motif in ActA with the sequence QDNKR (SEQ ID NO: 9); and the actual deletion of all or a portion of the ActA PEST sequence.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

1. DEFINITIONS

Abbreviations used to indicate a mutation in a gene, or a mutation in a bacterium comprising the gene, are as follows. By way of example, the abbreviation "*L. monocytogenes* ΔactA" means that part, or all, of the actA gene was deleted. The delta symbol (Δ) means deletion. An abbreviation including a superscripted minus sign (*Listeria* ActA⁻) means that the actA gene was mutated, e.g., by way of a deletion, point mutation, or frameshift mutation, but not limited to these types of mutations.

"Administration" as it applies to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell.

An "agonist," as it relates to a ligand and receptor, comprises a molecule, combination of molecules, a complex, or a combination of reagents, that stimulates the receptor. For example, an agonist of granulocyte-macrophage colony stimulating factor (GM-CSF) can encompass GM-CSF, a mutein or derivative of GM-CSF, a peptide mimetic of GM-CSF, a small molecule that mimics the biological function of GM-CSF, or an antibody that stimulates GM-CSF receptor.

An "antagonist," as it relates to a ligand and receptor, comprises a molecule, combination of molecules, or a complex, that inhibits, counteracts, downregulates, and/or desensitizes the receptor. "Antagonist" encompasses any reagent that inhibits a constitutive activity of the receptor. A constitutive activity is one that is manifest in the absence of a ligand/receptor interaction. "Antagonist" also encompasses any reagent that inhibits or prevents a stimulated (or regulated) activity of a receptor. By way of example, an antagonist of GM-CSF receptor includes, without implying any limitation, an antibody that binds to the ligand (GM-CSF) and prevents it from binding to the receptor, or an antibody that binds to the receptor and prevents the ligand from binding to the receptor, or where the antibody locks the receptor in an inactive conformation.

As used herein, an "analog" or "derivative" with reference to a peptide, polypeptide or protein refers to another peptide, polypeptide or protein that possesses a similar or identical function as the original peptide, polypeptide or protein, but does not necessarily comprise a similar or identical amino acid sequence or structure of the original peptide, polypeptide or protein. An analog preferably satisfies at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the original amino acid sequence (b) a proteinaceous agent encoded by a nucleotide sequence that hybridizes under stringent conditions to a nucleotide sequence encoding the original amino acid sequence; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding the original amino acid sequence.

"Antigen presenting cells" (APCs) are cells of the immune system used for presenting antigen to T cells. APCs include dendritic cells, monocytes, macrophages, marginal zone Kupffer cells, microglia, Langerhans cells, T cells, and B cells. Dendritic cells occur in at least two lineages. The first lineage encompasses pre-DC1, myeloid DC1, and mature DC1. The second lineage encompasses CD34$^+$ CD45RA$^-$ early progenitor multipotent cells, CD34$^+$ CD45RA$^+$ cells, CD34$^+$CD45RA$^+$CD4$^+$ IL-3Rα$^+$ pro-DC2 cells, CD4$^+$CD11c$^-$ plasmacytoid pre-DC2 cells, lymphoid human DC2 plasmacytoid-derived DC2s, and mature DC2s.

"Attenuation" and "attenuated" encompasses a bacterium, virus, parasite, infectious organism, prion, tumor cell, gene in the infectious organism, and the like, that is modified to reduce toxicity to a host. The host can be a human or animal host, or an organ, tissue, or cell. The bacterium, to give a non-limiting example, can be attenuated to reduce binding to a host cell, to reduce spread from one host cell to another host cell, to reduce extracellular growth, or to reduce intracellular growth in a host cell. Attenuation can be assessed by measuring, e.g., an indicum or indicia of toxicity, the LD$_{50}$, the rate of clearance from an organ, or the competitive index (see, e.g., Auerbuch, et al. (2001) Infect. Immunity 69:5953-5957). Generally, an attenuation results an increase in the LD$_{50}$ and/or an increase in the rate of clearance by at least 25%; more generally by at least 50%; most generally by at least 100% (2-fold); normally by at least 5-fold; more normally by at least 10-fold; most normally by at least 50-fold; often by at least 100-fold; more often by at least 500-fold; and most often by at least 1000-fold; usually by at least 5000-fold; more usually by at least 10,000-fold; and most usually by at least 50,000-fold; and most often by at least 100,000-fold.

"Attenuated gene" encompasses a gene that mediates toxicity, pathology, or virulence, to a host, growth within the host, or survival within the host, where the gene is mutated in a way that mitigates, reduces, or eliminates the toxicity, pathology, or virulence. The reduction or elimination can be assessed by comparing the virulence or toxicity mediated by the mutated gene with that mediated by the non-mutated (or parent) gene. "Mutated gene" encompasses deletions, point mutations, and frameshift mutations in regulatory regions of the gene, coding regions of the gene, non-coding regions of the gene, or any combination thereof.

"Conservatively modified variants" applies to both amino acid and nucleic acid sequences. With respect to particular nucleic acid sequences, a conservatively modified variant refers to nucleic acids encoding identical amino acid sequences, or amino acid sequences that have one or more conservative substitutions. An example of a conservative substitution is the exchange of an amino acid in one of the following groups for another amino acid of the same group (U.S. Pat. No. 5,767,063 issued to Lee, et al.; Kyte and Doolittle (1982) J. Mol. Biol. 157:105-132). Conversely, a non-conservative substitution is the exchange of an amino acid in one of the following groups for another amino acid of a different group.
(1) Hydrophobic: Norleucine, Ile, Val, Leu, Phe, Cys, Met;
(2) Neutral hydrophilic: Cys, Ser, Thr;
(3) Acidic: Asp, Glu;
(4) Basic: Asn, Gln, His, Lys, Arg;
(5) Residues that influence chain orientation: Gly, Pro;
(6) Aromatic: Trp, Tyr, Phe; and
(7) Small amino acids: Gly, Ala, Ser.

"Effective amount" encompasses, without limitation, an amount that can ameliorate, reverse, mitigate, prevent, or diagnose a symptom or sign of a medical condition or disorder. Unless dictated otherwise, explicitly or by context, an "effective amount" is not limited to a minimal amount sufficient to ameliorate a condition.

An "extracellular fluid" encompasses, e.g., serum, plasma, blood, interstitial fluid, cerebrospinal fluid, secreted fluids, lymph, bile, sweat, fecal matter, and urine. An "extracelluar fluid" can comprise a colloid or a suspension, e.g., whole blood or coagulated blood.

The term "fragments" in the context of polypeptides include a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a larger polypeptide.

"Gene" refers to a nucleic acid sequence encoding an oligopeptide or polypeptide. The oligopeptide or polypeptide can be biologically active, antigenically active, biologically inactive, or antigenically inactive, and the like. The term gene encompasses, e.g., the sum of the open reading frames (ORFs) encoding a specific oligopeptide or polypeptide; the sum of the ORFs plus the nucleic acids encoding introns; the sum of the ORFs and the operably linked promoter(s); the sum of the ORFS and the operably linked promoter(s) and any introns; the sum of the ORFS and the operably linked promoter(s), intron(s), and promoter(s), and other regulatory elements, such as enhancer(s). In certain embodiments, "gene" encompasses any sequences required in cis for regulating expression of the gene. The term gene can also refer to a nucleic acid that encodes a peptide encompassing an antigen or an antigenically active fragment of a peptide, oligopeptide, polypeptide, or protein. The term gene does not necessarily imply that the encoded peptide or protein has any biological activity, or even that the peptide or protein is antigenically active. A nucleic acid sequence encoding a non-expressable sequence is generally considered a pseudogene. The term gene also encompasses nucleic acid sequences encoding a ribonucleic acid such as rRNA, tRNA, or a ribozyme.

"Growth" of a bacterium such as *Listeria* encompasses, without limitation, functions of bacterial physiology and genes relating to colonization, replication, increase in protein content, and/or increase in lipid content. Unless specified otherwise explicitly or by context, growth of a *Listeria* encompasses growth of the bacterium outside a host cell, and also growth inside a host cell. Growth related genes include, without implying any limitation, those that mediate energy production (e.g., glycolysis, Krebs cycle, cytochromes), anabolism and/or catabolism of amino acids, sugars, lipids, minerals, purines, and pyrimidines, nutrient transport, transcription, translation, and/or replication. In some embodiments, "growth" of a *Listeria* bacterium refers to intracellular growth of the *Listeria* bacterium, that is, growth inside a host cell such as a mammalian cell. While intracellular growth of a *Listeria* bacterium can be measured by light microscopy or colony forming unit (CFU) assays, growth is not to be limited by any technique of measurement. Biochemical parameters such as the quantity of a Listerial antigen, Listerial nucleic acid sequence, or lipid specific to the *Listeria* bacterium, can be used to assess growth. In some embodiments, a gene that mediates growth is one that specifically mediates intracellular growth. In some embodiments, a gene that specifically mediates intracellular growth encompasses, but is not limited to, a gene where inactivation of the gene reduces the rate of intracellular growth but does not detectably, substantially, or appreciably, reduce the rate of extracellular growth (e.g., growth in broth), or a gene where inactivation of the gene reduces the rate of intracellular growth to a greater extent than it reduces the rate of extracellular growth. To provide a non-limiting example, in some embodiments, a gene where inactivation reduces the rate of intracellular growth to a greater extent than extracellular growth encompasses the situation where inactivation reduces intracellular growth to less than 50% the normal or maximal value, but reduces extracellular growth to only 1-5%, 5-10%, or 10-15% the maximal value. The invention, in certain aspects, encompasses a *Listeria* attenuated in intracellular growth but not attenuated in extracellular growth, a *Listeria* not attenuated in intracellular growth and not attenuated in extracellular growth, as well as a *Listeria* not attenuated in intracellular growth but attenuated in extracellular growth.

A composition that is "labeled" is detectable, either directly or indirectly, by spectroscopic, photochemical, biochemical, immunochemical, isotopic, or chemical methods.

For example, useful labels include $^{32}P$, $^{33}P$, $^{35}S$, $^{14}C$, $^{3}H$, $^{125}I$, stable isotopes, epitope tags, fluorescent dyes, electron-dense reagents, substrates, or enzymes, e.g., as used in enzyme-linked immunoassays, or fluorettes (see, e.g., Rozinov and Nolan (1998) Chem. Biol. 5:713-728).

"Hydrophobic motif" as used herein refers to a set of contuinguous amino acid residues which, in the context of the entire protein of which they are a part, exhibit a hydrophobic character by hydropathy analysis. A "hydropathy analysis" refers to the analysis of a polypeptide sequence by the method of Kyte and Doolittle: "A Simple Method for Displaying the Hydropathic Character of a Protein". J. Mol. Biol. 157 (1982)105-132. In this method, each amino acid is given a hydrophobicity score between 4.6 and –4.6. A score of 4.6 is the most hydrophobic and a score of –4.6 is the most hydrophilic. Then a window size is set. A window size is the number of amino acids whose hydrophobicity scores will be averaged and assigned to the first amino acid in the window. The calculation starts with the first window of amino acids and calculates the average of all the hydrophobicity scores in that window. Then the window moves down one amino acid and calculates the average of all the hydrophobicity scores in the second window. This pattern continues to the end of the protein, computing the average score for each window and assigning it to the first amino acid in the window. The averages are then plotted on a graph. The y axis represents the hydrophobicity scores and the x axis represents the window number. The following hydrophobicity scores are used for the 20 common amino acids.

| Arg: | −4.5 | Ser: | −0.8 | Lys: | −3.9 |
|------|------|------|------|------|------|
| Thr: | −0.7 | Asn: | −3.5 | Gly: | −0.4 |
| Asp: | −3.5 | Ala: | 1.8  | Gln: | −3.5 |
| Met: | 1.9  | Glu: | −3.5 | Cys: | 2.5  |
| His: | −3.2 | Phe: | 2.8  | Pro: | −1.6 |
| Leu: | 3.8  | Tyr: | −1.3 | Val: | 4.2  |
| Trp: | −0.9 | Ile: | 4.5  |      |      |

"Ligand" refers to a small molecule, peptide, polypeptide, or membrane associated or membrane-bound molecule which is an agonist or antagonist of a receptor. "Ligand" also encompasses a binding agent that is not an agonist or antagonist, and has no agonist or antagonist properties. By convention, where a ligand is membrane-bound on a first cell, the receptor usually occurs on a second cell. The second cell may have the same identity (the same name), or it may have a different identity (a different name), as the first cell. A ligand or receptor may be entirely intracellular, that is, it may reside in the cytosol, nucleus, or in some other intracellular compartment. The ligand or receptor may change its location, e.g., from an intracellular compartment to the outer face of the plasma membrane. The complex of a ligand and receptor is termed a "ligand receptor complex." Where a ligand and receptor are involved in a signaling pathway, the ligand occurs at an upstream position and the receptor occurs at a downstream position of the signaling pathway.

"Nucleic acid" refers to deoxyribonucleotides or ribonucleotides and polymers thereof in either single stranded, double-stranded form, or multi-stranded form. Non-limiting examples of a nucleic acid are a, e.g., cDNA, mRNA, oligonucleotide, and polynucleotide. A particular nucleic acid sequence can also implicitly encompasses "allelic variants" and "splice variants."

"Operably linked" in the context of a promoter and a nucleic acid encoding a mRNA means that the promoter can be used to initiate transcription of that nucleic acid.

The terms "percent sequence identity" and "% sequence identity" refer to the percentage of sequence similarity found by a comparison or alignment of two or more amino acid or nucleic acid sequences. Percent identity can be determined by a direct comparison of the sequence information between two molecules by aligning the sequences, counting the exact number of matches between the two aligned sequences, dividing by the length of the shorter sequence, and multiplying the result by 100. An algorithm for calculating percent identity is the Smith-Waterman homology search algorithm (see, e.g., Kann and Goldstein (2002) Proteins 48:367-376; Arslan, et al. (2001) Bioinformatics 17:327-337).

By "purified" and "isolated" is meant, when referring to a polypeptide, that the polypeptide is present in the substantial absence of the other biological macromolecules with which it is associated in nature. The term "purified" as used herein means that an identified polypeptide often accounts for at least 50%, more often accounts for at least 60%, typically accounts for at least 70%, more typically accounts for at least 75%, most typically accounts for at least 80%, usually accounts for at least 85%, more usually accounts for at least 90%, most usually accounts for at least 95%, and conventionally accounts for at least 98% by weight, or greater, of the polypeptides present. The weights of water, buffers, salts, detergents, reductants, protease inhibitors, stabilizers (including an added protein such as albumin), and excipients, and molecules having a molecular weight of less than 1000, are generally not used in the determination of polypeptide purity. See, e.g., discussion of purity in U.S. Pat. No. 6,090,611 issued to Covacci, et al.

"Peptide" refers to a short sequence of amino acids, where the amino acids are connected to each other by peptide bonds. A peptide may occur free or bound to another moiety, such as a macromolecule, lipid, oligo- or polysaccharide, and/or a polypeptide. Where a peptide is incorporated into a polypeptide chain, the term "peptide" may still be used to refer specifically to the short sequence of amino acids. A "peptide" may be connected to another moiety by way of a peptide bond or some other type of linkage. A peptide is at least two amino acids in length and generally less than about 25 amino acids in length, where the maximal length is a function of custom or context. The terms "peptide" and "oligopeptide" may be used interchangeably.

"PEST motifs" are defined herein as hydrophilic stretches of at least 12 amino acids length with a high local concentration of P, E, S and T amino acids, and which score as a valid PEST motif according to the epestfind algorithm. Negatively charged amino acids are clustered within these motifs while positively charged amino acids, arginine (R), histidine (H) and lysine (K) are generally forbidden. The epestfind algorithm defines the last criterion even more stringently in that PEST motifs are required to be flanked by positively charged amino acids. All amino acids between the positively charged flanks are counted and only those motifs are considered further, which contain a number of amino acids equal to or higher than the window-size parameter. Additionally, all 'valid' PEST regions are required to contain at least one proline (P), one aspartate (D) or glutamate (E) and at least one serine (S) or threonine (T). Sequences that do not meet the above criteria are classified as 'invalid' PEST motifs.

"Valid" PEST motifs are refined by means of a scoring parameter based on the local enrichment of critical amino acids as well as the motifs hydrophobicity. Enrichment of D, E, P, S and T is expressed in mass percent (w/w) and corrected for one equivalent of D or E, one of P and one of S or T. Calculation of hydrophobicity follows in principle the method of J. Kyte and R. F. Doolittle. For simplified calculations, Kyte-Doolittle hydropathy indices, which originally ranged from −4.5 for arginine to +4.5 for isoleucine, were converted to positive integers. This was achieved by the following linear transformation, which yielded values from 0 for arginine to 90 for isoleucine.

Hydropathy index=10*Kyte-Doolittle hydropathy index+45

The motifs hydrophobicity is calculated as the sum over the products of mole percent and hydrophobicity index for each amino acid species. The desired PEST score is obtained as combination of local enrichment term and hydrophobicity term as expressed by the following equation:

PEST score=0.55*DEPST−0.5*hydrophobicity index.

In addition, the epestfind algorithm includes a correction for the hydropathy index of tyrosine, introduced by Robert H. Stellwagen from the University of Southern California. However, PEST scores can range from −45 for poly-isoleucine to about +50 for poly-aspartate plus one proline and one serine. 'Valid' PEST motifs are those above the threshold score of 5.0 and are considered of real biological interest.

"Protein" generally refers to the sequence of amino acids comprising a polypeptide chain. Protein may also refer to a three dimensional structure of the polypeptide. "Denatured protein" refers to a partially denatured polypeptide, having some residual three dimensional structure or, alternatively, to an essentially random three dimensional structure, i.e., totally denatured. The invention encompasses reagents of, and methods using, polypeptide variants, e.g., involving glycosylation, phosphorylation, sulfation, disulfide bond formation, deamidation, isomerization, cleavage points in signal or leader sequence processing, covalent and non-covalently bound cofactors, oxidized variants, and the like. The formation of disulfide linked proteins is described (see, e.g., Woycechowsky and Raines (2000) Curr. Opin. Chem. Biol. 4:533-539; Creighton, et al. (1995) Trends Biotechnol. 13:18-23).

"Recombinant" when used with reference, e.g., to a nucleic acid, cell, animal, virus, plasmid, vector, or the like, indicates modification by the introduction of an exogenous, non-native nucleic acid, alteration of a native nucleic acid, or by derivation in whole or in part from a recombinant nucleic acid, cell, virus, plasmid, or vector. Recombinant protein refers to a protein derived, e.g., from a recombinant nucleic acid, virus, plasmid, vector, or the like. "Recombinant bacterium" encompasses a bacterium where the genome is engineered by recombinant methods, e.g., by way of a mutation, deletion, insertion, and/or a rearrangement. "Recombinant bacterium" also encompasses a bacterium modified to include a recombinant extra-genomic nucleic acid, e.g., a plasmid or a second chromosome, or a bacterium where an existing extra-genomic nucleic acid is altered.

"Sample" refers to a sample from a human, animal, placebo, or research sample, e.g., a cell, tissue, organ, fluid, gas, aerosol, slurry, colloid, or coagulated material. The "sample" may be tested in vivo, e.g., without removal from the human or animal, or it may be tested in vitro. The sample may be tested after processing, e.g., by histological methods. "Sample" also refers, e.g., to a cell comprising a fluid or tissue sample or a cell separated from a fluid or tissue sample. "Sample" may also refer to a cell, tissue, organ, or fluid that is freshly taken from a human or animal, or to a cell, tissue, organ, or fluid that is processed or stored.

A "selectable marker" encompasses a nucleic acid that allows one to select for or against a cell that contains the selectable marker. Examples of selectable markers include, without limitation, e.g.: (1) A nucleic acid encoding a product providing resistance to an otherwise toxic compound (e.g., an antibiotic), or encoding susceptibility to an otherwise harmless compound (e.g., sucrose); (2) A nucleic acid encoding a product that is otherwise lacking in the recipient cell (e.g., tRNA genes, auxotrophic markers); (3) A nucleic acid encoding a product that suppresses an activity of a gene product; (4) A nucleic acid that encodes a product that can be readily identified (e.g., phenotypic markers such as beta-galactosidase, green fluorescent protein (GFP), cell surface proteins, an epitope tag, a FLAG tag); (5) A nucleic acid that can be identified by hybridization techniques, for example, PCR or molecular beacons.

"Specifically" or "selectively" binds, when referring to a ligand/receptor, nucleic acid/complementary nucleic acid, antibody/antigen, or other binding pair (e.g., a cytokine to a cytokine receptor) indicates a binding reaction which is determinative of the presence of the protein in a heterogeneous population of proteins and other biologics. Thus, under designated conditions, a specified ligand binds to a particular receptor and does not bind in a significant amount to other proteins present in the sample. Specific binding can also mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with any other binding compound.

In a typical embodiment an antibody will have an affinity that is greater than about $10^9$ liters/mol, as determined, e.g., by Scatchard analysis (Munsen, et al. (1980) Analyt. Biochem. 107:220-239). It is recognized by the skilled artisan that some binding compounds can specifically bind to more than one target, e.g., an antibody specifically binds to its antigen, to lectins by way of the antibody's oligosaccharide, and/or to an Fc receptor by way of the antibody's Fc region.

"Spread" of a bacterium encompasses "cell to cell spread," that is, transmission of the bacterium from a first host cell to a second host cell, as mediated, for example, by a vesicle. Functions relating to spread include, but are not limited to, e.g., formation of an actin tail, formation of a pseudopod-like extension, and formation of a double-membraned vacuole.

The term "subject" as used herein refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology.

The "target site" of a recombinase is the nucleic acid sequence or region that is recognized, bound, and/or acted upon by the recombinase (see, e.g., U.S. Pat. No. 6,379,943 issued to Graham, et al.; Smith and Thorpe (2002) Mol. Microbiol. 44:299-307; Groth and Calos (2004) J. Mol. Biol. 335:667-678; Nunes-Duby, et al. (1998) Nucleic Acids Res. 26:391-406).

"Therapeutically effective amount" is defined as an amount of a reagent or pharmaceutical composition that is sufficient to induce a desired immune response specific for encoded heterologous antigens, show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual (see, e.g., U.S. Pat. No. 5,888,530 issued to Netti, et al.).

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: improving a condition, curing a condition, lessening severity of a condition, delaying progression of a condition, alleviating one or more symptoms associated with a condition, increasing the quality of life of one suffering from a condition, and/or prolonging survival.

"Vaccine" encompasses preventative vaccines. Vaccine also encompasses therapeutic vaccines, e.g., a vaccine administered to a mammal that comprises a condition or disorder associated with the antigen or epitope provided by the vaccine. A number of bacterial species have been developed for use as vaccines and can be used in the present invention, including, but not limited to, *Shigella flexneri, Escherichia coli, Listeria monocytogenes, Yersinia enterocolitica, Salmonella typhimurium, Salmonella typhi* or mycobacterium species. This list is not meant to be limiting. See, e.g., WO04/006837; WO07/103,225; and WO07/117, 371, each of which is hereby incorporated by reference in its entirety, including all tables, figures, and claims. The bacterial vector used in the vaccine composition may be a facultative, intracellular bacterial vector. The bacterium may be used to deliver a polypeptide described herein to antigen-presenting cells in the host organism. As described herein, *L. monocytogenes* provides a preferred vaccine platform for expression of the antigens of the present invention.

Antigenic Constructs

Target Antigens

A preferred feature of the fusion proteins described herein is the ability to initiate both the innate immune response as well as an antigen-specific T cell response against the antigen(s) when recombinantly expressed in a host by a *L. monocytogenes* vaccine platform. For example, *L. monocytogenes* expressing the antigen(s) as described herein can induce Type 1 interferon (IFN-α/β) and a cascade of co-regulated chemokine and cytokine protein which shape the nature of the vaccine-induce immune response. In response to this immune stimulation, NK cells and antigen presenting cells (APCs) are recruited to the liver following intravenous vaccination routes, or, alternatively to the vaccination site following other routes of vaccination, for example, by intramuscular, subcutaneous, or intradermal immunization routes. In certain embodiments, the vaccine platform of the present invention induces an increase at 24 hours following delivery of the vaccine platform to the subject in the serum concentration of one or more, and preferably all, cytokines and chemokines selected from the group consisting of IL-12p70, IFN-γ, IL-6, TNF α, and MCP-1; and induces a CD4+ and/or CD8+ antigen-specific T cell response against one or more antigens expressed by the vaccine platform. In other embodiments, the vaccine platform of the present invention also induces the maturation of resident immature liver NK cells as demonstrated by the upregulation of activation markers such as DX5, CD11b, and CD43 in a mouse model system, or by NK cell-mediated cytolytic activity measured using $^{51}$Cr-labeled YAC-1 cells that were used as target cells.

The ability of *L. monocytogenes* to serve as a vaccine vector has been reviewed in Wesikirch, et al., *Immunol. Rev.* 158:159-169 (1997). A number of desirable features of the natural biology of *L. monocytogenes* make it an attractive platform for application to a therapeutic vaccine. The central rationale is that the intracellular lifecycle of *L. monocytogenes* enables effective stimulation of CD4+ and CD8+ T cell immunity. Multiple pathogen associated molecular pattern (PAMP) receptors including TLRs (TLR2, TLR5, TLR9) nucleotide-binding oligomerization domains (NOD), and Stimulator of Interferon Genes (STING) are triggered in response to interaction with *L. monocytogenes* macromolecules upon infection, resulting in the pan-activation of innate immune effectors and release of Th-1 polarizing cytokines, exerting a profound impact on the development of a CD4+ and CD8+ T cell response against the expressed antigens.

Strains of *L. monocytogenes* have recently been developed as effective intracellular delivery vehicles of heterologous proteins providing delivery of antigens to the immune system to induce an immune response to clinical conditions that do not permit injection of the disease-causing agent, such as cancer and HIV. See, e.g., U.S. Pat. No. 6,051,237; Gunn et al., *J. Immunol.*, 167:6471-6479 (2001); Liau, et al., *Cancer Research*, 62: 2287-2293 (2002); U.S. Pat. No. 6,099,848; WO 99/25376; WO 96/14087; and U.S. Pat. No. 5,830,702), each of which is hereby incorporated by reference in its entirety, including all tables, figures, and claims. A recombinant *L. monocytogenes* vaccine expressing an lymphocytic choriomeningitis virus (LCMV) antigen has also been shown to induce protective cell-mediated immunity to the antigen (Shen et al., Proc. Natl. Acad. Sci. USA, 92: 3987-3991 (1995).

In certain embodiments, the *L. monocytogenes* used in the vaccine compositions of the present invention comprises an attenuating mutation in actA and/or inlB, and preferably a deletion of all or a portion of actA and inlB (referred to herein as "Lm ΔactA/ΔinlB"), and contains recombinant DNA encoding for the expression of the one or more antigen(s) of interest. The antigen(s) are preferably under the control of bacterial expression sequences and are stably integrated into the *L. monocytogenes* genome.

The invention also contemplates a *Listeria* attenuated in at least one regulatory factor, e.g., a promoter or a transcription factor. The following concerns promoters. ActA expression is regulated by two different promoters (Vazwuez-Boland, et al. (1992) Infect. Immun. 60:219-230). Together, InlA and InlB expression is regulated by five promoters (Lingnau, et al. (1995) Infect. Immun. 63:3896-3903). The transcription factor prfA is required for transcription of a number of *L. monocytogenes* genes, e.g., hly, plcA, ActA, mpl, prfA, and iap. PrfA's regulatory properties are mediated by, e.g., the PrfA-dependent promoter (PinlC) and the PrfA-box. The present invention, in certain embodiments, provides a nucleic acid encoding inactivated, mutated, or deleted in at least one of ActA promoter, inlB promoter, PrfA, PinlC, PrfA box, and the like (see, e.g., Lalic Mullthaler, et al. (2001) Mol. Microbiol. 42:111-120; Shetron-Rama, et al. (2003) Mol. Microbiol. 48:1537-1551; Luo, et al. (2004) Mol. Microbiol. 52:39-52). PrfA can be made constitutively active by a Gly145Ser mutation, Gly155Ser mutation, or Glu77Lys mutation (see, e.g., Mueller and Freitag (2005) Infect. Immun. 73:1917-1926; Wong and Freitag (2004) J. Bacteriol. 186:6265-6276; Ripio, et al. (1997) J. Bacteriol. 179:1533-1540).

Examples of target antigens that may find use in the invention are listed in the following table. The target antigen may also be a fragment or fusion polypeptide comprising an immunologically active portion of the antigens listed in the table. This list is not meant to be limiting.

TABLE 1

Antigens.

| Antigen | Reference |
|---|---|
| Tumor antigens | |
| Mesothelin | GenBank Acc. No. NM_005823; U40434; NM_013404; BC003512 (see also, e.g., Hassan, et al. (2004) Clin. Cancer Res. 10: 3937-3942; Muminova, et al. (2004) BMC Cancer 4: 19; Iacobuzio-Donahue, et al. (2003) Cancer Res. 63: 8614-8622). |
| Wilms' tumor-1 associated protein (Wt-1), including isoform A; isoform B; isoform C; isoform D. | WT-1 isoform A (GenBank Acc. Nos. NM_000378; NP_000369). WT-1 isoform B (GenBank Acc. Nos. NM_024424; NP_077742). WT-1 isoform C (GenBank Acc. Nos. NM_024425; NP_077743). WT-1 isoform D (GenBank Acc. Nos. NM_024426; NP_077744). |
| Stratum corneum chymotryptic enzyme (SCCE), and variants thereof. | GenBank Acc. No. NM_005046; NM_139277; AF332583. See also, e.g., Bondurant, et al. (2005) Clin. Cancer Res. 11: 3446-3454; Santin, et al. (2004) Gynecol. Oncol. 94: 283-288; Shigemasa, et al. (2001) Int. J. Gynecol. Cancer 11: 454-461; Sepehr, et al. (2001) Oncogene 20: 7368-7374. |
| MHC class I chain-related protein A (MICA); MHC class I chain-related protein A (MICB). | See, e.g., Groh, et al. (2005) Proc. Natl. Acad. Sci. USA 102: 6461-6466; GenBank Acc. Nos. NM_000247; BC_016929; AY750850; NM_005931. |
| Gastrin and peptides derived from gastrin; gastrin/CCK-2 receptor (also known as CCK-B). | Harris, et al. (2004) Cancer Res. 64: 5624-5631; Gilliam, et al. (2004) Eur. J. Surg. Oncol. 30: 536-543; Laheru and Jaffee (2005) Nature Reviews Cancer 5: 459-467. |
| Glypican-3 (an antigen of, e.g., hepatocellular carcinoma and melanoma). | GenBank Acc. No. NM_004484. Nakatsura, et al. (2003) Biochem. Biophys. Res. Commun. 306: 16-25; Capurro, et al. (2003) Gasteroenterol. 125: 89-97; Nakatsura, et al. (2004) Clin. Cancer Res. 10: 6612-6621). |
| Coactosin-like protein. | Nakatsura, et al. (2002) Eur. J. Immunol. 32: 826-836; Laheru and Jaffee (2005) Nature Reviews Cancer 5: 459-467. |
| Prostate stem cell antigen (PSCA). | GenBank Acc. No. AF043498; AR026974; AR302232 (see also, e.g., Argani, et al. (2001) Cancer Res. 61: 4320-4324; Christiansen, et al. (2003) Prostate 55: 9-19; Fuessel, et al. (2003) 23: 221-228). |
| Prostate acid phosphatase (PAP); prostate-specific antigen (PSA); PSM; PSMA. | Small, et al. (2000) J. Clin. Oncol. 18: 3894-3903; Altwein and Luboldt (1999) Urol. Int. 63: 62-71; Chan, et al. (1999) Prostate 41: 99-109; Ito, et al. (2005) Cancer 103: 242-250; Schmittgen, et al. (2003) Int. J. Cancer 107: 323-329; Millon, et al. (1999) Eur. Urol. 36: 278-285. |
| Six-transmembrane epithelial antigen of prostate (STEAP). | See, e.g., Machlenkin, et al. (2005) Cancer Res. 65: 6435-6442; GenBank Acc. No. NM_018234; NM_001008410; NM_182915; NM_024636; NM_012449; BC011802. |
| Prostate carcinoma tumor antigen-1 (PCTA-1). | See, e.g., Machlenkin, et al. (2005) Cancer Res. 65: 6435-6442; GenBank Acc. No. L78132. |
| Prostate tumor-inducing gene-1 (PTI-1). | See, e.g., Machlenkin, et al. (2005) Cancer Res. 65: 6435-6442. |
| Prostate-specific gene with homology to G protein-coupled receptor. | See, e.g., Machlenkin, et al. (2005) Cancer Res. 65: 6435-6442. |
| Prostase (an antrogen regulated serine protease). | See, e.g., Machlenkin, et al. (2005) Cancer Res. 65: 6435-6442; GenBank Acc. No. BC096178; BC096176; BC096175. |
| Proteinase 3. | GenBank Acc. No. X55668. |
| Cancer-testis antigens, e.g., NY-ESO-1; SCP-1; SSX-1; SSX-2; SSX-4; GAGE, CT7; CT8; CT10; MAGE-1; MAGE-2; MAGE-3; MAGE-4; MAGE-6; LAGE-1. | GenBank Acc. No. NM_001327 (NY-ESO-1) (see also, e.g., Li, et al. (2005) Clin. Cancer Res. 11: 1809-1814; Chen, et al. (2004) Proc. Natl. Acad. Sci. USA. 101(25): 9363-9368; Kubuschok, et al. (2004) Int. J. Cancer. 109: 568-575; Scanlan, et al. (2004) Cancer Immun. 4: 1; Scanlan, et al. (2002) Cancer Res. 62: 4041-4047; Scanlan, et al. (2000) Cancer Lett. 150: 155-164; Dalerba, et al. (2001) Int. J. Cancer 93: 85-90; Ries, et al. (2005) Int. J. Oncol. 26: 817-824. |
| MAGE-A1, MAGE-A2; MAGE-A3; MAGE-A4; | Otte, et al. (2001) Cancer Res. 61: 6682-6687; Lee, et al. (2003) Proc. Natl. Acad. Sci. USA 100: 2651-2656; Sarcevic, et al. (2003) Oncology 64: 443- |

TABLE 1-continued

Antigens.

| Antigen | Reference |
|---|---|
| MAGE-A6; MAGE-A9; MAGE-A10; MAGE-A12; GAGE-3/6; NT-SAR-35; BAGE; CA125. | 449; Lin, et al. (2004) Clin. Cancer Res. 10: 5708-5716. |
| GAGE-1; GAGE-2; GAGE-3; GAGE-4; GAGE-5; GAGE-6; GAGE-7; GAGE-8; GAGE-65; GAGE-11; GAGE-13; GAGE-7B. | De Backer, et al. (1999) Cancer Res. 59: 3157-3165; Scarcella, et al. (1999) Clin. Cancer Res. 5: 335-341. |
| HIP1R; LMNA; KIAA1416; Seb4D; KNSL6; TRIP4; MBD2; HCAC5; MAGEA3. | Scanlan, et al. (2002) Cancer Res. 62: 4041-4047. |
| DAM family of genes, e.g., DAM-1; DAM-6. | Fleishhauer, et al. (1998) Cancer Res. 58: 2969-2972. |
| RCAS1. | Enjoji, et al. (2004) Dig. Dis. Sci. 49: 1654-1656. |
| RU2. | Van Den Eynde, et al. (1999) J. Exp. Med. 190: 1793-1800. |
| CAMEL. | Slager, et al. (2004) J. Immunol. 172: 5095-5102; Slager, et al. (2004) Cancer Gene Ther. 11: 227-236. |
| Colon cancer associated antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP4; NY-CO-95/KIAA1416; KNSL6; seb4D. | Scanlan, et al. (2002) Cancer Res. 62: 4041-4047. |
| N-Acetylglucosaminyl-tranferase V (GnT-V). | Dosaka-Akita, et al. (2004) Clin. Cancer Res. 10: 1773-1779. |
| Elongation factor 2 mutated (ELF2M). | Renkvist, et al. (2001) Cancer Immunol Immunother. 50: 3-15. |
| HOM-MEL-40/SSX2 | Neumann, et al. (2004) Int. J. Cancer 112: 661-668; Scanlan, et al. (2000) Cancer Lett. 150: 155-164. |
| BRDT. | Scanlan, et al. (2000) Cancer Lett. 150: 155-164. |
| SAGE; HAGE. | Sasaki, et al. (2003) Eur. J. Surg. Oncol. 29: 900-903. |
| RAGE. | See, e.g., Li, et al. (2004) Am. J. Pathol. 164: 1389-1397; Shirasawa, et al. (2004) Genes to Cells 9: 165-174. |
| MUM-1 (melanoma ubiquitous mutated); MUM-2; MUM-2 Arg-Gly mutation; MUM-3. | Gueguen, et al. (1998) J. Immunol. 160: 6188-6194; Hirose, et al. (2005) Int. J. Hematol. 81: 48-57; Baurain, et al. (2000) J. Immunol. 164: 6057-6066; Chiari, et al. (1999) Cancer Res. 59: 5785-5792. |
| LDLR/FUT fusion protein antigen of melanoma. | Wang, et al. (1999) J. Exp. Med. 189: 1659-1667. |
| NY-REN series of renal cancer antigens. | Scanlan, et al. (2002) Cancer Res. 62: 4041-4047; Scanlan, et al. (1999) Cancer Res. 83: 456-464. |
| NY-BR series of breast cancer antigens, e.g., NY-BR-62; NY-BR-75; NY-BR-85; NY-BR-62; NY-BR-85. | Scanlan, et al. (2002) Cancer Res. 62: 4041-4047; Scanlan, et al. (2001) Cancer Immunity 1: 4. |
| BRCA-1; BRCA-2. | Stolier, et al. (2004) Breast J. 10: 475-480; Nicoletto, et al. (2001) Cancer Treat Rev. 27: 295-304. |
| DEK/CAN fusion protein. | Von Lindern, et al. (1992) Mol. Cell. Biol. 12: 1687-1697. |
| Ras, e.g., wild type ras, ras with mutations at codon 12, 13, 59, or 61, e.g., mutations G12C; G12D; G12R; G12S; G12V; G13D; A59T; Q61H. K-RAS; H-RAS; N-RAS. | GenBank Acc. Nos. P01112; P01116; M54969; M54968; P01111; P01112; K00654. See also, e.g., GenBank Acc. Nos. M26261; M34904; K01519; K01520; BC006499; NM_006270; NM_002890; NM_004985; NM_033360; NM_176795; NM_005343. |
| BRAF (an isoform of RAF). | Tannapfel, et al. (2005) Am. J. Clin. Pathol. 123: 256-2601; Tsao and Sober (2005) Dermatol. Clin. 23: 323-333. |
| Melanoma antigens, including HST-2 melanoma cell antigens. | GenBank Acc. No. NM_206956; NM_206955; NM_206954; NM_206953; NM_006115; NM_005367; NM_004988; AY148486; U10340; U10339; M77481. See, eg., Suzuki, et al. (1999) J. Immunol. 163: 2783-2791. |

TABLE 1-continued

Antigens.

| Antigen | Reference |
|---|---|
| Survivin | GenBank Acc. No. AB028869; U75285 (see also, e.g., Tsuruma, et al. (2004) J. Translational Med. 2: 19 (11 pages); Pisarev, et al. (2003) Clin. Cancer Res. 9: 6523-6533; Siegel, et al. (2003) Br. J. Haematol. 122: 911-914; Andersen, et al. (2002) Histol. Histopathol. 17: 669-675). |
| MDM-2 | NM_002392; NM_006878 (see also, e.g., Mayo, et al. (1997) Cancer Res. 57: 5013-5016; Demidenko and Blagosklonny (2004) Cancer Res. 64: 3653-3660). |
| Methyl-CpG-binding proteins (MeCP2; MBD2). | Muller, et al. (2003) Br. J. Cancer 89: 1934-1939; Fang, et al. (2004) World J. Gastreenterol. 10: 3394-3398. |
| NA88-A. | Moreau-Aubry, et al. (2000) J. Exp. Med. 191: 1617-1624. |
| Histone deacetylases (HDAC), e.g., HDAC5. | Waltregny, et al. (2004) Eur. J. Histochem. 48: 273-290; Scanlan, et al. (2002) Cancer Res. 62: 4041-4047. |
| Cyclophilin B (Cyp-B). | Tamura, et al. (2001) Jpn. J. Cancer Res. 92: 762-767. |
| CA 15-3; CA 27.29. | Clinton, et al. (2003) Biomed. Sci. Instrum. 39: 408-414. |
| Heat shock protein Hsp70. | Faure, et al. (2004) Int. J. Cancer 108: 863-870. |
| GAGE/PAGE family, e.g., PAGE-1; PAGE-2; PAGE-3; PAGE-4; XAGE-1; XAGE-2; XAGE-3. | Brinkmann, et al. (1999) Cancer Res. 59: 1445-1448. |
| MAGE-A, B, C, and D families. MAGE-B5; MAGE-B6; MAGE-C2; MAGE-C3; MAGE-3; MAGE-6. | Lucas, et al. (2000) Int. J. Cancer 87: 55-60; Scanlan, et al. (2001) Cancer Immun. 1: 4. |
| Kinesin 2; TATA element modulatory factor 1; tumor protein D53; NY | Scanlan, et al. (2001) Cancer Immun. 30: 1-4. |
| Alpha-fetoprotein (AFP) | Grimm, et al. (2000) Gastroenterol. 119: 1104-1112. |
| SART1; SART2; SART3; ART4. | Kumamuru, et al. (2004) Int. J. Cancer 108: 686-695; Sasatomi, et al. (2002) Cancer 94: 1636-1641; Matsumoto, et al. (1998) Jpn. J. Cancer Res. 89: 1292-1295; Tanaka, et al. (2000) Jpn. J. Cancer Res. 91: 1177-1184. |
| Preferentially expressed antigen of melanoma (PRAME). | Matsushita, et al. (2003) Leuk. Lymphoma 44: 439-444; Oberthuer, et al. (2004) Clin. Cancer Res. 10: 4307-4313. |
| Carcinoembryonic antigen (CEA), CAP1-6D enhancer agonist peptide. | GenBank Acc. No. M29540; E03352; X98311; M17303 (see also, e.g., Zaremba (1997) Cancer Res. 57: 4570-4577; Sarobe, et al. (2004) Curr. Cancer Drug Targets 4: 443-454; Tsang, et al. (1997) Clin. Cancer Res. 3: 2439-2449; Fong, et al. (2001) Proc. Natl. Acad. Sci. USA 98: 8809-8814). |
| HER-2/neu. | Disis, et al. (2004) J. Clin. Immunol. 24: 571-578; Disis and Cheever (1997) Adv. Cancer Res. 71: 343-371. |
| Cdk4; cdk6; p16 (INK4); Rb protein. | Ghazizadeh, et al. (2005) Respiration 72: 68-73; Ericson, et al. (2003) Mol. Cancer Res. 1: 654-664. |
| TEL; AML1; TEL/AML1. | Stams, et al. (2005) Clin. Cancer Res. 11: 2974-2980. |
| Telomerase (TERT). | Nair, et al. (2000) Nat. Med. 6: 1011-1017. |
| 707-AP. | Takahashi, et al. (1997) Clin. Cancer Res. 3: 1363-1370. |
| Annexin, e.g., Annexin II. | Zimmerman, et al. (2004) Virchows Arch. 445: 368-374. |
| BCR/ABL; BCR/ABL p210; BCR/ABL p190; CML-66; CML-28. | Cobaldda, et al. (2000) Blood 95: 1007-1013; Hakansson, et al. (2004) Leukemia 18: 538-547; Schwartz, et al. (2003) Semin. Hematol. 40: 87-96; Lim, et al. (1999) Int. J. Mol. Med. 4: 665-667. |
| BCL2; BLC6; CD10 protein. | Iqbal, et al. (2004) Am. J. Pathol. 165: 159-166. |
| CDC27 (this is a melanoma antigen). | Wang, et al. (1999) Science 284: 1351-1354. |
| Sperm protein 17 (SP17); 14-3-3-zeta; MEMD; KIAA0471; TC21. | Arora, et al. (2005) Mol. Carcinog. 42: 97-108. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Gp100/pmel-17. | GenBank Acc. Nos. AH003567; U31798; U31799; U31807; U31799 (see also, e.g., Bronte, et al. (2000) Cancer Res. 60: 253-258). |
| TARP. | See, e.g., Clifton, et al. (2004) Proc. Natl. Acad. Sci. USA 101: 10166-10171; Virok, et al. (2005) Infection Immunity 73: 1939-1946. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Melanocortin 1 receptor (MC1R); MAGE-3; | Salazar-Onfray, et al. (1997) Cancer Res. 57: 4348-4355; Reynolds, et al. (1998) J. Immunol. 161: 6970-6976; Chang, et al. (2002) Clin. Cancer Res. |

TABLE 1-continued

| Antigens. | |
|---|---|
| Antigen | Reference |
| gp100; tyrosinase; dopachrome tautomerase (TRP-2); MART-1. | 8: 1021-1032. |
| MUC-1; MUC-2. | See, e.g., Davies, et al. (1994) Cancer Lett. 82: 179-184; Gambus, et al. (1995) Int. J. Cancer 60: 146-148; McCool, et al. (1999) Biochem. J. 341: 593-600. |
| Spas-1. | U.S. Published patent application No. 20020150588 of Allison, et al. |
| CASP-8; FLICE; MACH. | Mandruzzato, et al. (1997) J. Exp. Med. 186: 785-793. |
| CEACAM6; CAP-1. | Duxbury, et al. (2004) Biochem. Biophys. Res. Commun. 317: 837-843; Morse, et al. (1999) Clin. Cancer Res. 5: 1331-1338. |
| HMGB1 (a DNA binding protein and cytokine). | Brezniceanu, et al. (2003) FASEB J. 17: 1295-1297. |
| ETV6/AML1. | Codrington, et al. (2000) Br. J. Haematol. 111: 1071-1079. |
| Mutant and wild type forms of adenomatous polyposis coli (APC); beta-catenin; c-met; p53; E-cadherin; cyclooxygenase-2 (COX-2). | Clements, et al. (2003) Clin. Colorectal Cancer 3: 113-120; Gulmann, et al. (2003) Appl. Immunohistochem. Mol. Morphol. 11: 230-237; Jungck, et al. (2004) Int. J. Colorectal. Dis. 19: 438-445; Wang, et al. (2004) J. Surg. Res. 120: 242-248; Abutaily, et al. (2003) J. Pathol. 201: 355-362; Liang, et al. (2004) Br. J. Surg. 91: 355-361; Shirakawa, et al. (2004) Clin. Cancer Res. 10: 4342-4348. |
| Renal cell carcinoma antigen bound by mAB G250. | Mulders, et al. (2003) Urol. Clin. North Am. 30: 455-465; Steffens, et al. (1999) Anticancer Res. 19: 1197-1200. |
| EphA2 | See. e.g., U.S. Patent Publication No. 2005/0281783 A1; Genbank Accession No. NM_004431 (human); Genbank Accession No. NM_010139 (Mouse); Genbank Accession No. AB038986 (Chicken, partial sequence); GenBank Accession Nos. NP_004422, AAH37166, and AAA53375 (human); GenBank Accession Nos. NP_034269 (mouse), AAH06954 (mouse), XP_345597 (rat), and BAB63910 (chicken). |
| *Francisella tularensis* antigens | |
| *Francisella tularensis* A and B. | Complete genome of subspecies Schu S4 (GenBank Acc. No. AJ749949); of subspecies Schu 4 (GenBank Acc. No. NC_006570). Outer membrane protein (43 kDa) Bevanger, et al. (1988) J. Clin. Microbiol. 27: 922-926; Porsch-Ozcurumez, et al. (2004) Clin. Diagnostic. Lab. Immunol. 11: 1008-1015). Antigenic components of *F. tularensis* include, e.g., 80 antigens, including 10 kDa and 60 kDa chaperonins (Havlasova, et al. (2002) Proteomics 2: 857-86), nucleoside diphosphate kinase, isocitrate dehydrogenase, RNA-binding protein Hfq, the chaperone ClpB (Havlasova, et al. (2005) Proteomics 5: 2090-2103). See also, e.g., Oyston and Quarry (2005) Antonie Van Leeuwenhoek 87: 277-281; Isherwood, et al. (2005) Adv. Drug Deliv. Rev. 57: 1403-1414; Biagini, et al. (2005) Anal. Bioanal. Chem. 382: 1027-1034. |
| Malarial antigens | |
| Circumsporozoite protein (CSP); SSP2; HEP17; Exp-1 orthologs found in *P. falciparum*; and LSA-1. | See, e.g., Haddad, et al. (2004) Infection Immunity 72: 1594-1602; Hoffman, et al. (1997) Vaccine 15: 842-845; Oliveira-Ferreira and Daniel-Ribeiro (2001) Mem. Inst. Oswaldo Cruz, Rio de Janeiro 96: 221-227. CSP (see, e.g., GenBank Acc. No. AB121024). SSP2 (see, e.g., GenBank Acc. No. AF249739). LSA-1 (see, e.g., GenBank Acc. No. Z30319). |
| Ring-infected erythrocyte survace protein (RESA); merozoite surface protein 2 (MSP2); Spf66; merozoite surface protein 1(MSP1); 195A; BVp42. | See, e.g., Stirnadel, et al. (2000) Int. J. Epidemiol. 29: 579-586; Krzych, et al. (1995) J. Immunol. 155: 4072-4077. See also, Good, et al. (2004) Immunol. Rev. 201: 254-267; Good, et al. (2004) Ann. Rev. Immunol. 23: 69-99. MSP2 (see, e.g., GenBank Acc. No. X96399; X96397). MSP1 (see, e.g., GenBank Acc. No. X03371). RESA (see, e.g., GenBank Acc. No. X05181; X05182). |
| Apical membrane antigen 1 (AMA1). | See, e.g., Gupta, et al. (2005) Protein Expr. Purif. 41: 186-198. AMA1 (see, e.g., GenBank Acc. No. A`13; AJ494905; AJ490565). |
| Viruses and viral antigens | |
| Hepatitis A | GenBank Acc. Nos., e.g., NC_001489; AY644670; X83302; K02990; M14707. |
| Hepatitis B | Complete genome (see, e.g., GenBank Acc. Nos. AB214516; NC_003977; AB205192; AB205191; AB205190; AJ748098; AB198079; AB198078; AB198076; AB074756). |
| Hepatitis C | Complete genome (see, e.g., GenBank Acc. Nos. NC_004102; AJ238800; AJ238799; AJ132997; AJ132996; AJ000009; D84263). |
| Hepatitis D | GenBank Acc. Nos, e.g. NC_001653; AB118847; AY261457. |
| Human papillomavirus, including all 200+ subtypes (classed in 16 groups), such as the high risk subtypes 16, | See, e.g., Trimble, et al. (2003) Vaccine 21: 4036-4042; Kim, et al. (2004) Gene Ther. 11: 1011-1018; Simon, et al. (2003) Eur. J. Obstet. Gynecol. Reprod. Biol. 109: 219-223; Jung, et al. (2004) J. Microbiol. 42: 255-266; Damasus-Awatai and Freeman-Wang (2003) Curr. Opin. Obstet. Gynecol. 15: 473-477; Jansen and Shaw (2004) Annu. Rev. |

TABLE 1-continued

Antigens.

| Antigen | Reference |
|---|---|
| 18, 30, 31, 33, 45. | Med. 55: 319-331; Roden and Wu (2003) Expert Rev. Vaccines 2: 495-516; de Villiers, et al. (2004) Virology 324: 17-24; Hussain and Paterson (2005) Cancer Immunol. Immunother. 54: 577-586; Molijn, et al. (2005) J. Clin. Virol. 32 (Suppl. 1) S43-S51. GenBank Acc. Nos. AY686584; AY686583; AY686582; NC_006169; NC_006168; NC_006164; NC_001355; NC_001349; NC_005351; NC_001596). |
| Human T-cell lymphotropic virus (HTLV) types I and II, including the HTLV type I subtypes Cosmopolitan, Central African, and Austro-Melanesian, and the HTLV type II subtypes IIa, IIb, IIc, and IId. | See, e.g., Capdepont, et al. (2005) AIDS Res. Hum. Retrovirus 21: 28-42; Bhigjee, et al. (1999) AIDS Res. Hum. Restrovirus 15: 1229-1233; Vandamme, et al. (1998) J. Virol. 72: 4327-4340; Vallejo, et al. (1996) J. Acquir. Immune Defic. Syndr. Hum. Retrovirol. 13: 384-391. HTLV type I (see, e.g., GenBank Acc. Nos. AY563954; AY563953. HTLV type II (see, e.g., GenBank Acc. Nos. L03561; Y13051; AF139382). |
| Coronaviridae, including Coronaviruses, such as SARS-coronavirus (SARS-CoV), and Toroviruses. | See, e.g., Brian and Baric (2005) Curr. Top. Microbiol. Immunol. 287: 1-30; Gonzalez, et al. (2003) Arch. Virol. 148: 2207-2235; Smits, et al. (2003) J. Virol. 77: 9567-9577; Jamieson, et al. (1998) J. Infect. Dis. 178: 1263-1269 (GenBank Acc. Nos. AY348314; NC_004718; AY394850). |
| Rubella virus. | GenBank Acc. Nos. NC_001545; AF435866. |
| Mumps virus, including the genotypes A, C, D, G, H, and I. | See, e.g., Orvell, eta 1. (2002) J. Gen. Virol. 83: 2489-2496. See, e.g., GenBank Acc. Nos. AY681495; NC_002200; AY685921; AF201473. |
| Coxsackie virus A including the serotypes 1, 11, 13, 15, 17, 18, 19, 20, 21, 22, and 24 (also known as Human enterovirus C; HEV-C). | See, e.g., Brown, et al. (2003) J. Virol. 77: 8973-8984. GenBank Acc. Nos. AY421768; AY790926; X67706. |
| Coxsackie virus B, including subtypes 1-6. | See, e.g., Ahn, et al. (2005) J. Med. Virol. 75: 290-294; Patel, et al. (2004) J. Virol. Methods 120: 167-172; Rezig, et al. (2004) J. Med. Virol. 72: 268-274. GenBank Acc. No. X05690. |
| Human enteroviruses including, e.g., human enterovirus A (HEV-A, CAV2 to CAV8, CAV10, CAV12, CAV14, CAV16, and EV71) and also including HEV-B (CAV9, CBV1 to CBV6, E1 to E7, E9, E11 to E21, E24 to E27, E29 to E33, and EV69 and E73), as well as HEV. | See, e.g., Oberste, et al. (2004) J. Virol. 78: 855-867. Human enterovirus A (GenBank Acc. Nos. NC_001612); human enterovirus B (NC_001472); human enterovirus C (NC_001428); human enterovirus D (NC_001430). Simian enterovirus A (GenBank Acc. No. NC_003988). |
| Polioviruses including PV1, PV2, and PV3. | See, e.g., He, et al. (2003) J. Virol. 77: 4827-4835; Hahsido, et al. (1999) Microbiol. Immunol. 43: 73-77. GenBank Acc. No. AJ132961 (type 1); AY278550 (type 2); X04468 (type 3). |
| Viral encephalitides viruses, including equine encephalitis, Venezuelan equine encephalitis (VEE) (including subtypes IA, IB, IC, ID, IIIC, IIID), Eastern equine encephalitis (EEE), Western equine encephalitis (WEE), St. Louis encephalitis, Murray Valley (Australian) encephalitis, Japanese encephalitis, and tick-born encephalitis. | See, e.g., Hoke (2005) Mil. Med. 170: 92-105; Estrada-Franco, et al. (2004) Emerg. Infect. Dis. 10: 2113-2121; Das, et al. (2004) Antiviral Res. 64: 85-92; Aguilar, et al. (2004) Emerg. Infect. Dis. 10: 880-888; Weaver, et al. (2004) Arch. Virol. Suppl. 18: 43-64; Weaver, et al. (2004) Annu. Rev. Entomol. 49: 141-174. Eastern equine encephalitis (GenBank Acc. No. NC_003899; AY722102); Western equine encephalitis (NC_003908). |
| Human herpesviruses, including cytomegalovirus (CMV), Epstein-Barr virus (EBV), human | See, e.g., Studahl, et al. (2000) Scand. J. Infect. Dis. 32: 237-248; Padilla, et al. (2003) J. Med. Virol. 70 (Suppl. 1) S103-S110; Jainkittivong and Langlais (1998) Oral Surg. Oral Med. 85: 399-403. GenBank Nos. NC_001806 (herpesvirus 1); NC_001798 (herpesvirus 2); X04370 and NC_001348 (herpesvirus 3); |

TABLE 1-continued

Antigens.

| Antigen | Reference |
| --- | --- |
| herpesvirus-1 (HHV-1), HHV-2, HHV-3, HHV-4, HHV-5, HHV-6, HHV-7, HHV-8, herpes B virus, herpes simplex virus types 1 and 2 (HSV-1, HSV-2), and varicella zoster virus (VZV). | NC_001345 (herpesvirus 4); NC_001347 (herpesvirus 5); X83413 and NC_000898 (herpesvirus 6); NC_001716 (herpesvirus 7). Human herpesviruses types 6 and 7 (HHV-6; HHV-7) are disclosed by, e.g., Padilla, et al. (2003) J. Med. Virol. 70 (Suppl. 1)S103-S110. Human herpesvirus 8 (HHV-8), including subtypes A-E, are disclosed in, e.g., Treurnicht, et al. (2002) J. Med. Virol. 66: 235-240. |
| HIV-1 including group M (including subtypes A to J) and group O (including any distinguishable subtypes) (HIV-2, including subtypes A-E. | See, e.g., Smith, et al. (1998) J. Med. Virol. 56: 264-268. See also, e.g., GenBank Acc. Nos. DQ054367; NC_001802; AY968312; DQ011180; DQ011179; DQ011178; DQ011177; AY588971; AY588970; AY781127; AY781126; AY970950; AY970949; AY970948; X61240; AJ006287; AJ508597; and AJ508596. |
| Epstein-Barr virus (EBV), including subtypes A and B. | See, e.g., Peh, et al. (2002) Pathology 34: 446-450. Epstein-Barr virus strain B95-8 (GenBank Acc. No. V01555). |
| Reovirus, including serotypes and strains 1, 2, and 3, type 1 Lang, type 2 Jones, and type 3 Dearing. | See, e.g., Barthold, et al. (1993) Lab. Anim. Sci. 43: 425-430; Roner, et al. (1995) Proc. Natl. Acad. Sci. USA 92: 12362-12366; Kedl, et al. (1995) J. Virol. 69: 552-559. GenBank Acc. No. K02739 (sigma-3 gene surface protein). |
| Cytomegalovirus (CMV) subtypes include CMV subtypes I-VII. | See, e.g., Chern, et al. (1998) J. Infect. Dis. 178: 1149-1153; Vilas Boas, et al. (2003) J. Med. Virol. 71: 404-407; Trincado, et al. (2000) J. Med. Virol. 61: 481-487. GenBank Acc. No. X17403. |
| Rhinovirus, including all serotypes. | Human rhinovirus 2 (GenBank Acc. No. X02316); Human rhinovirus B (GenBank Acc. No. NC_001490); Human rhinovirus 89 (GenBank Acc. No. NC_001617); Human rhinovirus 39 (GenBank Acc. No. AY751783). |
| Adenovirus, including all serotypes. | AY803294; NC_004001; AC_000019; AC_000018; AC_000017; AC_000015; AC_000008; AC_000007; AC_000006; AC_000005; AY737798; AY737797; NC_003266; NC_002067; AY594256; AY594254; AY875648; AJ854486; AY163756; AY594255; AY594253; NC_001460; NC_001405; AY598970; AY458656; AY487947; NC_001454; AF534906; AY45969; AY128640; L19443; AY339865; AF532578. |
| Varicella-zoster virus, including strains and genotypes Oka, Dumas, European, Japanese, and Mosaic. | See, e.g., Loparev, et al. (2004) J. Virol. 78: 8349-8358; Carr, et al. (2004) J. Med. Virol. 73: 131-136; Takayama and Takayama (2004) J. Clin. Virol. 29: 113-119. |
| Filoviruses, including Marburg virus and Ebola virus, and strains such as Ebola-Sudan (EBO-S), Ebola-Zaire (EBO-Z), and Ebola-Reston (EBO-R). | See, e.g., Geisbert and Jahrling (1995) Virus Res. 39: 129-150; Hutchinson, et al. (2001) J. Med. Virol. 65: 561-566. Marburg virus (see, e.g., GenBank Acc. No. NC_001608). Ebola virus (see, e.g., GenBank Acc. Nos. NC_006432; AY769362; NC_002549; AF272001; AF086833). |
| Arenaviruses, including lymphocytic choriomeningitis (LCM) virus, Lassa virus, Junin virus, and Machupo virus. | Junin virus, segment S (GenBank Acc. No. NC_005081); Junin virus, segment L (GenBank Acc. No. NC_005080). |
| Rabies virus. | See, e.g., GenBank Acc. Nos. NC_001542; AY956319; AY705373; AF499686; AB128149; AB085828; AB009663. |
| Arboviruses, including West Nile virus, Dengue viruses 1 to 4, Colorado tick fever virus, Sindbis virus, Togaviraidae, Flaviviridae, Bunyaviridae, Reoviridae, Rhabdoviridae, Orthomyxoviridae, and the like. | Dengue virus type 1 (see, e.g., GenBank Acc. Nos. AB195673; AY762084). Dengue virus type 2 (see, e.g., GenBank Acc. Nos. NC_001474; AY702040; AY702039; AY702037). Dengue virus type 3 (see, e.g., GenBank Acc. Nos. AY923865; AT858043). Dengue virus type 4 (see, e.g., GenBank Acc. Nos. AY947539; AY947539; AF326573). Sindbis virus (see, e.g., GenBank Acc. Nos. NC_001547; AF429428; J02363; AF103728). West Nile virus (see, e.g., GenBank Acc. Nos. NC_001563; AY603654). |
| Poxvirus including orthopoxvirus (variola virus, monkeypox virus, vaccinia virus, | Viriola virus (see, e.g., GenBank Acc. Nos. NC_001611; Y16780; X72086; X69198). |

TABLE 1-continued

Antigens.

| Antigen | Reference |
|---|---|
| cowpox virus), yatapoxvirus (tanapox virus, Yaba monkey tumor virus), parapoxvirus, and molluscipoxvirus. | |
| Yellow fever. | See, e.g., GenBank Acc. No. NC_002031; AY640589; X03700. |
| Hantaviruses, including serotypes Hantaan (HTN), Seoul (SEO), Dobrava (DOB), Sin Nombre (SN), Puumala (PUU), and Dobrava-like Saaremaa (SAAV). | See, e.g., Elgh, et al. (1997) J. Clin. Microbiol. 35: 1122-1130; Sjolander, et al. (2002) Epidemiol. Infect. 128: 99-103; Zeier, et al. (2005) Virus Genes 30: 157-180. GenBank Acc. No. NC_005222 and NC_005219 (Hantavirus). See also, e.g., GenBank Acc. Nos. NC_005218; NC_005222; NC_005219. |
| Flaviviruses, including Dengue virus, Japanese encephalitis virus, West Nile virus, and yellow fever virus. | See, e.g., Mukhopadhyay, et al. (2005) Nature Rev. Microbiol. 3: 13-22. GenBank Acc. Nos NC_001474 and AY702040 (Dengue). GenBank Acc. Nos. NC_001563 and AY603654. |
| Measles virus. | See, e.g., GenBank Acc. Nos. AB040874 and AY486084. |
| Human parainfluenzaviruses (HPV), including HPV types 1-56. | Human parainfluenza virus 2 (see, e.g., GenBank Acc. Nos. AB176531; NC003443). Human parainfluenza virus 3 (see, e.g., GenBank Acc. No. NC_001796). |
| Influenza virus, including influenza virus types A, B, and C. | Influenza nucleocapsid (see, e.g., GenBank Acc. No. AY626145). Influenza hemagglutinin (see, e.g., GenBank Acc. Nos. AY627885; AY555153). Influenza neuraminidase (see, e.g., GenBank Acc. Nos. AY555151; AY577316). Influenza matrix protein 2 (see, e.g., GenBank Acc. Nos. AY626144(.Influenza basic protein 1 (see, e.g., GenBank Acc. No. AY627897). Influenza polymerase acid protein (see, e.g., GenBank Acc. No. AY627896). Influenza nucleoprotein (see, e.g., GenBank Acc. Nno. AY627895). |
| Influenza A virus subtypes, e.g., swine viruses (SIV): H1N1 influenzaA and swine influenza virus. | Hemagglutinin of H1N1 (GenBank Acc. No. S67220). Influenza A virus matrix protein (GenBank Acc. No. AY700216). Influenza virus A H5H1 nucleoprotein (GenBank Acc. No. AY646426). H1N1 haemagglutinin (GenBank Acc. No. D00837). See also, GenBank Acc. Nos. BD006058; BD006055; BD006052. See also, e.g., Wenrworth, et al. (1994) J. Virol. 68: 2051-2058; Wells, et al. (1991) J.A.M.A. 265: 478-481. |
| Respiratory syncytial virus (RSV), including subgroup A and subgroup B. | Respiratory syncytial virus (RSV) (see, e.g., GenBank Acc. Nos. AY353550; NC_001803; NC001781). |
| Rotaviruses, including human rotaviruses A to E, bovine rotavirus, rhesus monkey rotavirus, and human-RVV reassortments. | Human rotavirus C segment 8 (GenBank Acc. No. AJ549087); Human rotavirus G9 strain outer capsid protein (see, e.g., GenBank Acc. No. DQ056300); Human rotavirus B strain non-structural protein 4 (see, e.g., GenBank Acc. No. AY548957); human rotavirus A strain major inner capsid protein (see, e.g., GenBank Acc. No. AY601554). |
| Polyomavirus, including simian virus 40 (SV40), JC virus (JCV) and BK virus (BKV). | See, e.g., Engels, et al. (2004) J. Infect. Dis. 190: 2065-2069; Vilchez and Butel (2004) Clin. Microbiol. Rev. 17: 495-508; Shivapurkar, et al. (2004) Cancer Res. 64: 3757-3760; Carbone, et al. (2003) Oncogene 2: 5173-5180; Barbanti-Brodano, et al. (2004) Virology 318: 1-9) (SV40 complete genome in, e.g., GenBank Acc. Nos. NC_001669; AF168994; AY271817; AY271816; AY120890; AF345344; AF332562). |
| Coltiviruses, including Colorado tick fever virus, Eyach virus. | Attoui, et al. (1998) J. Gen. Virol. 79: 2481-2489. Segments of Eyach virus (see, e.g., GenBank Acc. Nos. AF282475; AF282472; AF282473; AF282478; AF282476; NC_003707; NC_003702; NC_003703; NC_003704; NC_003705; NC_003696; NC_003697; NC_003698; NC_003699; NC_003701; NC_003706; NC_003700; AF282471; AF282477). |
| Calciviruses, including the genogroups Norwalk, Snow Mountain group (SMA), and Saaporo. | Snow Mountain virus (see, e.g., GenBank Acc. No. AY134748). |
| Parvoviridae, including dependovirus, parvovirus (including parvovirus B19), and erythrovirus. | See, e.g., Brown (2004) Dev. Biol. (Basel) 118: 71-77; Alvarez-Lafuente, et al. (2005) Ann. Rheum. Dis. 64: 780-782; Ziyaeyan, et al. (2005) Jpn. J. Infect. Dis. 58: 95-97; Kaufman, et al. (2005) Virology 332: 189-198. |

Other organisms for which suitable antigens are known in the art include, but are not limited to, *Chlamydia trachomatis, Streptococcus pyogenes* (Group A Strep), *Streptococcus agalactia* (Group B Strep), *Streptococcus pneumonia, Staphylococcus aureus, Escherichia coli, Haemophilus influenzae, Neisseria meningitidis, Neisseria gonorrheae, Vibrio cholerae, Salmonella* species (including *typhi, typhimurium*), enterica (including *Helicobactor pylori Shigella flexneri* and other Group D *shigella* species), *Burkholderia mallei, Burkholderia pseudomallei, Klebsiella pneumonia, Clostridium* species (including *C. difficile*), *Vibrio parahaemolyticus* and *V. vulnificus*. This list is not meant to be limiting.

As described herein antigen sequence(s) are preferably expressed as a single polypeptide fused to a modified amino-terminal portion of the *L. monocytogenes* ActA or LLO protein in frame with the ActA or LLO secretory signal sequence. The ActA signal sequence is MGLNRFMRAM-MVVFITANCITINPDIIFA (SEQ ID NO: 10); the LLO signal sequence is MKKIMLVFIT LILVSLPIAQ QTE (SEQ ID NO: 11). Preferably, the native signal sequence used is not modified in the construct.

In some embodiments, the modified ActA comprises a modified form of about the first 100 amino acids of ActA, referred to herein as ActA-N100. ActA-N100 has the following sequence (SEQ ID NO: 12):

```
VGLNRFMRAM MVVFITANCI TINPDIIFAA TDSEDSSLNT DEWEEEKTEE      50
QPSEVNTGPR YETAREVSSR DIEELEKSNK VKNTNKADLI AMLKAKAEKG     100
```

In this sequence, the first residue is depicted as a valine; the polypeptide is synthesized by *Listeria* with a methionine in this position. Thus, ActA-N100 may also have the following sequence (SEQ ID NO: 13):

```
MGLNRFMRAM MVVFITANCI TINPDIIFAA TDSEDSSLNT DEWEEEKTEE      50
QPSEVNTGPR YETAREVSSR DIEELEKSNK VKNTNKADLI AMLKAKAEKG     100
```

The constructs of the present invention may also comprise one or more additional, non-ActA, residues lying between the C-terminal residue of the modified ActA and the antigen sequence. In the following sequences, ActA-N100 is extended by two residues added by inclusion of a BamH1 site (SEQ ID NO: 14):

```
VGLNRFMRAM MVVFITANCI TINPDIIFAA TDSEDSSLNT DEWEEEKTEE      50
QPSEVNTGPR YETAREVSSR DIEELEKSNK VKNTNKADLI AMLKAKAEKG     100
GS
``` which when synthesized with a first residue methionine has the sequence (SEQ ID NO: 15):

```
MGLNRFMRAM MVVFITANCI TINPDIIFAA TDSEDSSLNT DEWEEEKTEE      50
QPSEVNTGPR YETAREVSSR DIEELEKSNK VKNTNKADLI AMLKAKAEKG     100
GS.
```

These sequences may then serve as the basis for modification by deletion (actual or functional) of the PEST motif and any existing hydrophobic motifs. Thus, a modified ActA of the invention may comprise or consist of the following sequence (dashes indicate deletions and bold text indicates substitutions) (SEQ ID NO: 16):

```
VGLNRFMRAM MVVFITANCI TINPDIIFAA TDSEDSSLNT DEWEEE----      50
---------- YETAREVSSR DIEELEKSNK VKNTNKADQDNKRKAKAEKG    100
```

In this sequence, the first residue is depicted as a valine; the polypeptide is synthesized by *Listeria* with a methionine in this position. Thus, a modified may also comprise or consist of the following sequence (SEQ ID NO: 17):

```
MGLNRFMRAM MVVFITANCI TINPDIIFAA TDSEDSSLNT DEWEEE----    50

---------- YETAREVSSR DIEELEKSNK VKNTNKADQDNKRKAKAEKG    100
```

In these cases, the substitution with QDNKR (SEQ ID NO: 9) is optionally included with the deletion of the PEST motif, and as above, these constructs of the present invention may also comprise one or more additional, non-ActA, residues lying between the C-terminal residue of the modified ActA and the antigen sequence.

Alternatively, antigen sequence(s) are preferably expressed as a single polypeptide fused to a modified amino-terminal portion of the *L. monocytogenes* LLO protein which permits expression and secretion of a fusion protein from the bacterium within the vaccinated host. In these embodiments, the antigenic construct may be a polynucleotide comprising a promoter operably linked to a nucleic acid sequence encoding a fusion protein, wherein the fusion protein comprises (a) modified LLO and (b) one or more antigenic epitopes to be expressed as a fusion protein following the modified LLO sequence. The LLO signal sequence is MKKIMLVFIT LILVSLPIAQ QTEAK (SEQ ID NO: 18). In some embodiments, the promoter is hly promoter.

In some embodiments, the modified LLO comprises a modified form of about the first 441 amino acids of LLO, referred to herein as LLO-N441. LLO-N441 has the following sequence (SEQ ID NO: 19):

```
        10         20         30         40         50         60
MKKIMLVFIT LILVSLPIAQ QTEAKDASAF NKENSISSMA PPASPPASPK TPIEKKHADE 70         80         90        100        110        120
IDKYIQGLDY NKNNVLVYHG DAVTNVPPRK GYKDGNEYIV VEKKKKSINQ NNADIQVVNA 130        140        150        160        170        180
ISSLTYPGAL VKANSELVEN QPDVLPVKRD SLTLSIDLPG MTNQDNKIVV KNATKSNVNN 190        200        210        220        230        240
AVNTLVERWN EKYAQAYPNV SAKIDYDDEM AYSESQLIAK FGTAFKAVNN SLNVNFGAIS 250        260        270        280        290        300
EGKMQEEVIS FKQIYYNVNV NEPTRPSRFF GKAVTKEQLQ ALGVNAENPP AYISSVAYGR 310        320        330        340        350        360
QVYLKLSTNS HSTKVKAAFD AAVSGKSVSG DVELTNIIKN SSFKAVIYGG SAKDEVQIID 370        380        390        400        410        420
GNLGDLRDIL KKGATFNRET PGVPIAYTTN FLKDNELAVI KNNSEYIETT SKAYTDGKIN 430        440
IDHSGGYVAQ FNISWDEVNY D
```

In this sequence, the PEST motif is represented by KENSISSMA PPASPPASPK (SEQ ID NO: 6). This may be functionally deleted by replacement with the following sequence (dashes indicate deletions and bold text indicates substitutions):

KE-------, or by its complete deletion. This is intended to be exemplary only.

As sequences encoded by one organism are not necessarily codon optimized for optimal expression in a chosen vaccine platform bacterial strain, the present invention also provides nucleic acids that are altered by codon optimized for expressing by a bacterium such as *L. monocytogenes*.

In various embodiments, at least one percent of any non-optimal codons are changed to provide optimal codons, more normally at least five percent are changed, most normally at least ten percent are changed, often at least 20% are changed, more often at least 30% are changed, most often at least 40%, usually at least 50% are changed, more usually at least 60% are changed, most usually at least 70% are changed, optimally at least 80% are changed, more optimally at least 90% are changed, most optimally at least 95% are changed, and conventionally 100% of any non-optimal codons are codon-optimized for *Listeria* expression (Table 2).

TABLE 2

Optimal codons for expression in Listeria.

| Amino Acid | A | R | N | D | C | Q | E | G | H | I |
|---|---|---|---|---|---|---|---|---|---|---|
| Optimal Listeria codon | GCA | CGU | AAU | GAU | UGU | CAA | GAA | GGU | CAU | AUU |
| Amino Acid | L | K | M | F | P | S | T | W | Y | V |
| Optimal Listeria codon | UUA | AAA | AUG | UUU | CCA | AGU | ACA | UGG | UAU | GUU |

TABLE 2-continued

The invention supplies a number of *Listeria* species and strains for making or engineering a bacterium of the present invention. The *Listeria* of the present invention is not to be limited by the species and strains disclosed in Table 3.

TABLE 3

Strains of *Listeria* suitable for use in the present invention,
e.g., as a vaccine or as a source of nucleic acids.

| | |
|---|---|
| *L. monocytogenes* 10403S wild type. | Bishop and Hinrichs (1987) J. Immunol. 139: 2005-2009; Lauer, et al. (2002) J. Bact. 184: 4177-4186. |
| *L. monocytogenes* DP-L4056 (phage cured). The prophage-cured 10403S strain is designated DP-L4056. | Lauer, et al. (2002) J. Bact. 184: 4177-4186. |
| *L. monocytogenes* DP-L4027, which is DP-L2161, phage cured, deleted in hly gene. | Lauer, et al. (2002) J. Bact. 184: 4177-4186; Jones and Portnoy (1994) Infect. Immunity 65: 5608-5613. |
| *L. monocytogenes* DP-L4029, which is DP-L3078, phage cured, deleted in ActA. | Lauer, et al. (2002) J. Bact. 184: 4177-4186; Skoble, et al. (2000) J. Cell Biol. 150: 527-538. |
| *L. monocytogenes* DP-L4042 (delta PEST) | Brockstedt, et al. (2004) Proc. Natl. Acad. Sci. USA 101: 13832-13837; supporting information. |
| *L. monocytogenes* DP-L4097 (LLO-S44A). | Brockstedt, et al. (2004) Proc. Natl. Acad. Sci. USA 101: 13832-13837; supporting information. |
| *L. monocytogenes* DP-L4364 (delta lplA; lipoate protein ligase). | Brockstedt, et al. (2004) Proc. Natl. Acad. Sci. USA 101: 13832-13837; supporting information. |
| *L. monocytogenes* DP-L4405 (delta inlA). | Brockstedt, et al. (2004) Proc. Natl. Acad. Sci. USA 101: 13832-13837; supporting information. |
| *L. monocytogenes* DP-L4406 (delta inlB). | Brockstedt, et al. (2004) Proc. Natl. Acad. Sci. USA 101: 13832-13837; supporting information. |
| *L. monocytogenes* CS-L0001 (delta ActA-delta inlB). | Brockstedt, et al. (2004) Proc. Natl. Acad. Sci. USA 101: 13832-13837; supporting information. |
| *L. monocytogenes* CS-L0002 (delta ActA-delta lplA). | Brockstedt, et al. (2004) Proc. Natl. Acad. Sci. USA 101: 13832-13837; supporting information. |
| *L. monocytogenes* CS-L0003 (L461T-delta lplA). | Brockstedt, et al. (2004) Proc. Natl. Acad. Sci. USA 101: 13832-13837; supporting information. |
| *L. monocytogenes* DP-L4038 (delta ActA-LLO L461T). | Brockstedt, et al. (2004) Proc. Natl. Acad. Sci. USA 101: 13832-13837; supporting information. |
| *L. monocytogenes* DP-L4384 (S44A-LLO L461T). | Brockstedt, et al. (2004) Proc. Natl. Acad. Sci. USA 101: 13832-13837; supporting information. |
| *L. monocytogenes*. Mutation in lipoate protein ligase (LplA1). | O'Riordan, et al. (2003) Science 302: 462-464. |
| *L. monocytogenes* DP-L4017 (10403S hly (L461T) point mutation in hemolysin gene. | U.S. Provisional Pat. application Ser. No. 60/490,089 filed Jul. 24, 2003. |
| *L. monocytogenes* EGD. | GenBank Acc. No. AL591824. |
| *L. monocytogenes* EGD-e. | GenBank Acc. No. NC_003210. ATCC Acc. No. BAA-679. |
| *L. monocytogenes* strain EGD, complete genome, segment 3/12 | GenBank Acc. No. AL591975 |
| *L. monocytogenes*. | ATCC Nos. 13932; 15313; 19111-19120; 43248-43251; 51772-51782. |
| *L. monocytogenes* DP-L4029 deleted in uvrAB. | U.S. Provisional Pat. application Ser. No. 60/541,515 filed Feb. 2, 2004; U.S. Provisional Pat. application Ser. No. 60/490,080 filed Jul. 24, 2003. |
| *L. monocytogenes* DP-L4029 deleted in uvrAB treated with a psoralen. | U.S. Provisional Pat. application Ser. No. 60/541,515 filed Feb. 2, 2004. |
| *L. monocytogenes* ActA-/inlB- double mutant. | Deposited with ATCC on Oct. 3, 2003. Acc. No. PTA-5562. |
| *L. monocytogenes* lplA mutant or hly mutant. | U.S. patent application No. 20040013690 of Portnoy, et al. |
| *L. monocytogenes* DAL/DAT double mutant. | U.S. patent application No. 20050048081 of Frankel and Portnoy. |
| *L. monocytogenes* str. 4b F2365. | GenBank Acc. No. NC_002973. |
| *Listeria ivanovii* | ATCC No. 49954 |
| *Listeria innocua* Clip11262. | GenBank Acc. No. NC_003212; AL592022. |
| *Listeria innocua*, a naturally occurring hemolytic strain containing the PrfA-regulated virulence gene cluster. | Johnson, et al. (2004) Appl. Environ. Microbiol. 70: 4256-4266. |
| *Listeria seeligeri*. | Howard, et al. (1992) Appl. Evrion. Microbiol. 58: 709-712. |
| *Listeria innocua* with *L. monocytogenes* pathogenicity island genes. | Johnson, et al. (2004) Appl. Environ. Microbiol. 70: 4256-4266. |
| *Listeria innocua* with *L. monocytogenes* internalin A gene, e.g., as a plasmid or as a genomic nucleic acid. | See, e.g., Lingnau, et al. (1995) Infection Immunity 63: 3896-3903; Gaillard, et al. (1991) Cell 65: 1127-1141). |

The present invention encompasses reagents and methods that comprise the above Listerial strains, as well as these strains that are modified, e.g., by a plasmid and/or by genomic integration, to contain a nucleic acid encoding one of, or any combination of, the following genes: hly (LLO; listeriolysin); iap (p60); inlA; inlB; inlC; dal (alanine racemase); daaA (dat; D-amino acid aminotransferase); plcA; plcB; ActA; or any nucleic acid that mediates growth, spread, breakdown of a single walled vesicle, breakdown of a double walled vesicle, binding to a host cell, uptake by a host cell. The present invention is not to be limited by the particular strains disclosed above.

Therapeutic Compositions.

The bacterial compositions described herein can be administered to a host, either alone or in combination with a pharmaceutically acceptable excipient, in an amount sufficient to induce an appropriate immune response. The immune response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression. The vaccines of the present invention can be stored, e.g., frozen, lyophilized, as a suspension, as a cell paste, or complexed with a solid matrix or gel matrix.

In certain embodiments, after the subject has been administered an effective dose of a first vaccine to prime the immune response, a second vaccine is administered. This is referred to in the art as a "prime-boost" regimen. In such a regimen, the compositions and methods of the present invention may be used as the "prime" delivery, as the "boost" delivery, or as both a "prime" and a "boost." Any number of "boost" immunizations can be delivered in order to maintain the magnitude or effectiveness of a vaccine-induced immune response.

As an example, a first vaccine comprised of killed but metabolically active Listeria that encodes and expresses the antigen polypeptide(s) may be delivered as the "prime," and a second vaccine comprised of attenuated (live or killed but metabolically active) Listeria that encodes the antigen polypeptide(s) may be delivered as the "boost." It should be understood, however, that each of the prime and boost need not utilize the methods and compositions of the present invention. Rather, the present invention contemplates the use of other vaccine modalities together with the bacterial vaccine methods and compositions of the present invention. The following are examples of suitable mixed prime-boost regimens: a DNA (e.g., plasmid) vaccine prime/bacterial vaccine boost; a viral vaccine prime/bacterial vaccine boost; a protein vaccine prime/bacterial vaccine boost; a DNA prime/bacterial vaccine boost plus protein vaccine boost; a bacterial vaccine prime/DNA vaccine boost; a bacterial vaccine prime/viral vaccine boost; a bacterial vaccine prime/protein vaccine boost; a bacterial vaccine prime/bacterial vaccine boost plus protein vaccine boost; etc. This list is not meant to be limiting The prime vaccine and boost vaccine may be administered by the same route or by different routes. The term "different routes" encompasses, but is not limited to, different sites on the body, for example, a site that is oral, non-oral, enteral, parenteral, rectal, intranode (lymph node), intravenous, arterial, subcutaneous, intradermal, intramuscular, intratumor, peritumor, infusion, mucosal, nasal, in the cerebrospinal space or cerebrospinal fluid, and so on, as well as by different modes, for example, oral, intravenous, and intramuscular.

An effective amount of a prime or boost vaccine may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration of a vaccine or vaccines in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

In certain embodiments, administration of the boost vaccination can be initiated at about 5 days after the prime vaccination is initiated; about 10 days after the prime vaccination is initiated; about 15 days; about 20 days; about 25 days; about 30 days; about 35 days; about 40 days; about 45 days; about 50 days; about 55 days; about 60 days; about 65 days; about 70 days; about 75 days; about 80 days; about 6 months, and about 1 year after administration of the prime vaccination is initiated. Preferably one or both of the prime and boost vaccination comprises delivery of a composition of the present invention.

A "pharmaceutically acceptable excipient" or "diagnostically acceptable excipient" includes but is not limited to, sterile distilled water, saline, phosphate buffered solutions, amino acid based buffers, or bicarbonate buffered solutions. An excipient selected and the amount of excipient used will depend upon the mode of administration. Administration may be oral, intravenous, subcutaneous, dermal, intradermal, intramuscular, mucosal, parenteral, intraorgan, intralesional, intranasal, inhalation, intraocular, intramuscular, intravascular, intranodal, by scarification, rectal, intraperitoneal, or any one or combination of a variety of well-known routes of administration. The administration can comprise an injection, infusion, or a combination thereof.

Administration of the vaccine of the present invention by a non-oral route can avoid tolerance. Methods are known in the art for administration intravenously, subcutaneously, intradermally, intramuscularly, intraperitoneally, orally, mucosally, by way of the urinary tract, by way of a genital tract, by way of the gastrointestinal tract, or by inhalation.

An effective amount for a particular patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

The vaccines of the present invention can be administered in a dose, or dosages, where each dose comprises at least 100 bacterial cells/kg body weight or more; in certain embodiments 1000 bacterial cells/kg body weight or more; normally at least 10,000 cells; more normally at least 100,000 cells; most normally at least 1 million cells; often at least 10 million cells; more often at least 100 million cells; typically at least 1 billion cells; usually at least 10 billion cells; conventionally at least 100 billion cells; and sometimes at least 1 trillion cells/kg body weight. The present invention provides the above doses where the units of bacterial administration is colony forming units (CFU), the equivalent of CFU prior to psoralen treatment, or where the units are number of bacterial cells.

The vaccines of the present invention can be administered in a dose, or dosages, where each dose comprises between $10^7$ and $10^8$ bacteria per 70 kg body weight (or per 1.7 square meters surface area; or per 1.5 kg liver weight); $2 \times 10^7$ and $2 \times 10^8$ bacteria per 70 kg body weight (or per 1.7 square meters surface area; or per 1.5 kg liver weight); $5 \times 10^7$ and $5 \times 10^8$ bacteria per 70 kg body weight (or per 1.7 square meters surface area; or per 1.5 kg liver weight); $10^8$ and $10^9$ bacteria per 70 kg body weight (or per 1.7 square meters surface area; or per 1.5 kg liver weight); between $2.0 \times 10^8$ and $2.0 \times 10^9$ bacteria per 70 kg (or per 1.7 square meters surface area, or per 1.5 kg liver weight); between $5.0 \times 10^8$ to $5.0 \times 10^9$ bacteria per 70 kg (or per 1.7 square meters surface area, or per 1.5 kg liver weight); between $10^9$ and $10^{10}$ bacteria per 70 kg (or per 1.7 square meters surface area, or per 1.5 kg liver weight); between $2 \times 10^9$ and $2 \times 10^{10}$ bacteria per 70 kg (or per 1.7 square meters surface area, or per 1.5 kg liver weight); between $5 \times 10^9$ and $5 \times 10^{10}$ bacteria per 70 kg (or per 1.7 square meters surface area, or per 1.5 kg liver weight); between $10^{11}$ and $10^{12}$ bacteria per 70 kg (or per 1.7 square meters surface area, or per 1.5 kg liver weight); between $2 \times 10^{11}$ and $2 \times 10^{12}$ bacteria per 70 kg (or per 1.7 square meters surface area, or per 1.5 kg liver weight); between $5 \times 10^{11}$ and $5 \times 10^{12}$ bacteria per 70 kg (or per 1.7 square meters surface area, or per 1.5 kg liver weight); between $10^{12}$ and $10^{13}$ bacteria per 70 kg (or per 1.7 square meters surface area); between $2 \times 10^{12}$ and $2 \times 10^{13}$ bacteria per 70 kg (or per 1.7 square meters surface area, or per 1.5 kg liver weight); between $5 \times 10^{12}$ and $5 \times 10^{13}$ bacteria per 70 kg (or per 1.7 square meters surface area, or per 1.5 kg liver weight); between $10^{13}$ and $10^{14}$ bacteria per 70 kg (or per 1.7 square meters surface area, or per 1.5 kg liver weight); between $2 \times 10^{13}$ and $2 \times 10^{14}$ bacteria per 70 kg (or per 1.7 square meters surface area, or per 1.5 kg liver weight); $5 \times 10^{13}$ and $5 \times 10^{14}$ bacteria per 70 kg (or per 1.7 square meters surface area, or per 1.5 kg liver weight); between $10^{14}$ and $10^{15}$ bacteria per 70 kg (or per 1.7 square meters surface area, or per 1.5 kg liver weight); between $2 \times 10^{14}$ and $2 \times 10^{15}$ bacteria per 70 kg (or per 1.7 square meters surface area, or per 1.5 kg liver weight); and so on, wet weight.

Also provided is one or more of the above doses, where the dose is administered by way of one injection every day, one injection every two days, one injection every three days, one injection every four days, one injection every five days, one injection every six days, or one injection every seven days, where the injection schedule is maintained for, e.g., one day only, two days, three days, four days, five days, six days, seven days, two weeks, three weeks, four weeks, five weeks, or longer. The invention also embraces combinations of the above doses and schedules, e.g., a relatively large initial bacterial dose, followed by relatively small subsequent doses, or a relatively small initial dose followed by a large dose.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

The present invention encompasses a method of administering *Listeria* that is oral. Also provided is a method of administering *Listeria* that is intravenous. Moreover, what is provided is a method of administering *Listeria* that is oral, intramuscular, intravenous, intradermal and/or subcutaneous. The invention supplies a *Listeria* bacterium, or culture or suspension of *Listeria* bacteria, prepared by growing in a medium that is meat based, or that contains polypeptides derived from a meat or animal product. Also supplied by the present invention is a *Listeria* bacterium, or culture or suspension of *Listeria* bacteria, prepared by growing in a medium that does not contain meat or animal products, prepared by growing on a medium that contains vegetable polypeptides, prepared by growing on a medium that is not based on yeast products, or prepared by growing on a medium that contains yeast polypeptides.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

Additional agents which are beneficial to raising a cytolytic T cell response may be used as well. Such agents are termed herein carriers. These include, without limitation, B7 costimulatory molecule, interleukin-2, interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Carriers for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen-presenting cells include astrocytes, follicular cells, endothelium and fibroblasts. The carrier can be a bacterial cell that is transformed to express the polypeptide or to deliver a polynucleoteide which is subsequently expressed in cells of the vaccinated individual. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryl lipid A, lipoteichoic acid, imiquimod, resiquimod, and other like immune modulators such as cyclic dinucleotide STING agonists including c-di-GMP, c-di-AMP, c-di-IMP, and c-AMP-GMP, used separately or in combination with the described compositions are also potential adjuvants. Other representative examples of adjuvants include the synthetic adjuvant QS-21 comprising a homogeneous saponin purified from the bark of *Quillaja saponaria* and *Corynebacterium parvum* (McCune et al., Cancer, 1979; 43:1619). It will be understood that the adjuvant is subject to optimization. In other words, the skilled artisan can engage in routine experimentation to determine the best adjuvant to use.

An effective amount of a therapeutic agent is one that will decrease or ameliorate the symptoms normally by at least 10%, more normally by at least 20%, most normally by at least 30%, typically by at least 40%, more typically by at least 50%, most typically by at least 60%, often by at least 70%, more often by at least 80%, and most often by at least 90%, conventionally by at least 95%, more conventionally by at least 99%, and most conventionally by at least 99.9%.

The reagents and methods of the present invention provide a vaccine comprising only one vaccination; or comprising a first vaccination; or comprising at least one booster vaccination; at least two booster vaccinations; or at least three booster vaccinations. Guidance in parameters for booster vaccinations is available. See, e.g., Marth (1997) Biologicals 25:199-203; Ramsay, et al. (1997) Immunol. Cell Biol. 75:382-388; Gherardi, et al. (2001) Histol. Histopathol. 16:655-667; Leroux-Roels, et al. (2001) ActA Clin. Belg. 56:209-219; Greiner, et al. (2002) Cancer Res. 62:6944-6951; Smith, et al. (2003) J. Med. Virol. 70:Suppl.1:S38-541; Sepulveda-Amor, et al. (2002) Vaccine 20:2790-2795).

Formulations of therapeutic agents may be prepared for storage by mixing with physiologically acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

EXAMPLES

The following examples serve to illustrate the present invention. These examples are in no way intended to limit the scope of the invention.

Example 1

FIG. 2 depicts various modifications to the sequences of ActA and LLO tested in the following examples.

With regard to the modifiedActA sequence, the parent ActA sequence was truncated at residue 100, and was extended by two residues added by inclusion of a BamH1 site, shown in the FIG as residues G101 and S102. Modifications to the PEST sequence involved the deletions shown in the figure, and an optional substitution of the hydrophobic motif LIAML (SEQ ID NO: 8) to QDNKR (SEQ ID NO: 9) is also depicted. With regard to the modified LLO sequence, the parent LLO sequence was truncated at residue 441. Modifications to the PEST sequence involved the deletions shown in the figure. In each case, the depicted signal peptide/secretion chaperone elements are functionally linked in-frame to selected antigen sequences.

Example 2

Figure 3:
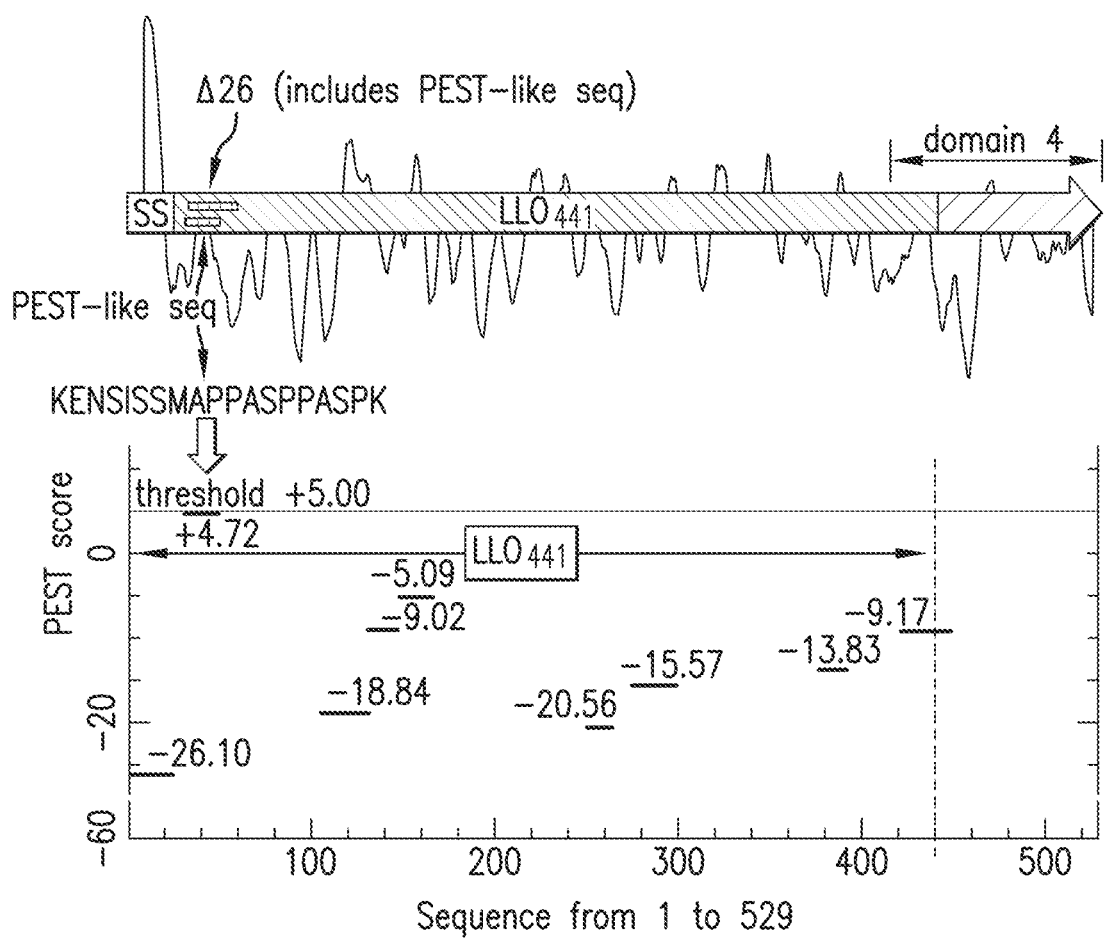
FIG. 3 depicts the location of a PEST motif (SEQ ID NO: 6) in the LLO sequence, scored using the epestfind algorithm.

FIG. 3 depicts the location of a PEST motif in the LLO sequence, scored using the epestfind algorithm. A single motif having a score of +4.72 was modified as noted above in Example 1. Also shown in the top of the figure is the hydropathy plot. A number of hydrophiobic motifs are shown (peaks rising above the sequence schematic) which may be modified as described herein.

Figure 4:
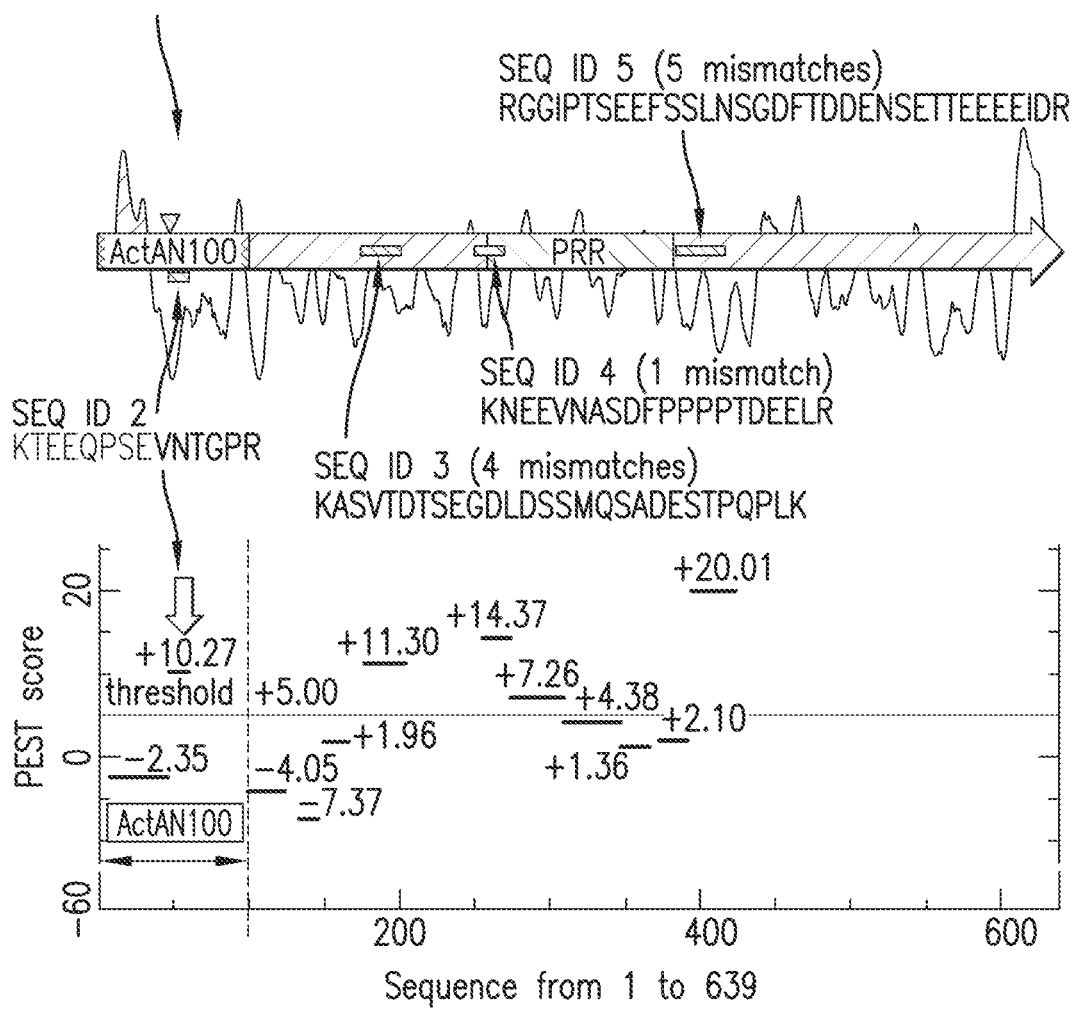
FIG. 4 depicts four PEST motifs (SEQ ID NOS 2-5) in the ActA sequence, scored using the epestfind algorithm. "Mutant 40" sequences are disclosed as SEQ ID NOS 45-46, respectively, in order of appearance.

Similarly, FIG. 4 depicts four PEST motifs in the ActA sequence, scored using the epestfind algorithm. The first of these motifs has a score of +10.27, and was modified as noted above in Example 1. The remaining PEST motifs were deleted by truncating the ActA sequence at residue 100. Also shown in the top of the figure is the hydropathy plot. The hydrophobic motif LIAML (SEQ ID NO: 8) is apparent as the peak rising above the sequence schematic in ActAN100.

Example 3

Figure 5:
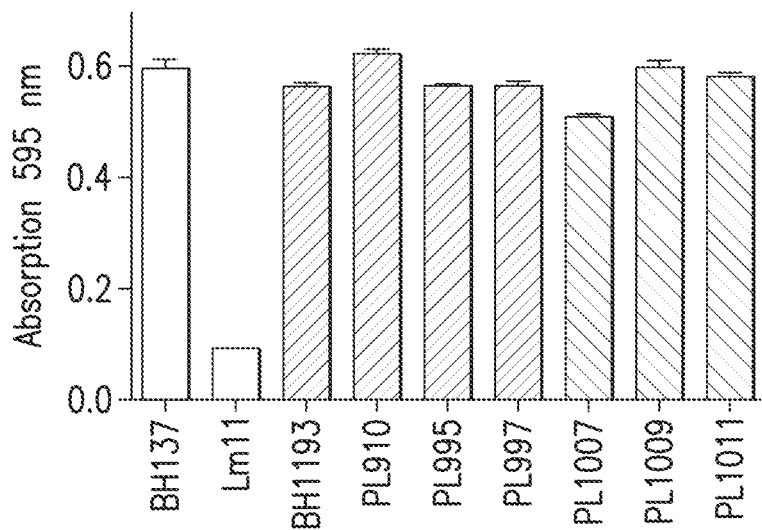
FIG. 5 depicts the results of a B3Z T-cell activation assay following immunization with *Listeria monocytogenes* expressing fusion constructs having various modified ActA and LLO fusion partners. "QDNKR" is disclosed as SEQ ID NO: 9.

FIG. 5 shows the results of a B3Z T-cell activation assay following immunization with the constructs noted in the figure. In each antigenic construct, HIVgag was expreseed fused to SIINFEKL ("SL8") epitope tag (SEQ ID NO: 20) and inserted into the genome of the host Lm ΔactA ΔinlB vaccine strain. DC2.4 cells were infected with the selected strains, and incubated with the $OVA_{257-264}$-specific T cell hybridoma, B3Z. Presentation of SIINFEKL epitope (SEQ ID NO: 20) on H-2 $K^b$ class I molecules was assessed by measuring β-galactosidase expression using a chromogenic substrate. As noted in the figure, deletion of the PEST sequence had a positive or neutral effect on the assay results.

Example 4

Figure 6A:
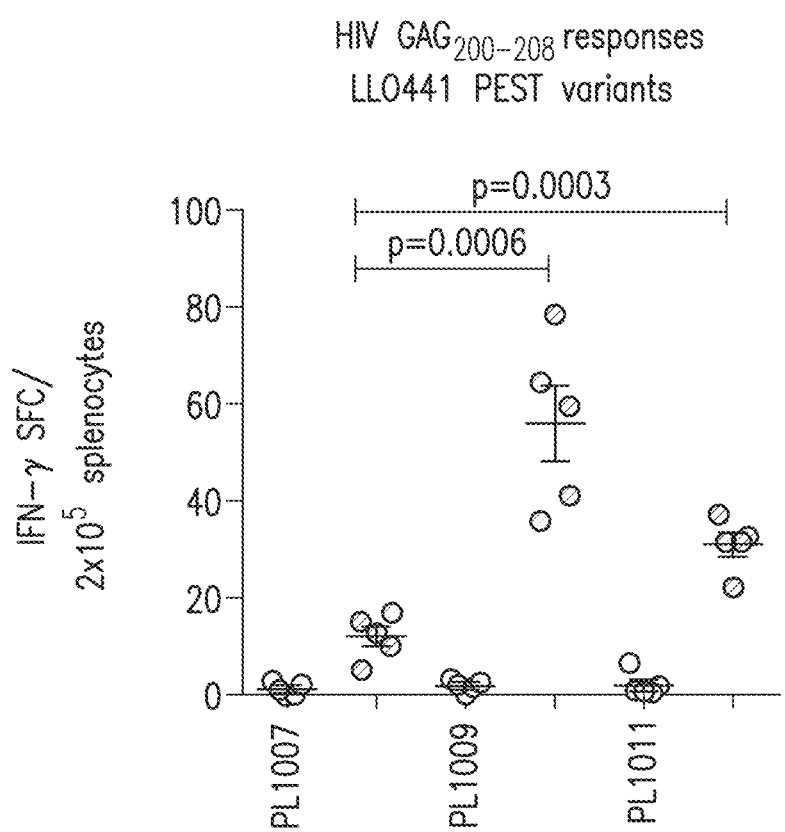
FIG. 6 depicts responses from certain LLO441 (A) and ActAN100 (B) vaccine strains.
Figure 6B:
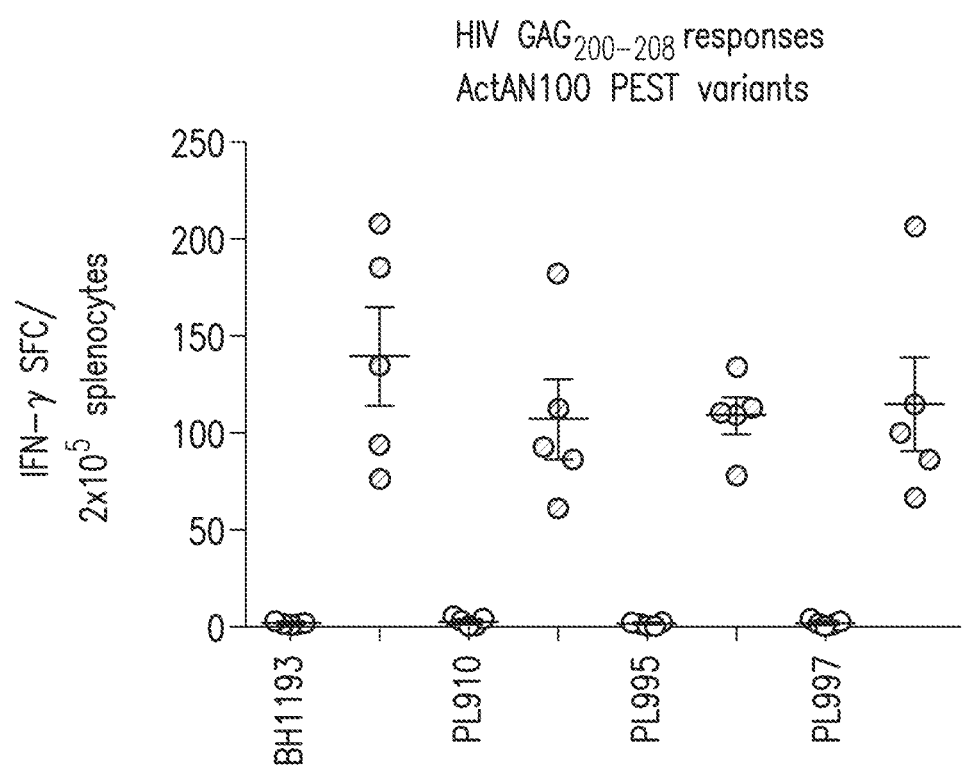

FIG. 6 shows responses from the LL0441 (A) and ActAN100 vaccine strains. BALB/c mice were vaccinated once intravenously with $5×10^6$ colony forming units (cfu) with indicated vaccine strain containing an N-terminal fusion partner that contained a PEST motif or were deleted of the PEST motif, in order to directly compare the immunogenicity of these isogenic strains that differed only in the composition of the N-terminal LLO or ActA fusion partner. At the peak of the Lm vaccine response at 7 days post vaccination, the spleens of mice were harvested and the HIV-Gag CD8 T cell responses specific for the H2 $K^d$-restricted HIV $Gag_{197-205}$ epitope AMQMLKETI (SEQ ID NO: 21) by IFN-γ ELISpot assay performed with lymphocytes isolated from whole mouse blood using Lympholyte-Mammal (Cedarlane Labs, Burlington, N.C.) and a murine IFN-γ ELISpot pair (BD Biosciences, San Jose, Calif.). At the termination of the experiments, ELISpot assays were performed on splenocytes. $2×10^5$ cells/well were incubated with the appropriate peptide overnight at 37° C. in anti-murine IFN-γ coated ELISpot plate (Millipore, Billerica, Mass.). Cells were incubated with no peptide as a negative control. Murine ELISpots were developed using alkaline phosphatase detection reagents (Invitrogen, Carlsbad, Calif.) and scanned and quantified using Immunospot plate reader and software (CTL Ltd, Cleveland, Ohio).

Mice vaccinated with Lm vaccine strains containing PEST LLO$_{441}$ N-terminal secretion/chaperone elements generated HIV Gag-specific CD8 T cell responses that were higher than mice vaccinated with isogenic Lm vaccine strains containing LLO$_{441}$ N-terminal secretion/chaperone elements with PEST motifs. Mice vaccinated with Lm vaccine strains containing PEST ActAN100 N-terminal secretion/chaperone elements generated HIV Gag-specific CD8 T cell responses that were at least equivalent to mice vaccinated with isogenic Lm vaccine strains containing ActAN100 N-terminal secretion/chaperone elements with PEST mot Example 5

FIG. 7 depicts several alternative substitutions and deletions for use in deleting the PEST motif, using ActA as a model system. Substitution of any of five P, E, S and T amino acids (E50, P52, S53, E54, T57) in the ActAN100 sequence to a positively charged residue (R, K, or H) was sufficient to abrogate a positive score using the pestfinder algorithm.

Figure 8:
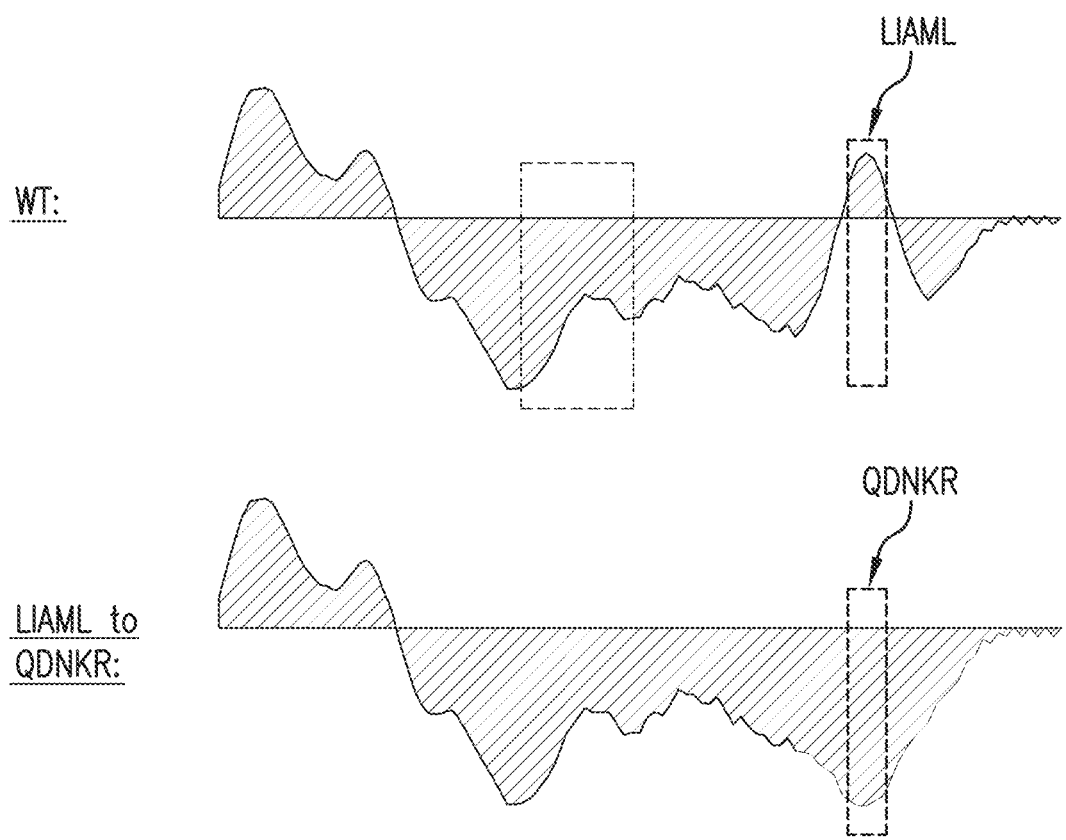
FIG. 8. depicts the result of modifying the hydrophobic motif LIAML (SEQ ID NO: 8) on the a hydropathy plot of ActAN100. "QDNKR" is disclosed as SEQ ID NO: 9.

FIG. 8. depicts in more detail the result of modifying the hydrophobic motif LIAML (SEQ ID NO: 8) on the resulting hydropathy plot. Nonconservative substitution to QDNKR (SEQ ID NO: 9) was sufficient to remove the hydrophobic nature of this sequence.

Example 6

ActA-N100 (MGLNRFMRAM MVVFITANCI TINPDIIFAA TDSEDSSLNT DEWEEEKTE QPSEVNTGPR YETAREVSSR DIEELEKSNK VKNTNKADLI AMLKAKAEKG gs (SEQ ID NO: 22)) and a modified form thereof in which the PEST motif has been deleted and containing the nonconservative QDNKR (SEQ ID NO: 9) substitution (MGLNRFMRAM MVVFITANCI TINPDIIFAA TDSEDSSLNT DEWEEEYETA REVSSRDIEE LEKSNK-VKNT NKADQDNKRK AKAEKg1 (SEQ ID NO: 23); referred to herein as ActA-N100*) were used to prepare a fusion construct with human mesothelin residues 35-621 (the lowercase residues above were included between the ActA sequence and the mesothlin sequence as a result of the restriction site used to prepare the in-frame fusion). The construct was integrated at the chromosomal tRNA locus of *Listeria monocytogenes* ΔactAΔinlB. Balb/c mice were challenged with 2×10$^5$ CT-26 tumor cells that express human mesothelin on Day 0. Mice were therapeutically vaccinated on day 4 and day 17 with *Listeria* vaccine strains. The results of this experiment are depicted in FIG. 9 as percent survival of the vaccinated animals. As shown, here was no difference in efficacy between ActA-N100 vs ActA-N100* based vaccines.

Example 7

Similar *Listeria monocytogenes* ΔactAΔinlB to those of Example 6 were prepared in which the mesothelin antigenic sequence was replaced by 5 copies of an EGFRvIII$_{20-40}$ sequence and NY-ESO-1$_{1-165}$. The DNA and protein sequences used in the antigenic construct are as follows (lowercase, not underlined: actA promoter; lowercase, underlined: restriction sites; uppercase, bold: ActAN100* sequence; uppercase underlined: EGFRvIII20-40×5; uppercase, italic: NY-ESO-1(1-165) (each EGFRvIII$_{20-40}$ repeat is double underlined in the peptide sequence, and the leading Val codon is used to encode Met):

ggtaccgggaagcagttggggttaactgattaacaaatgttagagaaaaattaattctccaagt gatattcttaaaataattcatgaatatttttcttatattagctaattaagaagataattaact gctaatccaattttaacggaataaattagtgaaaatgaaggccgaattttccttgttctaaaa aggttgtattagcgtatcacgaggagggagtataaGTGGGATTAAATAGATTTATGCGTGCGAT

GATGGTAGTTTTCATTACTGCCAACTGCATTACGATTAACCCCGACATAATATTTGCAGCGACA

GATAGCGAAGATTCCAGTCTAAACACAGATGAATGGGAAGAAGAATACGAAACTGCACGTGAAG

TAAGTTCACGTGATATTGAGGAACTAGAAAAATCGAATAAAGTGAAAAATACGAACAAAGCAGA

CCAAGATAATAAACGTAAAGCAAAAGCAGAGAAAGGTggatcc<u>GCAAGCAAAGTATTGCCAGCT</u>

<u>AGTCGTGCATTAGAGGAGAAAAAGGGGAATTACGTGGTGACGGATCATGGATCGTGTGCCGATG</u>

<u>GCTCAGTAAAGACTAGTGCGAGCAAAGTGGCCCCTGCATCACGAGCACTTGAAGAGAAAAAAGG</u>

<u>AAACTATGTTGTGACCGATCATGGTAGCTGCGGAGATGGTTCAATTAAATTATCAAAAGTCTTA</u>

<u>CCAGCATCTAGAGCTTTAGAGGAAAAGAAGGGTAACTATGTCGTAACAGATCATGGAAGTTGTG</u>

<u>CTGACGGAAGTGTTAAAGCGTCGAAAGTAGCTCCAGCTTCTCGCGCATTAGAAGAAAAGAAAGG</u>

<u>CAATTATGTTGTAACAGACCATGGTAGTTGTGGTGATGGCTCGATCAAATTGTCAAAAGTTCTA</u>

<u>CCGGCTTCTCGTGCGCTAGAAGAGAAGAAAGGAAATTACGTAGTTACAGACCACGGCTCTTGCG</u>

<u>CGGATGGI TCCGTTAAA</u>caattg*ATGCAAGCTGAAGGAAGAGGAACTGGGGGTAGTACAGGAGA*

*TGCAGATGGCCCTGGCGGACCGGGTATTCCTGATGGACCAGGGGGTAATGCGGGTGGGCCAGGC*

*GAAGCAGGTGCTACAGGCGGTAGAGGGCCACGAGGGGCAGGAGCAGCGAGAGCTTCTGGACCAG*

*GTGGTGGCGCTCCACGCGGTCCGCATGGTGGTGCAGCGTCCGGCTTAAACGGTTGCTGTCGCTG*

-continued

```
TGGAGCTAGAGGACCAGAATCACGTCTTTTAGAGTTCTATTTGGCCATGCCGTTTGCTACGCCT

ATGGAAGCAGAACTAGCACGTCGTAGCTTAGCGCAAGATGCACCTCCATTACCAGTTCCAGGCG

TGTTGTTAAAGGAGTTCACGGTCAGTGGTAACATATTGACAATTCGCCTTACTGCGGCTGACCA

CCGTCAATTACAGCTTAGCATTTCATCTTGTTTACAACAACTTTCGTTACTTATGTGGATCACC

CAATGCTAAggcggccgc (SEQ ID NO: 24)
```

MGLNRFMRAMMVVFITANCITINPDIIFAATDSEDSSLNTDEWEEEYETAREVSSRDIEE

LEKSNKVKNTNKADQDNKRKAKAEKGgsAS<u>KVLPASRALEEKKGNYVVTDHGSCADGSVK</u>

<u>TSASKVAPASRALEEKKGNYVVTDHGSCGDGSIKLSKVLPASRALEEKKGNYVVTDHGSC</u>

<u>ADGSVKASKVAPASRALEEKKGNYVVTDHGSCGDGSIKLSKVLPASRALEEKKGNYVVTD</u>

<u>HGSCADGSVK</u>ql*MQAEGRGTGGSTGDADGPGGPGIPDGPGGNAGGPGEAGATGGRGPRGA*

*GAARASGPGGGAPRGPHGGAASGLNGCCRCGARGPESRLLEFYLAMPFATPMEAELARRS*

*LAQDAPPLPVPGVLLKEFTVSGNILTIRLTAADHRQLQLSISSCLQQLSLLMWITQC*
(SEQ ID NO: 25)

Figure 10:
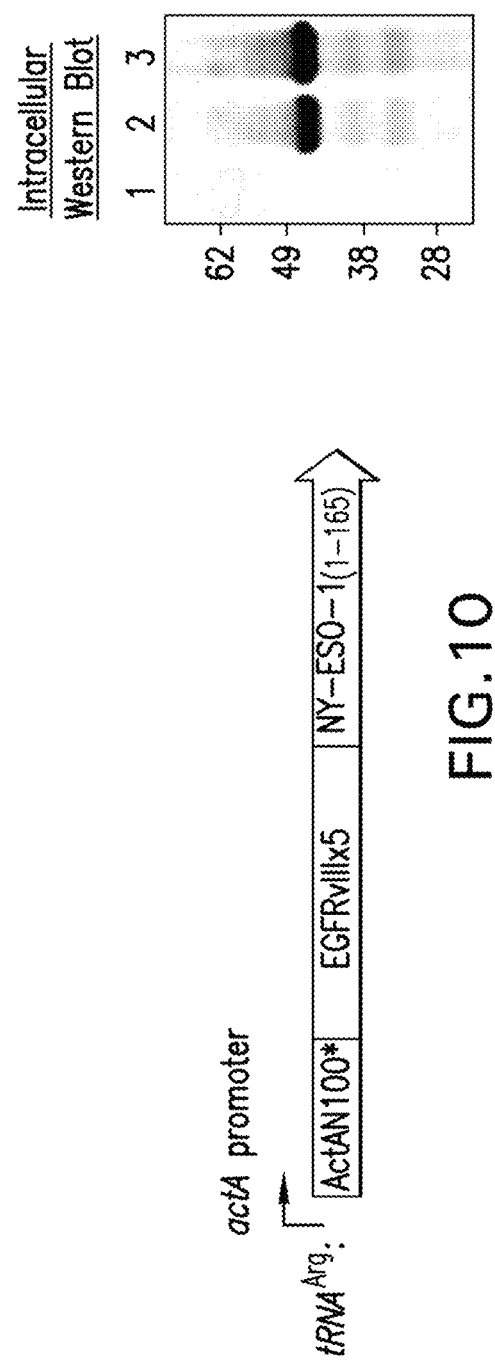
FIG. 10 depicts EGFRvIII$_{20-40}$/NY-ESO-1$_{1-165}$ fusion constructs of the present invention depicted schematically, and expression of the fusion constructs by western blot.

The fusion construct is depicted schematically in FIG. 10, left panel. The mouse dendritic cell line DC2.4 was infected with Lm ΔactA/ΔinlB (FIG. 10, right panel, lane 1), BH3763 (EGFRvIII$_{20-40}$/NY-ESO-1$_{1-165}$), or BH3816 (clinical strain with EGFRvIII$_{20-40}$/NY-ESO-1$_{1-165}$ in which selection markers have been deleted). Seven hours later, cells were washed, lysed, run on SDS-PAGE, and transferred to nitrocellulose. The Western blot was probed with a rabbit polyclonal antibody raised to the amino terminus of the ActA protein and expression level was normalized to the *Listeria* P60 protein, which correlates with bacterial counts in infected cells. High levels of the fusion construct were expressed by both the research and clinical strains.

Figure 11A:
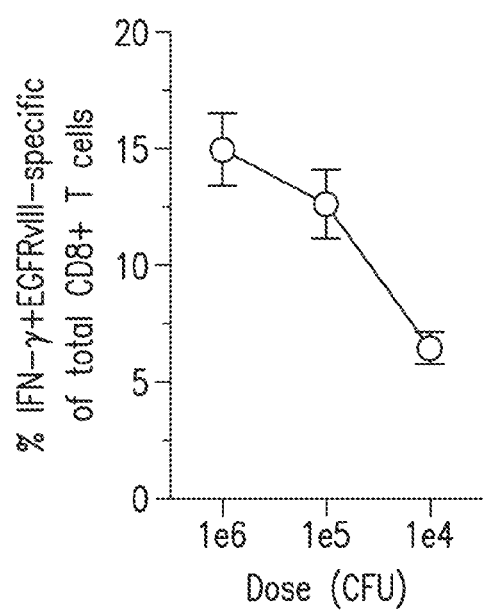
FIG. 11 depicts EGFR-specific T cell responses determined by intracellular cytokine staining, as (A) percent IFN-γ positive EGFRvIII-specific CD8+ T cells; and (B) absolute number of IFN-γ positive EGFRvIII-specific CD8+ T cells per spleen, following immunization with *Listeria* monocytogenes expressing fusion constructs having a modified ActAN100 sequence fused to EGFRvIII$_{20\text{-}40}$/NY-ESO-1$_{1\text{-}165}$.
Figure 11B:
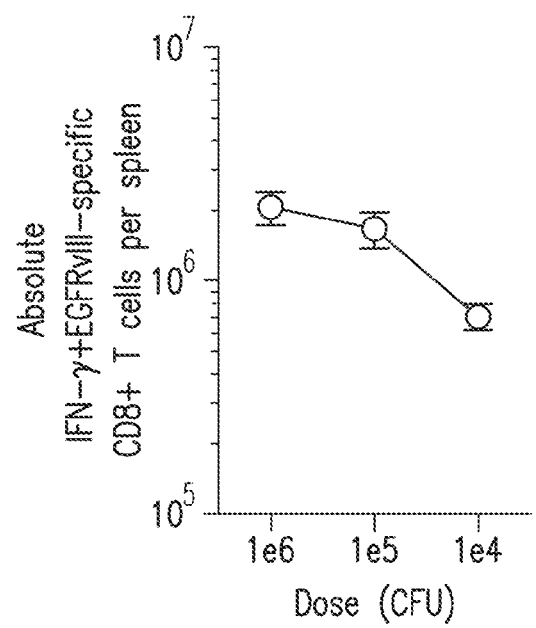

Female B10.Br mice (n=5 per group) were vaccinated intravenously with varying doses of BH3816 (Lm ΔactAΔinlB EGFRvIII-NY-ESO-1). EGFR-specific T cell responses were determined by intracellular cytokine staining, and are depicted in FIG. 11 as (A) percent IFN-γ positive EGFRvIII-specific CD8+ T cells; and (B) absolute number of IFN-γ positive EGFRvIII-specific CD8+ T cells per spleen. Robust EGFR T cell responses were observed. As depicted in FIG. 12, NY-ESO-1-specific CD8+ T cell responses were also observed, as determined by intracellular cytokine staining 7 days after prime vaccination using the defined H-2$^d$ restricted epitope ARGPESRLL (SEQ ID NO: 26).

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A polynucleotide comprising:

(a) a promoter; and (b) a nucleic acid operably linked to the promoter, wherein the nucleic acid encodes a fusion protein comprising:

a polypeptide derived by recombinant modification of a Listerial ActA protein sequence, the Listerial ActA protein sequence in its unmodified form comprising a signal sequence and one or more PEST motifs, the modification comprising removal of each of the PEST motifs by deletion or substitution by one or more residues such that the polypeptide lacks any PEST motif; and a non-Listerial antigen.

2. The polynucleotide of claim 1, wherein the modification comprises truncation of the unmodified Listerial ActA protein sequence at about residue 100 and the removal of each of the PEST motifs from the truncated Listerial ActA protein sequence by deletion or substitution by one or more residues such that the polypeptide lacks any PEST motif.

3. The polynucleotide of claim 1, wherein the polypeptide retains the signal sequence of the Listerial ActA protein sequence in unmodified form.

4. The polynucleotide of claim 1, wherein the modification further comprises:

removal of one or more hydrophobic domains which are not part of the signal sequence of the Listerial ActA protein sequence; and/or substitution of one or more residues within one or more hydrophobic domains which are not part of the signal sequence of the Listerial ActA protein sequence with amino acids which are not hydrophobic.

5. The polynucleotide of claim 1, wherein at least 75% of the sequence KTEEQPSEVNTGP (SEQ ID NO: 1) is deleted from the Listerial ActA protein sequence.

6. The polynucleotide of claim 1, wherein the sequence KTEEQPSEVNTGP (SEQ ID NO: 1) or KTEEQPSEVNTGPR (SEQ ID NO: 2) is deleted from the Listerial ActA protein sequence.

7. The polynucleotide of claim 1, wherein one or more P, E, S, and T residues in the sequence KTEEQPSEVNTGPR (SEQ ID NO: 2) in the Listerial ActA protein sequence is substituted with a residue other than P, E, S, and T.

8. The polynucleotide of claim 7, wherein each P, E, S, and T residue in the sequence KTEEQPSEVNTGPR (SEQ ID NO: 2) is substituted with K or R.

9. The polynucleotide of claim 1, wherein one or more hydrophobic residues within the sequence LIAML (SEQ ID NO: 8) in the Listerial ActA protein sequence are substituted with amino acids which are not hydrophobic.

10. The polynucleotide of claim 9, wherein the sequence LIAML (SEQ ID NO: 8) is replaced with the sequence QDNKR (SEQ ID NO: 9).

11. The polynucleotide of claim 1, wherein the polypeptide comprises SEQ ID NO: 30 or SEQ ID NO: 31.

12. The polynucleotide of claim 1, wherein the promoter is an actA or hly promoter.

13. The polynucleotide of claim 1, wherein the non-Listerial antigen is a cancer cell, tumor, or infectious agent antigen.

14. A plasmid comprising the polynucleotide of claim 1.

15. A *Listeria* bacterium comprising the polynucleotide of claim 1.

16. The *Listeria* bacterium of claim 15, which is *Listeria monocytogenes*.

17. The *Listeria* bacterium of claim 15, which is attenuated by a functional deletion of the bacterium's genomic actA gene.

18. The *Listeria* bacterium of claim 15, wherein the polynucleotide is inserted into the bacterium's genomic actA or inlB gene.

19. A vaccine comprising the *Listeria* bacterium of claim 15 and a pharmacologically acceptable excipient.

20. A method of producing a *Listeria* bacterium for use in a vaccine, comprising:

integrating a polynucleotide of claim 1 into the genome of the *Listeria* bacterium.

21. The method of claim 20, wherein the polynucleotide of claim 1 is inserted into the bacterium's genomic actA or inlB gene.

* * * * *

SEQUENCE LISTING

```
<160> NUMBER OF SEQ ID NOS: 51

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 1

Lys Thr Glu Glu Gln Pro Ser Glu Val Asn Thr Gly Pro
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Thr Glu Glu Gln Pro Ser Glu Val Asn Thr Gly Pro Arg
1               5                   10

<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
            20                  25

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Asn Glu Glu Val Asn Ala Ser Asp Phe Pro Pro Pro Pro Thr Asp
1               5                   10                  15

Glu Glu Leu Arg
            20

<210> SEQ ID NO 5
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Arg Gly Gly Ile Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Glu Ile
            20                  25                  30

Asp Arg

<210> SEQ ID NO 6
<211> LENGTH: 19
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 6

Lys Glu Asn Ser Ile Ser Ser Met Ala Pro Pro Ala Ser Pro Pro Ala
1               5                   10                  15

Ser Pro Lys

<210> SEQ ID NO 7
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Ser Ile Ser Ser Met Ala Pro Pro Ala Ser Pro Pro Ala Ser Pro
1               5                   10                  15

Lys Thr Pro Ile Glu Lys Lys His Ala Asp
            20                  25

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Ile Ala Met Leu
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Asp Asn Lys Arg
1               5

<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala
            20                  25

<210> SEQ ID NO 11
<211> LENGTH: 23
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 11

Met Lys Lys Ile Met Leu Val Phe Ile Thr Leu Ile Leu Val Ser Leu
1               5                   10                  15

Pro Ile Ala Gln Gln Thr Glu
            20

<210> SEQ ID NO 12
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Val Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Lys Thr
        35                  40                  45

Glu Glu Gln Pro Ser Glu Val Asn Thr Gly Pro Arg Tyr Glu Thr Ala
    50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly
            100

<210> SEQ ID NO 13
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Lys Thr
        35                  40                  45

Glu Glu Gln Pro Ser Glu Val Asn Thr Gly Pro Arg Tyr Glu Thr Ala
    50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly
            100

<210> SEQ ID NO 14
<211> LENGTH: 102
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 14

```
Val Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Lys Thr
        35                  40                  45

Glu Glu Gln Pro Ser Glu Val Asn Thr Gly Pro Arg Tyr Glu Thr Ala
    50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly Gly Ser
            100
```

<210> SEQ ID NO 15
<211> LENGTH: 102
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Lys Thr
        35                  40                  45

Glu Glu Gln Pro Ser Glu Val Asn Thr Gly Pro Arg Tyr Glu Thr Ala
    50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly Gly Ser
            100
```

<210> SEQ ID NO 16
<211> LENGTH: 86
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Val Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Tyr Glu
        35                  40                  45
```

```
Thr Ala Arg Glu Val Ser Ser Arg Asp Ile Glu Glu Leu Glu Lys Ser
        50                  55                  60

Asn Lys Val Lys Asn Thr Asn Lys Ala Asp Gln Asp Asn Lys Arg Lys
 65                  70                  75                  80

Ala Lys Ala Glu Lys Gly
                85

<210> SEQ ID NO 17
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Gly Leu Asn Arg Phe Met Arg Ala Met Met Val Val Phe Ile Thr
 1               5                  10                  15

Ala Asn Cys Ile Thr Ile Asn Pro Asp Ile Ile Phe Ala Ala Thr Asp
                20                  25                  30

Ser Glu Asp Ser Ser Leu Asn Thr Asp Glu Trp Glu Glu Glu Tyr Glu
        35                  40                  45

Thr Ala Arg Glu Val Ser Ser Arg Asp Ile Glu Glu Leu Glu Lys Ser
        50                  55                  60

Asn Lys Val Lys Asn Thr Asn Lys Ala Asp Gln Asp Asn Lys Arg Lys
 65                  70                  75                  80

Ala Lys Ala Glu Lys Gly
                85

<210> SEQ ID NO 18
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Lys Lys Ile Met Leu Val Phe Ile Thr Leu Ile Leu Val Ser Leu
 1               5                  10                  15

Pro Ile Ala Gln Gln Thr Glu Ala Lys
                20                  25

<210> SEQ ID NO 19
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Lys Lys Ile Met Leu Val Phe Ile Thr Leu Ile Leu Val Ser Leu
 1               5                  10                  15

Pro Ile Ala Gln Gln Thr Glu Ala Lys Asp Ala Ser Ala Phe Asn Lys
                20                  25                  30

Glu Asn Ser Ile Ser Ser Met Ala Pro Pro Ala Ser Pro Ala Ser
        35                  40                  45

Pro Lys Thr Pro Ile Glu Lys Lys His Ala Asp Glu Ile Asp Lys Tyr
        50                  55                  60
```

Ile Gln Gly Leu Asp Tyr Asn Lys Asn Asn Val Leu Val Tyr His Gly
 65                  70                  75                  80

Asp Ala Val Thr Asn Val Pro Pro Arg Lys Gly Tyr Lys Asp Gly Asn
                 85                  90                  95

Glu Tyr Ile Val Val Glu Lys Lys Lys Ser Ile Asn Gln Asn Asn
             100                 105                 110

Ala Asp Ile Gln Val Val Asn Ala Ile Ser Ser Leu Thr Tyr Pro Gly
             115                 120                 125

Ala Leu Val Lys Ala Asn Ser Glu Leu Val Glu Asn Gln Pro Asp Val
        130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp
        435                 440

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Ser Ile Ile Asn Phe Glu Lys Leu
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Met Gln Met Leu Lys Glu Thr Ile
1               5

<210> SEQ ID NO 22
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
                20                  25                  30

Ser Glu Asp Ser Ser Leu Asn Thr Asp Glu Trp Glu Glu Lys Thr
        35                  40                  45

Glu Gln Pro Ser Glu Val Asn Thr Gly Pro Arg Tyr Glu Thr Ala Arg
    50                  55                  60

Glu Val Ser Ser Arg Asp Ile Glu Glu Leu Glu Lys Ser Asn Lys Val
65                  70                  75                  80

Lys Asn Thr Asn Lys Ala Asp Leu Ile Ala Met Leu Lys Ala Lys Ala
                85                  90                  95

Glu Lys Gly Gly Ser
            100

<210> SEQ ID NO 23
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
                20                  25                  30

Ser Glu Asp Ser Ser Leu Asn Thr Asp Glu Trp Glu Glu Tyr Glu
        35                  40                  45

Thr Ala Arg Glu Val Ser Ser Arg Asp Ile Glu Glu Leu Glu Lys Ser
    50                  55                  60

Asn Lys Val Lys Asn Thr Asn Lys Ala Asp Gln Asp Asn Lys Arg Lys
65                  70                  75                  80

Ala Lys Ala Glu Lys Gly Leu
                85

<210> SEQ ID NO 24
<211> LENGTH: 1490
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
ggtaccggga agcagttggg gttaactgat aacaaatgt tagagaaaaa ttaattctcc      60
aagtgatatt cttaaaataa ttcatgaata ttttttctta tattagctaa ttaagaagat    120
aattaactgc taatccaatt tttaacgaaa taaattagtg aaaatgaagg ccgaattttc    180
cttgttctaa aaaggttgta ttagcgtatc acgaggaggg agtataagtg ggattaaata    240
gatttatgcg tgcgatgatg gtagttttca ttactgccaa ctgcattacg attaaccccg    300
acataatatt tgcagcgaca gatagcgaag attccagtct aaacacagat gaatgggaag    360
aagaatacga aactgcacgt gaagtaagtt cacgtgatat tgaggaacta gaaaaatcga    420
ataaagtgaa aaatacgaac aaagcagacc aagataataa acgtaaagca aaagcagaga    480
aaggtggatc cgcaagcaaa gtattgccag ctagtcgtgc attagaggag aaaaagggga    540
attacgtggt gacggatcat ggatcgtgtg ccgatggctc agtaaagact agtgcgagca    600
aagtggcccc tgcatcacga gcacttgaag agaaaaaagg aaactatgtt gtgaccgatc    660
atggtagctg cggagatggt tcaattaaat tatcaaaagt cttaccagca tctagagctt    720
tagaggaaaa gaagggtaac tatgtcgtaa cagatcatgg aagttgtgct gacggaagtg    780
ttaaagcgtc gaaagtagct ccagcttctc gcgcattaga agaaaagaaa ggcaattatg    840
ttgtaacaga ccatggtagt tgtggtgatg gctcgatcaa attgtcaaaa gttctaccgg    900
cttctcgtgc gctagaagag aagaaaggaa attacgtagt tacagaccac ggctcttgcg    960
cggatggttc cgttaaacaa ttgatgcaag ctgaaggaag aggaactggg ggtagtacag   1020
gagatgcaga tggccctggc ggaccgggta ttcctgatgg accagggggt aatgcgggtg   1080
ggccaggcga agcaggtgct acaggcggta gagggccacg aggggcagga gcagcgagag   1140
cttctggacc aggtggtggc gctccacgcg gtccgcatgg tggtgcagcg tccggcttaa   1200
acggttgctg tcgctgtgga gctagaggac cagaatcacg tcttttagag ttctatttgg   1260
ccatgccgtt tgctacgcct atggaagcag aactagcacg tcgtagctta gcgcaagatg   1320
cacctccatt accagttcca ggcgtgttgt taaaggagtt cacggtcagt ggtaacatat   1380
tgacaattcg ccttactgcg gctgaccacc gtcaattaca gcttagcatt tcatcttgtt   1440
tacaacaact ttcgttactt atgtggatca cccaatgcta aggcggccgc                1490
```

<210> SEQ ID NO 25
<211> LENGTH: 417
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp

```
                   20                  25                  30
        Ser Glu Asp Ser Ser Leu Asn Thr Asp Glu Trp Glu Glu Tyr Glu
                    35                  40                  45

Thr Ala Arg Glu Val Ser Ser Arg Asp Ile Glu Glu Leu Glu Lys Ser
         50                  55                  60

Asn Lys Val Lys Asn Thr Asn Lys Ala Asp Gln Asp Asn Lys Arg Lys
         65                  70                  75                  80

Ala Lys Ala Glu Lys Gly Gly Ser Ala Ser Lys Val Leu Pro Ala Ser
                        85                  90                  95

Arg Ala Leu Glu Glu Lys Lys Gly Asn Tyr Val Val Thr Asp His Gly
                       100                 105                 110

Ser Cys Ala Asp Gly Ser Val Lys Thr Ser Ala Ser Lys Val Ala Pro
                       115                 120                 125

Ala Ser Arg Ala Leu Glu Glu Lys Lys Gly Asn Tyr Val Val Thr Asp
                       130                 135                 140

His Gly Ser Cys Gly Asp Gly Ser Ile Lys Leu Ser Lys Val Leu Pro
        145                 150                 155                 160

Ala Ser Arg Ala Leu Glu Glu Lys Lys Gly Asn Tyr Val Val Thr Asp
                       165                 170                 175

His Gly Ser Cys Ala Asp Gly Ser Val Lys Ala Ser Lys Val Ala Pro
                       180                 185                 190

Ala Ser Arg Ala Leu Glu Glu Lys Lys Gly Asn Tyr Val Val Thr Asp
                       195                 200                 205

His Gly Ser Cys Gly Asp Gly Ser Ile Lys Leu Ser Lys Val Leu Pro
                       210                 215                 220

Ala Ser Arg Ala Leu Glu Glu Lys Lys Gly Asn Tyr Val Val Thr Asp
        225                 230                 235                 240

His Gly Ser Cys Ala Asp Gly Ser Val Lys Gln Leu Met Gln Ala Glu
                       245                 250                 255

Gly Arg Gly Thr Gly Gly Ser Thr Gly Asp Ala Asp Gly Pro Gly Gly
                       260                 265                 270

Pro Gly Ile Pro Asp Gly Pro Gly Asn Ala Gly Gly Pro Gly Glu
                       275                 280                 285

Ala Gly Ala Thr Gly Gly Arg Gly Pro Arg Gly Ala Gly Ala Ala Arg
                       290                 295                 300

Ala Ser Gly Pro Gly Gly Ala Pro Arg Gly Pro His Gly Gly Ala
        305                 310                 315                 320

Ala Ser Gly Leu Asn Gly Cys Cys Arg Cys Gly Ala Arg Gly Pro Glu
                       325                 330                 335

Ser Arg Leu Leu Glu Phe Tyr Leu Ala Met Pro Phe Ala Thr Pro Met
                       340                 345                 350

Glu Ala Glu Leu Ala Arg Arg Ser Leu Ala Gln Asp Ala Pro Pro Leu
                       355                 360                 365

Pro Val Pro Gly Val Leu Leu Lys Glu Phe Thr Val Ser Gly Asn Ile
                       370                 375                 380

Leu Thr Ile Arg Leu Thr Ala Ala Asp His Arg Gln Leu Gln Leu Ser
        385                 390                 395                 400

Ile Ser Ser Cys Leu Gln Gln Leu Ser Leu Leu Met Trp Ile Thr Gln
                       405                 410                 415

Cys

<210> SEQ ID NO 26
<211> LENGTH: 9
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Arg Gly Pro Glu Ser Arg Leu Leu
1               5

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Ile Ser Ser Met Ala Pro Pro Ala Ser Pro Pro Ala Ser Pro Lys
1               5                   10                  15

Thr Pro Ile Glu
            20

<210> SEQ ID NO 28
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Ile Ser Ser Met Ala Pro Pro Ala Ser Pro Pro Ala Ser Pro Lys
1               5                   10                  15

Thr Pro Ile Glu Lys Lys His Ala Asp
            20                  25

<210> SEQ ID NO 29
<211> LENGTH: 102
<212> TYPE: PRT
<213> ORGANISM: Listeria monocytogenes

<400> SEQUENCE: 29

Val Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
                20                  25                  30

Ser Glu Asp Ser Ser Leu Asn Thr Asp Glu Trp Glu Glu Glu Lys Thr
            35                  40                  45

Glu Glu Gln Pro Ser Glu Val Asn Thr Gly Pro Arg Tyr Glu Thr Ala
        50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly Gly Ser
            100

<210> SEQ ID NO 30
<211> LENGTH: 89
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 30

Val Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Arg Tyr
        35                  40                  45

Glu Thr Ala Arg Glu Val Ser Ser Arg Asp Ile Glu Glu Leu Glu Lys
    50                  55                  60

Ser Asn Lys Val Lys Asn Thr Asn Lys Ala Asp Leu Ile Ala Met Leu
65                  70                  75                  80

Lys Ala Lys Ala Glu Lys Gly Gly Ser
                85

<210> SEQ ID NO 31
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Val Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Tyr Glu
        35                  40                  45

Thr Ala Arg Glu Val Ser Ser Arg Asp Ile Glu Glu Leu Glu Lys Ser
    50                  55                  60

Asn Lys Val Lys Asn Thr Asn Lys Ala Asp Gln Asp Asn Lys Arg Lys
65                  70                  75                  80

Ala Lys Ala Glu Lys Gly Gly Ser
                85

<210> SEQ ID NO 32
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Val Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Lys Thr
        35                  40                  45

Glu Glu Gln Pro Ser Glu Val Asn Thr Gly Pro Arg Tyr Glu Thr Ala
    50                  55                  60

Arg Glu Val Ser Ser Arg Asp Ile Glu Glu Leu Glu Lys Ser Asn Lys
65                  70                  75                  80
```

Val Lys Asn Thr Asn Lys Ala Asp Gln Asp Asn Lys Arg Lys Ala Lys
            85                  90                  95

Ala Glu Lys Gly Gly Ser
            100

<210> SEQ ID NO 33
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Val Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Lys Thr
            35                  40                  45

Glu Glu Gln Pro Ser Glu Val Asn Thr Gly Pro Arg Tyr Glu Thr Ala
        50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
            85                  90                  95

Ala Glu Lys Gly Gly Ser
            100

<210> SEQ ID NO 34
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Val Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Arg Tyr
            35                  40                  45

Glu Thr Ala Arg Glu Val Ser Ser Arg Asp Ile Glu Glu Leu Glu Lys
        50                  55                  60

Ser Asn Lys Val Lys Asn Thr Asn Lys Ala Asp Leu Ile Ala Met Leu
65                  70                  75                  80

Lys Ala Lys Ala Glu Lys Gly Gly Ser
            85

<210> SEQ ID NO 35
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Val Gly Leu Asn Arg Phe Met Arg Ala Met Met Val Val Phe Ile Thr

-continued

```
                1               5                   10                  15
Ala Asn Cys Ile Thr Ile Asn Pro Asp Ile Ile Phe Ala Ala Thr Asp
                20                  25                  30

Ser Glu Asp Ser Ser Leu Asn Thr Asp Glu Trp Glu Glu Tyr Glu
            35                  40                  45

Thr Ala Arg Glu Val Ser Ser Arg Asp Ile Glu Glu Leu Glu Lys Ser
        50                  55                  60

Asn Lys Val Lys Asn Thr Asn Lys Ala Asp Gln Asp Asn Lys Arg Lys
65                  70                  75                  80

Ala Lys Ala Glu Lys Gly Gly Ser
                85
```

<210> SEQ ID NO 36
<211> LENGTH: 102
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

```
Val Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
                20                  25                  30

Ser Glu Asp Ser Ser Leu Asn Thr Asp Glu Trp Glu Glu Lys Thr
            35                  40                  45

Glu Glu Gln Pro Ser Glu Val Asn Thr Gly Pro Arg Tyr Glu Thr Ala
        50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Gln Asp Asn Lys Arg Lys Ala Lys
                85                  90                  95

Ala Glu Lys Gly Gly Ser
                100
```

<210> SEQ ID NO 37
<211> LENGTH: 100
<212> TYPE: PRT
<213> ORGANISM: Listeria monocytogenes

<400> SEQUENCE: 37

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
                20                  25                  30

Glu Asn Ser Ile Ser Ser Met Ala Pro Pro Ala Ser Pro Pro Ala Ser
            35                  40                  45

Pro Lys Thr Pro Ile Glu Lys Lys His Ala Asp Glu Ile Asp Lys Tyr
        50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val
            100
```

<210> SEQ ID NO 38
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Glu Ile Asp Lys Tyr Ile Gln Gly Leu Asp Tyr Asn Lys Asn Asn
        35                  40                  45

Val Leu Val Tyr His Gly Asp Ala Val Thr Asn Val Pro Pro Arg Lys
    50                  55                  60

Gly Tyr Lys Asp Gly Asn Glu Tyr Ile Val
65                  70

<210> SEQ ID NO 39
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Thr
            20                  25                  30

Pro Ile Glu Lys Lys His Ala Asp Glu Ile Asp Lys Tyr Ile Gln Gly
        35                  40                  45

Leu Asp Tyr Asn Lys Asn Asn Val Leu Val Tyr His Gly Asp Ala Val
    50                  55                  60

Thr Asn Val Pro Pro Arg Lys Gly Tyr Lys Asp Gly Asn Glu Tyr Ile
65                  70                  75                  80

Val

<210> SEQ ID NO 40
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val
            100

<210> SEQ ID NO 41
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Ala Ser
        35                  40                  45

Pro Lys Thr Pro Ile Glu Lys Lys His Ala Asp Glu Ile Asp Lys Tyr
50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val
            100

<210> SEQ ID NO 42
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Glu Ile Asp Lys Tyr Ile Gln Gly Leu Asp Tyr Asn Lys Asn Asn
        35                  40                  45

Val Leu Val Tyr His Gly Asp Ala Val Thr Asn Val Pro Pro Arg Lys
    50                  55                  60

Gly Tyr Lys Asp Gly Asn Glu Tyr Ile Val
65                  70

<210> SEQ ID NO 43
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Thr

```
                20                  25                  30

Pro Ile Glu Lys Lys His Ala Asp Glu Ile Asp Lys Tyr Ile Gln Gly
            35                  40                  45

Leu Asp Tyr Asn Lys Asn Asn Val Leu Val Tyr His Gly Asp Ala Val
        50                  55                  60

Thr Asn Val Pro Pro Arg Lys Gly Tyr Lys Asp Gly Asn Glu Tyr Ile
65                  70                  75                  80

Val

<210> SEQ ID NO 44
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val
            100

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Glu Glu Glu Lys Thr Glu Glu Gln Pro Ser Glu
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Ala Ala Ala Thr Ala Ala Gln Pro Ser Ala
1               5                   10

<210> SEQ ID NO 47
<211> LENGTH: 33
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 47

Leu Asn Thr Asp Glu Trp Glu Glu Glu Lys Thr Glu Glu Gln Pro Ser
1               5                   10                  15

Glu Val Asn Thr Gly Pro Arg Tyr Glu Thr Ala Arg Glu Val Ser Ser
            20                  25                  30

Arg

<210> SEQ ID NO 48
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Leu Asn Thr Asp Glu Trp Ala Ala Ala Thr Ala Ala Gln Pro Ser
1               5                   10                  15

Ala Val Asn Thr Gly Pro Arg Tyr Glu Thr Ala Arg Glu Val Ser Ser
            20                  25                  30

Arg

<210> SEQ ID NO 49
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Asn Thr Asp Glu Trp Glu Glu Glu Tyr Glu Thr Ala Arg Glu Val
1               5                   10                  15

Ser Ser Arg

<210> SEQ ID NO 50
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Leu Asn Thr Asp Glu Trp Glu Glu Glu Lys Arg Lys Arg Gln Arg Lys
1               5                   10                  15

Arg Val Asn Arg Gly Lys Arg Tyr Glu Thr Ala Arg Glu Val Ser Ser
            20                  25                  30

Arg

<210> SEQ ID NO 51
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Leu Asn Thr Asp Glu Trp Glu Glu Glu Lys Lys Arg Lys Gln Lys Arg

-continued

```
1               5                   10                  15
Lys Val Asn Lys Gly Arg Arg Tyr Glu Thr Ala Arg Glu Val Ser Ser
            20                  25                  30
Arg
```